US009315867B2

(12) United States Patent
Brentnall et al.

(10) Patent No.: US 9,315,867 B2
(45) Date of Patent: Apr. 19, 2016

(54) COMPOSITIONS AND METHODS FOR DETECTING CANCER

(75) Inventors: Teresa A. Brentnall, Seattle, WA (US); Ru Chen, Seattle, WA (US); Katherine L. Pogue-Geile, Pittsburgh, PA (US); David C. Whitcomb, Allison Park, PA (US); Mary Patricia Bronner, Moreland Hills, OH (US); Carol A. Otey, Chapel Hill, NC (US)

(73) Assignees: UNIVERSITY OF WASHINGTON, Seattle, WA (US); UNIVERSITY OF NORTH CAROLINA AT CHAPEL HILL, Chapel Hill, NC (US); THE CLEVELAND CLINIC FOUNDATION, Cleveland, OH (US); UNIVERSITY OF PITTSBURG, Pittsburgh, PA (US)

( * ) Notice: Subject to any disclaimer, the term of this patent is extended or adjusted under 35 U.S.C. 154(b) by 1263 days.

(21) Appl. No.: 12/939,801

(22) Filed: Nov. 4, 2010

(65) Prior Publication Data

US 2011/0104694 A1   May 5, 2011

Related U.S. Application Data

(62) Division of application No. 11/840,112, filed on Aug. 16, 2007, now Pat. No. 7,851,144.

(60) Provisional application No. 60/838,746, filed on Aug. 18, 2006.

(51) Int. Cl.
   *C12Q 1/68*    (2006.01)
   *G01N 33/574*  (2006.01)

(52) U.S. Cl.
   CPC ........ *C12Q 1/6886* (2013.01); *G01N 33/57411* (2013.01); *G01N 33/57415* (2013.01); *G01N 33/57438* (2013.01); *C12Q 2600/112* (2013.01); *C12Q 2600/154* (2013.01)

(58) Field of Classification Search
   None
   See application file for complete search history.

(56) References Cited

U.S. PATENT DOCUMENTS

| 6,642,009 | B2 | 11/2003 | Hung |
| 2004/0029114 | A1 | 2/2004 | Mack |
| 2004/0038281 | A1* | 2/2004 | Hung ................................ 435/6 |
| 2004/0076955 | A1 | 4/2004 | Mack |
| 2006/0024692 | A1 | 2/2006 | Nakamura et al. |
| 2006/0216707 | A1 | 9/2006 | Stuhlmuller et al. |

FOREIGN PATENT DOCUMENTS

| WO | WO 02/059377 | 8/2002 |
| WO | WO 03/025138 | 3/2003 |
| WO | WO 03/039443 | 5/2003 |
| WO | WO2004085675 | * 3/2004 |
| WO | WO 2004/003140 | 4/2004 |
| WO | WO 2004/031413 | 4/2004 |
| WO | WO 2004/085675 | 10/2004 |
| WO | WO 2005/094306 | 10/2005 |
| WO | WO 2006/017635 | 2/2006 |
| WO | WO 2006/002433 | 5/2006 |

OTHER PUBLICATIONS

Mesh word and sequence search for palladin (KIAA0992) NCBI database 2009.*
Ryu et al Cancer Res. vol. 61, p. 1833-1838, 2001.*
Boring et al. (1994) "Cancer Statistics, 1994" *CA Cancer J. Clin* 44:7-26.
Boukhelifa et al. (2001) "A Role for the Cytoskeleton-associated Protein Palladin in Neurite Outgrowth" *Molecular Biology of the Cell* 12:2721-2729.
Eberle et al. (2002) "A New Suspectibility Locus for Autosomal Dominant Pancreatic Cancer Maps to Chromosome 4q32-34" *Am J Hum Genet* 70:1044-1048.
Ghadirian et al. (1991) Reported Family Aggregation of Pancreatic Cancer Within a Population Based Case-Control study in the Francophone Community in Montreal, Canada: *Int J Pancreatol* 10:183-196.
Hruban et al. (1999) "Familial pancreatic cancer" *Annals of Oncology* 10 Suppl 4:69-73.
Lee et al. (2003) *PNAS* 100:2651-56.
Lynch, et al. (1996) "Familial Pancreatic Cancer: A Review" *Seminars in Oncology* 23:251-275.
Mykkänen et al. (2001) "Characterization of Human Palladin, a Microfilament-associated Protein" *Molecular Biology of the Cell* 12:3060-3073.
Parast and Otey (2000) "Characterization of Palladin, a Novel Protein Localized to Stress Fibers and Cell Adhesions" *The J of Cell Biology* 150:643-655.
Pohl et al. (2005) "Inactivation of the Mitogen-Activated Protein Kinase Pathway as a Potential Target-Based Therapy in Ovarian Serous Tumors with KRAS or BRAF Mutations" *Cancer Res.* 65:1994.
Rachlin and Otey (2006) "Identification of Paladin Isoforms and Characterization of an Isoform-specific Interaction Between Lasp-1 and Palladin" *Journal of Cell Science* 119:995-1004.
Ryu et al. (2001) *Cancer Res* 61:1833-1838.
Silverman et al. (1999) "Diabetes Mellitus, Other Medical Conditions and Familial History of Cancer as Risk Factors for Pancreatic Cancer" *British Journal of Cancer* 80:1830-1837.
Zogopoulous et al. (2007) *Hum Genet* 121:635-637.
Mesh word search for palladin, 2009.
Sequence search result-1, 2009.

* cited by examiner

*Primary Examiner* — Lei Yao

(74) *Attorney, Agent, or Firm* — Karen S. Canady; Canady + Lortz LLP

(57) ABSTRACT

The present invention provides methods and compositions involving detecting the presence of and/or assessing the risk of cancer in a subject. These methods include methods of detecting and diagnosing cancer in an individual; methods of identifying individuals at risk of developing a cancer; and methods of staging a cancer. The methods generally involve detecting a palladin gene nucleotide sequence alteration that has been found to be associated with cancer and/or detecting a level of a palladin mRNA and/or protein in a biological sample. The present invention further provides nucleic acid probes, nucleic acid primers, and antibodies, as well as kits comprising one or more of the same, for use in a subject method.

13 Claims, 22 Drawing Sheets

FIG. 1A

SEQ ID NO:1

```
   1 cctgagtcac ccggcgggcg aggtataaag cccgatacct gccccgcgcc cggtccgcgg
  61 agcccgctgc agctcccgct cgctccggac gcggaatcgg gcagcagcgg gaggcggccc
 121 ggagagccga gggaccctct gaagctccag caactccaga accaaatccg actggagcag
 181 gaggccggcg ctggcagcc tccgccagcc ccgcgcagcg cgccgccctc gccccccttc
 241 ccgccgccgc ccgccttccc cgagctcgcg gctgcacgc cgccgcgtc ccggagccc
 301 atgagcgcgc tggcctcccg ctccgccccc gccatgcagt cctccggctc cttcaactac
 361 gcgcgcccca agcagttcat cgccgcgcag aacctcgggc ccgcgtcggg ccacggcacg
 421 ccggcctcca gcccagctc gtccagcctc ccgtcgccca tgtcccccgac gccgaggcag
 481 ttcggccgcg ccccgtgcc gcccttccg cagcccttcg gcgctgagcc cgaggcccg
 541 tgggctcct cctcgccgtc gccccgcc ccgccaccc cggtcttcag cccacggct
 601 gccttccgg tgccgacgt gttcccactg ccgccgccac cacgccgct cccgagcccg
 661 ggacaggcgt cccactgctc gtcgcctgcc acccgcttcg gccacggcca gacgcccgcg
 721 gccttcctca gcgctctgct gcctcgcag ccgccgccgg cggccgtcaa cgccctgggg
 781 ctgccaagg gtgtcacccc cgcaggattt ccaagaagg ccagtagaac tgctagaata
 841 gcctccgatg aggaaattca aggcacaaag gatgctgtta ttcaagacct ggaacgaaaa
 901 cttcgcttca aggaggacct cctgaacaat ggccagccga ggttaacata cgaagaaga
 961 atggctcgtc gactgctagg tgctgacagt gcaactgtct ttaatattca ggagccagaa
1021 gaggaaacag ctaatcagga atacaaagtc tccagctgtg aacagagact catcagtgaa
1081 atagagtaca ggctagaaag gtctcctgtg gatgaatcag gtgatgaagt tcagtatgga
1141 gatgtgcctg tggaaaatgg aatggcacca ttttttgaga tgaagctgaa acattacaag
1201 atctttgagg gaatgccagt aactttcaca tgtagagtgg ctggaaatcc aaagccaaag
1261 atctattggt ttaaagatgg gaagcagatc tctccaaaga gtgatcacta caccattcaa
1321 agagatctcg atgggacctg ctccctccat accacagcct ccacctaca tgatgatggg
1381 aattatacaa ttatggctgc aaaccctcag ggccgcatca gttgtactgg acggctaatg
1441 gtacaggctg tcaaccaaag aggtcgaagt cccggtctc cctcaggcca tcctcatgtc
1501 agaggcctc gttctagatc aagggacagt ggagacgaaa atgaaccaat tcaggagcga
1561 ttcttcagac ctcacttctt gcaggctcct ggagatctga ctgttcaaga aggaaactc
1621 tgcagaatgg actgcaaagt cagtgggtta ccaacccag atctaagctg gcaactagat
1681 ggaaagcccg tacgcctga cagtgctcac aagatgctgg tgcgtgagaa cgggtgcac
1741 tctctgatca tagagccagt cacgtcacgt gatgccggca tctacacatg tatagctacc
1801 aaccgagcag gacagaactc attcagcctg gagcttgtgg ttgctgctaa agaagcacac
1861 aaacccctg tgtttattga agctccaa acacaggag ttgctgatgg gtaccagtg
1921 cggctggaat gtcgtgtatt gggagtgcca ccactcaga tattttggaa gaaagaaaat
1981 gaatcactca ctcacagcac tgaccgagtg agcatgcacc aggacaacca cggctacatc
2041 tgcctgctca ttcaggagc cacaaaagaa gatgctgggt ggtatactgt gtcagccaag
2101 aatgaagcag ggattgtgtc ctgtactgcc aggctggacg tttacaccca gtggcatcag
2161 cagtcacaga gcaccaagcc aaaaaaagta cggccctcag ccagtcgcta tgcagcactt
2221 tcggaccagg gactagacat caaagcagcg ttccaacctg aggccaaccc atctcacctg
2281 acactgaata ctgccttggt agaaagtgag gacctgtaat ccagcattct tgttaaagct
2341 gaaacactga acagccatt gccttgacca acatattcct ttgtcacatt atgtaaaagg
2401 cagaaacata cctttgacta taagaaatta aaaaaaaaca ccaaaataat atttttctta
2461 cttgatatac caaacttagt ttaagtagat aatgctaata caatataca cattgcacag
2521 aaaatacaca tttactgtcc aatttaaaac tttggaattg ctgtgattaa agtgatcaaa
2581 atgccaaaat actaaggaa atcaattgtt cacaggtaac tacaatttgt attatctaca
2641 agtgccttta aacacaagat ataggtgctg tgtagcctga tagtgtgaaa tgtttaatga
2701 gggagttgta ccacaaacag tactacaatg attctgaagc acagtgtatt cagacagata
2761 cagtgaacca agtgcaatat gtaaggatga agaagaga gatgacaaag aaatccaagt
2821 aaatgccttg tctttgcaaa tgttttata ttaaatcata aggaaggaac tacttgcctt
2881 aaatgttaat atcaaagag tttctaaca aggttaatac cttagttctt aacattttt
2941 ttctttatgt gtagtgtttt catgctacct tggtaggaaa cttatttaca aaccatatta
```

FIG. 1B

```
3001 aaaggctaat ttaaatataa ataatataaa gtgctctgaa taaagcagaa atatattaca
3061 gttcattcca cagaaagcat ccaaaccacc caaatgacca aggcatatat agtatttgga
3121 ggaatcaggg gtttggaagg agtagggagg agaatgaagg aaaatgcaac cagcatgatt
3181 atagtgtgtt caattagata aaagtagaag gcacaggaga ggtagcaaag gccaggcttt
3241 tctttggttt tcttcaaaca taggtgaaaa aaacactgcc attcacaagt caaggaaccc
3301 agggccagct ggaagtgtgg agcacacatg ctgtggagca cacatgctgt ggagattgca
3361 gtgtgtctga ggtttgtgta gtagtggaag attttaggta tgtagagcaa gttgaaaatg
3421 gattgagact gcatggtggc ataaatgaga aattgcctgt agcatctagt ctacttgaag
3481 gaagtggaga cataaggaga gacaaaaaca ggtttgtgcc ataaagtatt ttttcaaaga
3541 caccaagatg tggtaaatga aaattattag ttcacttccc tgctgccatg aaactttgcc
3601 ttaagaaggt gctggattcc aaggtttgta aaggcatctc ggtaaagact gcttttgaa
3661 tgcatatgat tttgcatcag ctagactgag ttgattctga ccagacttga tggttttaag
3721 tcggaaccga taaattttaa aaaggagaaa aaataatttg acctagtagt ataaaacatg
3781 aggctttaat ggtactttgc tatgaaaaga aaacactgta ttccttatgc aaaacacatg
3841 tatctttcat tatttataag tggcctctct tagctcagtt actcaattca tacgtagtat
3901 tttttaaaat aattttatat ctgtgtacca ccccatatat ttcatattac tgtttcacat
3961 gtacagcttt ctacttcttt gtaagaacac caaccaacca aggtttaagt gattaatagg
4021 cttgagcacc gggtggcaga tgttctatgc agtgtggttc aagtttcttt gaccgcactt
4081 atatgcattg ctaatatgga atttaagata ccatacacag tctctcatgg acctatctct
4141 attgtagaat tatgacttat gtcttacttg gcaaattttt ctgaatgtga ccttttttg
4201 ctgatttgct gggtttggga ttaactagca ttattttgcc acctttatat tgtatttata
4261 aaaaaaaagt actatcaatc aatcatacta ctttggattg ttgtgctggt gtaatgtgga
4321 tttaacatca ataaatattt gacaaat
```

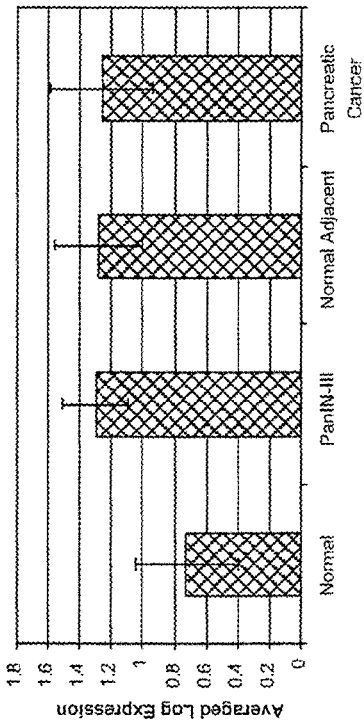
FIG. 3A
FIG. 3C
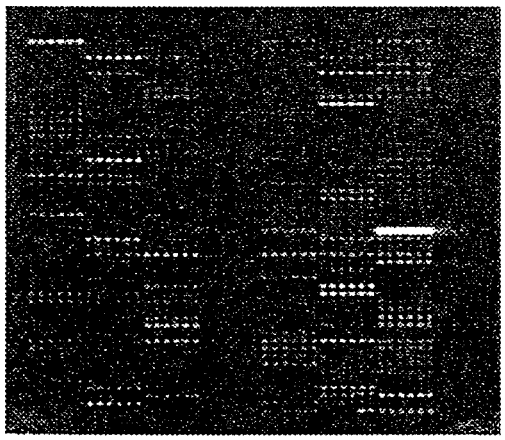
FIG. 3B
| Gene Name | Sporadic | Family X |
|---|---|---|
| 1. KIAA0992: palladin IMAGE:2542582 | 21.3 | 14.564 |
| 2. KIAA0992 protein IMAGE:469720 | 13.021 | 2.357 |

FIG. 5

| | | | | | | | |
|---|---|---|---|---|---|---|---|
| Human | S | Q | T | P | A | A | F |
| Chimp | S | Q | T | P | A | A | F |
| Mouse | S | Q | T | P | A | A | F |
| Rat | S | Q | T | P | A | A | F |
| Chicken | G | Q | S | P | A | A | F |
| Zebra Fish | C | Q | T | P | P | A | P |
| Family X | S | Q | T | [S] | A | A | F |

FIG. 10

```
621 ggacaggcgt cccactgctc gtcgcctgcc acccgcttcg gccacggcca gacgtccgcg
    gccttcctca gcgctctgct gccctcgcag ccgccgccgg cggccgtcaa cgccctgggg 780
(SEQ ID NO:63)
```

Forward primer: 5'-ggacaggcgtccactgctc-3' (SEQ ID NO:64)

Reverse primer: 5'-ccccagggcgttgacggccg-3' (SEQ ID NO:65)

FIG. 11

BAA76836 palladin protein

PESPGGRGIKPDTCPAPGPRSPLQLPLAPDAESGSSGRRPGEPR
DPLKLQQLQNQIRLEQEAGARQPPPAPRSAPPSPPFPPPPAFPELAACTPPASPEPMS
ALASRSAPAMQSSGSFNYARPKQFIAAQNLGPASGHGTPASSPSSSSLPSPMSPTPRQ
FGRAPVPPFAQPFGAEPEAPWGSSSPSPPPPPPPVFSPTAAFPVPDVFPLPPPPPPLP
SPGQASHCSSPATRFGHGQTPAAFLSALLPSQPPPAAVNALGLPKGVTPAGFPKKASR
TARIASDEEIQGTKDAVIQDLERKLRFKEDLLNNGQPRLTYEERMARRLLGADSATVF
NIQEPEEETANQEYKVSSCEQRLISEIEYRLERSPVDESGDEVQYGDVPVENGMAPFF
EMKLKHYKIFEGMPVTFTCRVAGNPKPKIYWFKDGKQISPKSDHYTIQRDLDGTCSLH
TTASTLDDDGNYTIMAANPQGRISCTGRLMVQAVNQRGRSPRSPSGHPHVRRPRSRSR
DSGDENEPIQERFFRPHFLQAPGDLTVQEGKLCRMDCKVSGLPTPDLSWQLDGKPVRP
DSAHKMLVRENGVHSLIIEPVTSRDAGIYTCIATNRAGQNSFSLELVVĀAKEAHKPPV
FIEKLQNTGVADGYPVRLECRVLGVPPPQIFWKKENESLTHSTDRVSMHQDNHGYICL
LIQGATKEDAGWYTVSAKNEAGIVSCTARLDVYTQWHQQSQSTKPKKVRPSASRYAAL
SDQGLDIKAAFQPEANPSHLTLNTALVESEDL (SEQ ID NO:99)

FIG. 12

NP_057165.3 palladin amino acid sequence

```
   1 msgtsshesf ydslsdmqee skntdffpgl saflsqeein keldlarrai adsetedfds
  61 ekeisqifst spaslcehps hketklgeha srrpqdnrst pvqplaekqt ksisspvskr
 121 kpamsplltr psyirslrka ekrgaktpst nvkpktphqr kggpqsqlcd kaanlieelt
 181 sifkaakprn rspngesssp dsgylspknq psallsasas qspmedqgem erevkspgar
 241 hcyqdnqdla vphnrkshpq phsalhfpaa prfiqklrsq evaegsrvyl ecrvtgnptp
 301 rvrwfcegke lhntpdiqih ceggdlhtli iaeafeddtg rytclatnps gsdttsaevf
 361 iegasstdsd seslafksra gampqaqkkt tsvsltigss spktgvttav iqplsvpvqq
 421 vhsptsylcr pdgtttayfp pvftkelqnt avaegqvvvl ecrvrgappl qvqwfrqgse
 481 iqdspdfril qkkprstaep eeictlviae tfpedagift csarndygsa tstaqlvvts
 541 antencsyes mgesnndhfq hfpppppile tsslelaskk pseiqqvnnp elglsraalq
 601 mqfnaaeret ngvhpsrgvn glingkansn kslptpavll sptkeppppll akpklgfpkk
 661 asrtariasd eeiqgtkdav iqdlerklrf kedllnngqp rltyeermar rllgadsatv
 721 fniqepeeet anqeykvssc eqrliseiey rlerspvdes gdevqygdvp vengmapffe
 781 mklkhykife gmpvtftcrv agnpkpkiyw fkdgkqispk sdhytiqrdl dgtcslhtta
 841 stldddgnyt imaanpqgri sctgrlmvqa vnqrgrsprs psghphvrrp rsrsrdsgde
 901 nepiqerffr phflqapgdl tvqegklcrm dckvsglptp dlswqldgkp vrpdsahkml
 961 vrengvhsli iepvtsrdag iytciatnra gqnsfslelv vaakeahkpp vfieklqntg
1021 vadgypvrle crvlgvpppq ifwkkenesl thstdrvsmh qdnhgyicll iqgatkedag
1081 wytvsaknea givsctarld vyisrh (SEQ ID NO:87)
```

FIG. 13A

NM_016081
Palladin mRNA

```
   1 gtgaccacgg accaggcagt ctctaatgaa taggcaaggc cacaacctcc attctcccag
  61 aaaagaagaa atgctcatct gaaattcatc accctctctg agtcttcaaa ctgaccaagc
 121 attgaaaaga acacagtttc agaaaacagt tccagtgcc tctggccttc ctactgaaag
 181 cagacacaga gtgcatgaag accgttcaaa tatgtcaggg acctcctcc atgagtcctt
 241 ctatgactcc ctctcagaca tgcaggaaga aagcaagaat actgacttct tcccgggcct
 301 ttctgctttc ctcagccagg aagagataaa caagagtctt gacctggccc ggagagccat
 361 agccgactcc gaaacagaag attttgactc ggaaaaggag atctcgcaga ttttcagtac
 421 ttctcctgca agcctctgtg aacatcctc ccataaggag accaaattgg gtgaacacgc
 481 ctcgaggaga cctcaggata caggtcaac acctgtccag cctctggcag agaaacaaac
 541 taagagtatc tcttcacctg tttcaaagag gaaacctgcc atgtcacccc tgctcaccag
 601 gcccagctac atccggagcc tccgaaaggc tgaaaagcgt ggtgcaaaaa ctcccagcac
 661 aaacgtaaag cccaaaacgc cacatcaaag aaagggtggc cccagagcc agctgtgtga
 721 caaggcagct aatttaattg aggagctaaa atccatattt aaagccgcaa agcaagaaa
 781 cagaagccca aatggggagt cctcgtcacc agacagtggg tacctgtctc taaaaatca
 841 gccgtcagcc ctgctgagtg cctcagccag ccagagccct atggaagacc aaggggagat
 901 ggaaagagag gtcaagtccc ctggggccag gcattgctac caggacaacc aggacttggc
 961 agtgccacac aaccgcaagt ctcaccaaca gccccacagc gccctccact cccagctgc
1021 acctcgattc atccaaaagc tgaggagcca agaagtagca gaagggagcc gagtttatct
1081 ggagtgtaga gtcactggaa accccactcc tcgagtcaga tggttctgtg aagggaaaga
1141 actgcacaac actcctgata ttcaaatcca ctgtgacggg gggactccc atacccctgat
1201 catagcagag gcctttgagg acgacacagg tcgctacacc tgtttggcta cgaatccag
1261 cggctcagac acaacatctg ctgaggtgtt cattgaaggt gccagttcaa cagattctga
1321 cagtgaaagt ttagctttca aatcaagagc tggagctatg ccacaagctc aaaagaaaac
1381 aacttctgtt tccttgacaa taggatcatc atctccaaag acagggtga ccacagctgt
1441 gattcaacca ctgtctgtcc ctgtgcaaca ggttcacagt ccaacttcat atctctgccg
1501 acctgatgga accactactg cctactttcc tcctgttttt acaaaggaac tgcaaaacac
1561 agccgctggcg gaaggccagg tggtggttct ggagtgggcgg gtccgtgggg caccccctct
1621 gcaggtccag tggtttcggc aagggagtga aatccaagac tctccagatt tccgaattct
1681 acagaaaaaa cctagatcta cagctgaacc tgaggagatt tgcaccctag ttatcgctga
1741 gactttccct gaagatgcag ggatctttac atgttcagca gaaatgatt atggatcagc
1801 aaccagcact gccagctgg ttgtcacctc agccaacact gaaaactgta gttacgagtc
1861 aatgggagaa tccaacaatg accacttcca acactttcca cctccccctc caatcttgga
1921 gacaagttcc ttggagttgg cttcaaagaa accatctgag atccagcagg tgaacaaccc
1981 tgagttaggc ctgagcaggg cagcccttca aatgcaattc aatgctgctg agaaggaaac
2041 gaacggagtc catcccagcc gtggagtaaa tggactgatt aacggcaaag ctaacagtaa
2101 taaatctctt ccaacaccag ctgtcctgct ttcaccccact aaggagccac cacctctgct
2161 tgccaaacca aaactaggat tccaaagaa ggccagtaga actgctagaa tagcctccga
2221 tgaggaaatt caaggcacaa aggatgctgt tattcaagac ctggaacgaa aacttcgctt
2281 caaggaggac ctcctgaaca atggccagcc gaggttaaca tacgaagaaa gaatggctcg
2341 tcgactgcta ggtgctgaca gtgcaactgt ctttaatatt caggagccag aagaggaaac
2401 agctaatcag gaatacaaag tctccagctg tgaacagta ctcatcagtg aaatagagta
2461 caggctagaa aggtctcctg tggatgaatc aggtgatgaa gttcagtatg gagatgtgcc
2521 tgtggaaaat ggaatggcac cattcttga atgaagctg aaacattaca agatctttga
2581 gggaatgcca gtaactttca catgtagagt ggctggaaat ccaaagccaa agatctattg
2641 gtttaaagat gggaagcaga tctctccaaa gagtgatcac tacaccattc aaagagatct
2701 cgatgggacc tgctccctcc ataccacagc ctccacccta gatgatgatg ggaattatac
2761 aattatggct gcaaccctc agggccgcat cagttgtact ggacggctaa tgtacaggc
2821 tgtcaaccaa agaggtcgaa gtcccccggtc tcctcaggc catcctcatg tcagaaggcc
2881 tcgttctaga tcaagggaca gtgagacga aaatgaacca attcaggagc gattcttcag
2941 acctcacttc ttgcaggctc ctggagatct gactgttcaa gaaggaaaac tctgcagaat
3001 ggactgcaaa gtcagtgggt accaacccc agatctaagc tgcaactag atggaaagcc
3061 cgtacgccct gacagtgctc acaagatgct ggtgctgag aacgggtgc actctctgat
3121 catagagcca gtcacgtcac gtgatgccgg catctacaca tgtatagcta ccaaccgagc
3181 aggacagaac tcattcagcc tggagcttgt ggttgctgct aagaagcac acaaacccc
3241 tgtgtttatt gagaagctcc aaaacacagg agttgctgat gggtaccag tgcggctgga
3301 atgtcgtgta ttgggagtgc caccacctca gatattttgg aagaaagaaa atgaatcact
```

FIG. 13B

```
3361 cactcacagc actgaccgag tgagcatgca ccaggacaac cacggctaca tctgcctgct
3421 cattcaggga gccacaaaag aagatgctgg gtggtatact gtgtcagcca agaatgaagc
3481 agggattgtg tcctgtactg ccaggctgga cgtttacatt tctcgacatt aatagtgaac
3541 cacaccagga gaacaaatac ccaacccagt ggcatcagca gtcacagagc accaagccaa
3601 aaaaagtacg gccctcagcc agtcgctatg cagcactttc ggaccaggga ctagacatca
3661 aagcagcgtt ccaacctgag gccaacccat ctcacctgac actgaatact gccttggtag
3721 aaagtgagga cctgtaatcc agcattcttg ttaaagctga aacactgaaa cagccattgc
3781 cttgaccaac atattccttt gtcacattat gtaaaaggca gaaacatacc tttgactata
3841 agaaattaaa aaaaaaacac caaaataata tttttcttac ttgatatacc aaacttagtt
3901 taagtagata atgctaatac aaatatacac attgcacaga aaatacacat ttactgtcca
3961 atttaaaact ttggaattgc tgtgattaaa gtgatcaaaa tgccaaaata ctaaaggaaa
4021 tcaattgttc acaggtaact acaatttgta ttatctacaa gtgcctttaa acacaagata
4081 taggtgctgt gtagcctgat agtgtgaaat gtttaatgag ggagttgtac cacaaacagt
4141 actacaatga ttctgaagca cagtgtattc agacagatac agtgaaccaa gtgcaatatg
4201 taaggatgaa agaagaagag atgacaaaga aatccaagta aatgccttgt ctttgcaaat
4261 gtttttatat taaatcataa ggaaggaact acttgcctta aatgttaata tcaaaagagt
4321 tttctaacaa ggttaatacc ttagttctta acatttttt tcttttatgtg tagtgttttc
4381 atgctaccctt ggtaggaaac ttatttacaa accatattaa aaggcteatt taaatataaa
4441 taatataaag tgctctgaat aaagcagaaa tatattacag ttcattccac agaaagcatc
4501 caaaccaccc aaatgaccaa ggcatatata gtatttggag gaatcagggg tttggaagga
4561 gtagggagga gaatgaagga aaatgcaacc agcatgatta tagtgtgttc atttagataa
4621 aagtagaagg cacaggagag gtagcaaagg ccaggctttt ctttggtttt cttcaaacat
4681 aggtgaaaaa aacactgcca ttcacaagtc aaggaaccca gggccagctg gaagtgtgga
4741 gcacacatgc tgtggagcac acatgctgtg gagattgcag tgtgtctgag gtttgtgtag
4801 tagtgaagaa ttttaggtat gtagagcaag ttgaaaatgg attgagactg catggtggca
4861 taaatgagaa attgcctgta gcatctagtc tacttgaagg aagtggagac ataaggagag
4921 acaaaaacag gtttgtgcca taaagtattt tttcaaagac accaagatgt ggtaaatgaa
4981 aattattagt tcacttccct gctgccatga aactttgcct taagaaggtg ctggattcca
5041 aggtttgtaa aggcatctcg gtaagactg cttttgaat gcatatgatt ttgcatcagc
5101 tagactgagt tgattctgac cagacttgat ggttttaagt cggaaccgat aaattttaaa
5161 aaggagaaaa aataaatttga cctagtagta taaaacatga ggcttaatg gtactttgct
5221 atgaaaagaa aacactgtat tccttatgca aaacacatgt atctttcatt atttataagt
5281 ggcctctctt agctcagtta ctcaattcat acgtagtatt ttttaaaata attttatatc
5341 tgtgtaccac cccatatatt tcatattact gtttcacatg tacagcttc tacttcttg
5401 taagaacacc aaccaaccaa ggtttaagtg attaataggc ttgagcaccg ggtggcagat
5461 gttctatgca gtgtggttca agtttctttg accgcactta tatgcattgc taatatggaa
5521 tttaagatac catacacagt ctctcatgga cctatctcte ttgtagaatt atgacttatg
5581 tcttacttgc caaatttttc tgaatgtgac cttttttgc tgatttgctg ggtttgggat
5641 taactagcat tattttgcca cctttatatt gtatttataa aaaaaaagt actatcaatc
5701 aatcatacta ctttggattg ttgtgctggt gtaatgtgga tttaacatca ataaatattt
5761 gacaaataat agttgcagtt ttgtgaagca aaataaatat tcagtttta (SEQ ID NO:20)
```

FIG. 14

GenBank AC080188; Homo sapiens BAC clone RP11-635L1

```
183421 agccacctct tgtactactg aaggaggaat ttatgcagac ttcttagcta ccagtgattt
183481 cactctgttt aatacaaaa atttacatgt atttctttta tgattaggt cagtgggtta
183541 ccaaccccag atctaagctg gcaactagat ggaaagcccg tacgccctga cagtgctcac
183601 aagatgctgg tgcgtgagaa cggggtgcac tctctgatca tagagccagt cacgtcacgt
183661 gatgccggca tctacacatg tatagctacc aaccgagcag gacagaactc attcagcctg
183721 gagcttgtgg ttgctgtgg gctcatctgt gaatcctgc tctctgacag aatgaacatc
183781 agacttacaa atgtaaacta atctacatt actaaccaat acggaaaata (SEQ ID NO:101)
```

FIG. 15

GenBank AC084353; Homo saplens BAC clone RP11-592K15

```
26881 tgcgtcagat gagagcagca caatcacctc ttctttaaca acttcacaca acacagggat
26941 tctcagaaga ctctgacagt gtgaaatcac ttgttgaact agtggcatct tcttatgttt
27001 ttcctctctt tcccctcct tagccaacac tgaaaactgt agttacgagt caatgggaga
27061 atccaacaat gaccacttcc aacactttcc acctccccct ccaatcttgg agacaagttc
27121 cttggagttg gcttcaaaga aaccatctga gatccagcag gtgaacaacc ctgagttagg
27181 cctgagcagg gcagccctttc aaatgcaatt caatgctgct gagaggggaaa cgaacgggagt
27241 ccatcccagc cgtggagtaa atggactgat taacggcaaa gctaacagta ataaatctct
27301 tccaacacca gctgtcctgc tttcacccac taaggagcca ccaccctctgc ttgccaaacc (SEQ ID NO:102)
```

FIG. 16

GenBank AC080188; Homo sapiens BAC clone RP11-635I1

```
139501 tgagagtgaa atgggcgagc atacttcact gacttagcgc ttggtccaga atgaactgct
139561 ggccccacac ttgggcctgc taacgtgtgc ccgttccctg ggtgttctct gcagctggcc
139621 taagtgccaa gcgatgtcca caagctgagc tcactcctgg aatacacgtt cctggccgtt
139681 ccatctctga aggtgtcact tctctttttc cccccaggga ccctctgaag ctcgcagcaa
139741 tccagaacca aatccgactg gagcaggagg ccggcgctcg gcagcccccg ccagccccgc
139801 gcagcgcgcc gccctcgcc cccttcccgc cgcgctcccg cgcgcctgcg cttcccgag ctgcggcct
139861 gcacgccgcc cgctcctc gagcccatga gccgctggc ctccgctcc gccccgcca
139921 tgcagtcctc cggctcctte aactacgcgc gccccaagca gttcatcgcc gcgcagaacc
139981 tcgggcccgc gtcgggccac ggcacgccgg cctccagccc cagctcgtcc agcctcccgt
140041 cgcccatgtc cccgacccg aggcagttcg gccgcgcccc cgtgccgcagc ttcgcgcagc
140101 cctcggcgc tgagcccgag gccccgtggg gctcctcctc gccgtcgcc cgccccccgc
140161 cacccccggt cttcagcccc acggctgcct tcccggtgcc cgacgtgttc ccactgccgc
140221 cgcccaccac gcccgcctccg agcccgggac aggcgtccca ctgctcgtcg cctgccaccc
140281 gcttggcca cagccagacg ccggcggcct tcctcagcgc tctgctgcc tgtcagccgg
140341 cgccgggcggc cgtcaacgcc ctggggctgc gcccctccg ccaaggggtgt caccccccgcg tgagtaaccg
140401 ccggcggtcct ccacttcccct gcccctcccg gcccgggtcgc ctgggactc ccacatctcc
140461 atacacgcgc tccatcagc ctgcaaccca gagcgcccca gtaacattt acacatttct
140521 ctccgtgcga tgtaaaaatt cttaacggca atttgactca gtgattcttg cgtagccact (SEQ ID NO:100)
```

FIG. 19

AAATGCTTTACTCTTCTCACCCTAAGGGCTCCTGAATTTAGCTTTTTATTACACAGAACC
CAGTAAACTAATTAATGGAAATCTAAAAATTATCCTTCCTCTTCTTAGAAAAGAAATATA
CTGCATGATGATTTGTGCTTTTCGATTTAATGTCACACAATCGTTTTTACACTGTATGTG
CTTTCCCTCCCCACAGCCCCAGTCCCAGCCCCAGTCTCGCAGTTCCATTCCTTCAGGGCA
GCTTCCATTCTACCGTGAGTTTTATTGCTTTCCCCTAAAACGCTGCCCTGGAGTCGCGT
TTATTGGACACTCTTTAGTCTGTAAAGGAAAAAAACACAAACACCGGAGGAGAATCATCC
TAACAAGCCGACAACATATCTATGGGCCTAAAAAACTTAAATTCTTTCCCGTTATTAGCA
CTTCTCGATCGTTCCAGGAAAGCCCGATTTGTAGCTTGGCTGCCCCAGGAAGGGGCCTGC
GACCAGAAAGATGCAAAGGGCGGGACAAGGTTACGAGTGGGTGCGGGGAAGCCTCCCTAA
CCTGGGGGCCGCGTCCCAGAGCTGCGAGCCACGCCTCCTCTCTCCGCCCGCCGCGCCGC
CGGACTCTTATTTTGAAGGGCGGCGGGTGAAGGCTCGGAGCCTCCTGAGTCACCCGG
CGGGCCGAGGTATAAAGCCCGATACCTGCCCCGCGCCCGGTCCGCGGA**GCCCGCTGCAG
C**TCCGCTCGCTCCGGACGCGGAATCGGGCAGCAGCGGGAGGCGGCCCGGAGAGCCGAGG
TAGGCGCGGGAATCGGCCCTGAGGCTGGTGGAAGAAATGTGTGAATTAAAGGGAGTGCA
GCGTGCAGGGTGGGCCGCGAGTCGGGAGTGCAGGGCTCGGGACAGGGTGGGGCGGGGAG
GACAAGAGACTCGTCAGCGCACTTTCCACCCGGCCGGTTCCTTCCCGAGCCCTCTCCCTC
CCCCGGCCCGCGGGAGCACAGATCCCTGAAAGCGGAGCTCCAGATAGGAATGTCTGCATC
ATCTTGGCAGGGCCCAGACGGGAGAAGATGCTCTGCTGCCACGGACGATCCCTCCCGCTC
TCCTAACTCTTCTCTGAACACCTCGCACCCCCACGGCCCCCCGCCCCTCTCTTAATCTTG
GCCACGCTCCCTGAGGGGTCAGACCTGGGGTGGGAGAGCAGAGAAAGCGGGGCTGGCAGA
GACAGGGGTGAGGGCCGGGAGAGGCGATGACATCATTCCCTGGCAGCTGGCGGGGAGAGG
GTGGGGACGGAGGGGTCCCCCCGACCTGAGCCGAGCCCTCCCTTCCCAAGCCCATCCTCC
TTTCTTTGGGATGGTTCACCCCACCTGGGCGCCATTCAAAGGAAGTTTGCGCGTAACTCG
GGGCGTCCTTTCCCCGGCCGGGTGCTGTGCCCGGCCCGCAGTCGGTGTTTCTTCTGGGCC
TGGGGGCGGCGTGGAGCCGGCGGCTCAGTCCCCTCAGTCCCAGGCCTTGGCAGCCGCTTT
GTTCACGCCGGGCGCGGGCCGAACCCGAACCTCAGCTGCAGCACTGGCAGCGCGCACCGG
CCACGCGTGGGTTCCCGGCCACGGCCGGGCCAACAAGGGAGGGTCCCGTGAGCAGCCAGG
CTGGCCCTCCCCGGGCCTGGGTGAGCTCCCAAAGCTGGAGCGCAGGGCTCTAGGCCGGCC
CCGCCCCGGGGCTGGGGCTTCCCGCCCGTTTGTCTCATTTTAACTTTTGGGGCAGCTC
TGTCCCGAATGGTGAGTGGTCCAGACTCTAGAAAGGGGTTTGGTCGCTTGAGCCCGGATT
GAGGCTTGGGACCTTTGCTCTCTTGCTGGGGACGGAAGGGGGCGCGCTGGGCAGGAGAGG
GGGCGTCTCGGTCGGTCTCCCTGGGCTCGGGCATCTTCCCACCCTGCGGAGCCGGGTCT
TGCGCTGCGTGCCCCGAACAGGCCCGGGCACACCGAGTCCCGTTACTGGTCTTCAGGCGA
AATTCCAGGACGGTGTGCATTCATCAACCTGGGAGTCTCTAGGAGCCAGAGATGACTGG
CTCTACATTTTAATGCGTAATCACAGAGAAACTAGCACGAGAAAAGGACAGAGGGACCGA
CCCAAGCTTCAGAGACATGGAATAATATGATCCTGGTTCATAAGCCTTGAAAAGCTCCCC
TCCGCCAGGTTAAGGAATGGTGTCACCAGCCTTGGCTGTGAGGATAATTTCTTGATTTGT
GTTATGCAGGCTCCTGTCAGGACTGTCTCCTTAACTCCACTACCTAAGGAAAAGATAGC
CAGAGAATTGTCCAGGGATTTGGGTTTGGGTTGCTTCTAGAAAGACAGCATCTTTCTTGC
TATTTTTTTTTCACATCCCCCCAAAACAATTTTTTTCCCCCTTCAGACTTGGCAGACTT
TGATTTAGATAAGAGGTTTGAGTTAATTTGATTTTCCCCATGTCTGTTTAGATCAATGGA
TATAGGAGATAGTTTGAAGCTAATGTACCCCTATGCCTTTGTGTGAGTGTAAGATTTATA
ACTTGAGGGAGGCAGTTAATAAATAGCACATCCTTGAACCATAAACATACGAGATAGACA
AGAGCTAGATAATAAACAGTTTTTCCCCCAATCCCTAAGCTTTACTTATTTTTTTTACTG
ATTCTTGTACTTTGTCATTAGAAAAGGAGTGGGGTTGGTTTCCCAGTGACCGCATTCAT
(SEQ ID NO:110)

SEQUENCE LISTING

```
<160> NUMBER OF SEQ ID NOS: 116

<210> SEQ ID NO 1
<211> LENGTH: 4347
<212> TYPE: DNA
<213> ORGANISM: H. sapiens

<400> SEQUENCE: 1
cctgagtcac ccggcgggcg aggtataaag cccgatacct gccccgcgcc cggtccgcgg      60
agcccgctgc agctcccgct cgctccggac gcggaatcgg gcagcagcgg gaggcggccc     120
ggagagccga gggaccctct gaagctccag caactccaga accaaatccg actggagcag     180
gaggccggcg ctcggcagcc tccgccagcc ccgcgcagcg cgccgccctc gcccccttc     240 ccgccgccgc ccgccttccc cgagctcgcg gcctgcacgc cgcccgcgtc cccggagccc     300
atgagcgcgc tggcctcccg ctccgccccc gccatgcagt cctccggctc cttcaactac     360
gcgcgcccca agcagttcat cgccgcgcag aacctcgggc ccgcgtcggg ccacggcacg     420
ccggcctcca gccccagctc gtccagcctc ccgtcgccca tgtccccgac gccgaggcag     480
ttcggccgcg ccccgtgcc gcccttcgcg cagcccttcg gcgctgagcc cgaggccccg     540 tgggctcct cctcgccgtc gccccgccc ccgccaccc cggtcttcag ccccacggct     600 gccttccgg tgcccgacgt gttcccactg ccgccgccac caccgccgct cccgagcccg     660
ggacaggcgt cccactgctc gtcgcctgcc acccgcttcg gccacggcca gacgcccgcg     720
gccttcctca gcgctctgct gccctcgcag ccgccgccgg cggccgtcaa cgccctgggg     780
ctgcccaagg gtgtcacccc cgcaggattt ccaaagaagg ccagtagaac tgctagaata     840
gcctccgatg aggaaattca aggcacaaag gatgctgtta ttcaagacct ggaacgaaaa     900
cttcgcttca aggaggacct cctgaacaat ggccagccga ggttaacata cgaagaaga     960 atggctcgtc gactgctagg tgctgacagt gcaactgtct ttaatattca ggagccagaa    1020
gaggaaacag ctaatcagga atacaaagtc tccagctgtg aacagagact catcagtgaa    1080
atagagtaca ggctagaaag gtctcctgtg gatgaatcag gtgatgaagt tcagtatgga    1140
gatgtgcctg tggaaaatgg aatggcacca tttttttgaga tgaagctgaa acattacaag    1200
atctttgagg gaatgccagt aactttcaca tgtagagtgg ctggaaatcc aaagccaaag    1260
atctattggt ttaaagatgg gaagcagatc tctccaaaga gtgatcacta caccattcaa    1320
agagatctcg atgggacctg ctccctccat accacagcct ccaccctaga tgatgatggg    1380
aattatacaa ttatggctgc aaaccctcag ggccgcatca gttgtactgg acggctaatg    1440
gtacaggctg tcaaccaaag aggtcgaagt ccccggtctc cctcaggcca tcctcatgtc    1500
agaaggcctc gttctagatc aagggacagt gggagacgaa atgaaccaat tcaggagcga    1560
ttcttcagac ctcacttctt gcaggctcct ggagatctga ctgttcaaga aggaaaactc    1620
tgcagaatgg actgcaaagt cagtgggtta ccaacccag atctaagctg gcaactagat    1680
```

```
ggaaagcccg tacgccctga cagtgctcac aagatgctgg tgcgtgagaa cggggtgcac    1740
tctctgatca tagagccagt cacgtcacgt gatgccggca tctacacatg tatagctacc    1800
aaccgagcag gacagaactc attcagcctg gagcttgtgg ttgctgctaa agaagcacac    1860
aaaccccctg tgtttattga gaagctccaa aacacaggag ttgctgatgg gtacccagtg    1920
cggctggaat gtcgtgtatt gggagtgcca ccacctcaga tattttggaa gaaagaaaat    1980
gaatcactca ctcacagcac tgaccgagtg agcatgcacc aggacaacca cggctacatc    2040
tgcctgctca ttcagggagc cacaaaagaa gatgctgggt ggtatactgt gtcagccaag    2100
aatgaagcag ggattgtgtc ctgtactgcc aggctggacg tttacacccca gtggcatcag    2160 cagtcacaga gcaccaagcc aaaaaaagta cggccctcag ccagtcgcta tgcagcactt    2220
tcggaccagg gactagacat caaagcagcg ttccaacctg aggccaaccc atctcacctg    2280
acactgaata ctgccttggt agaaagtgag gacctgtaat ccagcattct tgttaaagct    2340
gaaacactga acagccatt gccttgacca acatattcct ttgtcacatt atgtaaaagg    2400
cagaaacata cctttgacta taagaaatta aaaaaaaaca ccaaaataat attttttctta    2460 cttgatatac caaacttagt ttaagtagat aatgctaata caaatataca cattgcacag    2520
aaaatacaca tttactgtcc aatttaaaac tttggaattg ctgtgattaa agtgatcaaa    2580
atgccaaaat actaaaggaa atcaattgtt cacaggtaac tacaatttgt attatctaca    2640
agtgccttta aacacaagat ataggtgctg tgtagcctga tagtgtgaaa tgtttaatga    2700
gggagttgta ccacaaacag tactacaatg attctgaagc acagtgtatt cagacagata    2760
cagtgaacca agtgcaatat gtaaggatga aagaagaaga gatgacaaag aaatccaagt    2820
aaatgccttg tctttgcaaa tgttttata ttaaatcata aggaaggaac tacttgcctt    2880
aaatgttaat atcaaaagag ttttctaaca aggttaatac cttagttctt aacatttttt    2940
ttctttatgt gtagtgtttt catgctacct tggtaggaaa cttatttaca aaccatatta    3000
aaaggctaat ttaaatataa ataatataaa gtgctctgaa taaagcagaa atatattaca    3060
gttcattcca cagaaagcat ccaaaccacc caaatgacca aggcatatat agtatttgga    3120
ggaatcaggg gtttggaagg agtagggagg agaatgaagg aaaatgcaac cagcatgatt    3180
atagtgtgtt caattagata aaagtagaag gcacaggaga ggtagcaaag gccaggcttt    3240
tctttggttt tcttcaaaca taggtgaaaa aaacactgcc attcacaagt caaggaaccc    3300
agggccagct ggaagtgtgg agcacacatg ctgtggagca cacatgctgt ggagattgca    3360
gtgtgtctga ggtttgtgta gtagtggaag attttaggta tgtagagcaa gttgaaaatg    3420
gattgagact gcatggtggc ataaatgaga aattgcctgt agcatctagt ctacttgaag    3480
gaagtggaga cataaggaga gacaaaaaca ggtttgtgcc ataaagtatt ttttcaaaga    3540
caccaagatg tggtaaatga aaattattag ttcacttccc tgctgccatg aaactttgcc    3600
ttaagaaggt gctggattcc aaggtttgta aaggcatctc ggtaaagact gcttttttgaa    3660 tgcatatgat tttgcatcag ctagactgag ttgattctga ccagacttga tggttttaag    3720
tcggaaccga taaattttaa aaaggagaaa aaataatttg acctagtagt ataaaacatg    3780 aggcttaat ggtactttgc tatgaaaaga aaacactgta ttccttatgc aaaacacatg    3840
tatctttcat tatttataag tggcctctct tagctcagtt actcaattca tacgtagtat    3900
tttttaaaat aattttatat ctgtgtacca ccccatatat ttcatattac tgtttcacat    3960
gtacagcttt ctacttcttt gtaagaacac caaccaacca aggtttaagt gattaatagg    4020
cttgagcacc gggtggcaga tgttctatgc agtgtggttc aagtttcttt gaccgcactt    4080
```

| atatgcattg ctaatatgga atttaagata ccatacacag tctctcatgg acctatctct | 4140 |
| attgtagaat tatgacttat gtcttacttg gcaaattttt ctgaatgtga ccttttttttg | 4200 |
| ctgatttgct gggtttggga ttaactagca ttattttgcc acctttatat tgtatttata | 4260 |
| aaaaaaaagt actatcaatc aatcatacta ctttggattg ttgtgctggt gtaatgtgga | 4320 |
| tttaacatca ataaatattt gacaaat | 4347 |

<210> SEQ ID NO 2
<211> LENGTH: 10
<212> TYPE: DNA
<213> ORGANISM: H. sapiens

<400> SEQUENCE: 2

| gacgcccgcg | 10 |

<210> SEQ ID NO 3
<211> LENGTH: 10
<212> TYPE: DNA
<213> ORGANISM: H. sapiens

<400> SEQUENCE: 3

| gacgtccgcg | 10 |

<210> SEQ ID NO 4
<211> LENGTH: 30
<212> TYPE: DNA
<213> ORGANISM: H. sapiens

<400> SEQUENCE: 4

| gccacggcca gacgcccgcg gccttcctca | 30 |

<210> SEQ ID NO 5
<211> LENGTH: 30
<212> TYPE: DNA
<213> ORGANISM: H. sapiens

<400> SEQUENCE: 5

| gccacggcca gacgtccgcg gccttcctca | 30 |

<210> SEQ ID NO 6
<211> LENGTH: 672
<212> TYPE: DNA
<213> ORGANISM: H. sapiens

<400> SEQUENCE: 6

| ggaccctctg aagctccagc aactccagaa ccaaatccga ctggagcagg aggccggcgc | 60 |
| tcggcagcct ccgccagccc cgcgcagcgc gccgccctcg ccccccttcc cgccgccgcc | 120 |
| cgccttcccc gagctcgcgg cctgcacgcc gcccgcgtcc ccggagccca tgagcgcgct | 180 |
| ggcctcccgc tccgccccg ccatgcagtc ctccggctcc ttcaactacg cgcgcccaa | 240 |
| gcagttcatc gccgcgcaga acctcgggcc cgcgtcgggc cacggcacgc cggcctccag | 300 |
| cccccagctcg tccagcctcc cgtcgcccat gtccccgacg ccgaggcagt tcggccgcgc | 360 |
| ccccgtgccg cccttcgcgc agcccttcgg cgctgagccc gaggcccgt ggggctcctc | 420 |
| ctcgccgtcg ccccgcccc cgccacccc ggtcttcagc ccacggctg ccttcccggt | 480 |
| gcccgacgtg ttcccactgc cgccgccacc accgccgctc ccgagcccgg acaggcgtc | 540 |
| ccactgctcg tcgcctgcca cccgcttcgg ccacggccag acgtccgcgg ccttcctcag | 600 |

```
cgctctgctg ccctcgcagc cgccgccggc ggccgtcaac gccctggggc tgcccaaggg    660
tgtcaccccc gc                                                         672

<210> SEQ ID NO 7
<211> LENGTH: 140
<212> TYPE: DNA
<213> ORGANISM: H. sapiens

<400> SEQUENCE: 7
caccgccgct cccgagcccg ggacaggcgt cccactgctc gtcgcctgcc acccgcttcg     60
gccacggcca gacgtccgcg gccttcctca gcgctctgct gccctcgcag ccgccgccgg    120
cggccgtcaa cgccctgggg                                                140

<210> SEQ ID NO 8
<211> LENGTH: 110
<212> TYPE: DNA
<213> ORGANISM: H. sapiens

<400> SEQUENCE: 8
gccttcccgg tgcccgacgt gttcccactg ccgccgccac caccgccgct cccgagcccg     60
ggacaggcgt cccactgctc gtcgcctgcc acccgcttcg gccacggcca                110

<210> SEQ ID NO 9
<211> LENGTH: 120
<212> TYPE: DNA
<213> ORGANISM: H. sapiens

<400> SEQUENCE: 9
tggggctcct cctcgccgtc gccccgccc ccgccacccc cggtcttcag ccccacggct      60
gccttcccgg tgcccgacgt gttcccactg ccgccgccac caccgccgct cccgagcccg    120

<210> SEQ ID NO 10
<211> LENGTH: 120
<212> TYPE: DNA
<213> ORGANISM: H. sapiens

<400> SEQUENCE: 10
ggacaggcgt cccactgctc gtcgcctgcc acccgcttcg gccacggcca gacgtccgcg     60
gccttcctca gcgctctgct gccctcgcag ccgccgccgg cggccgtcaa cgccctgggg    120

<210> SEQ ID NO 11
<211> LENGTH: 672
<212> TYPE: DNA
<213> ORGANISM: H. sapiens

<400> SEQUENCE: 11
ggaccctctg aagctccagc aactccagaa ccaaatccga ctggagcagg aggccggcgc     60
tcggcagcct ccgccagccc cgcgcagcgc gccgccctcg ccccccttcc cgccgccgcc    120
cgccttcccc gagctcgcgg cctgcacgcc gcccgcgtcc ccggagccca tgagcgcgct    180
ggcctcccgc tccgcccccg ccatgcagtc ctccggctcc ttcaactacg cgcgcccaa     240 gcagttcatc gccgcgcaga acctcgggcc gcgtcgggc cacggcacgc cggcctccag    300
ccccagctcg tccagcctcc cgtcgcccat gtccccgacg ccgaggcagt tcggccgcgc    360
ccccgtgccg cccttcgcgc agccttcgg cgctgagccc gaggcccgt ggggctcctc     420 ctcgccgtcg ccccgcccc cgccacccc ggtcttcagc cccacggctg ccttcccggt     480
gcccgacgtg ttcccactgc cgccgccacc accgccgctc ccgagcccgg gacaggcgtc    540
```

```
ccactgctcg tcgcctgcca cccgcttcgg ccacggccag acgcccgcgg ccttcctcag    600
cgctctgctg ccctcgcagc cgccgccggc ggccgtcaac gccctggggc tgcccaaggg    660
tgtcaccccc gc                                                        672
```

<210> SEQ ID NO 12
<211> LENGTH: 20
<212> TYPE: DNA
<213> ORGANISM: H. sapiens

<400> SEQUENCE: 12

```
atctaagctg gcaactagat                                                 20
```

<210> SEQ ID NO 13
<211> LENGTH: 20
<212> TYPE: DNA
<213> ORGANISM: H. sapiens

<400> SEQUENCE: 13

```
atctaagctg tcaactagat                                                 20
```

<210> SEQ ID NO 14
<211> LENGTH: 40
<212> TYPE: DNA
<213> ORGANISM: H. sapiens

<400> SEQUENCE: 14

```
ccaaccccag atctaagctg gcaactagat ggaaagcccg                           40
```

<210> SEQ ID NO 15
<211> LENGTH: 40
<212> TYPE: DNA
<213> ORGANISM: H. sapiens

<400> SEQUENCE: 15

```
ccaaccccag atctaagctg tcaactagat ggaaagcccg                           40
```

<210> SEQ ID NO 16
<211> LENGTH: 208
<212> TYPE: DNA
<213> ORGANISM: H. sapiens

<400> SEQUENCE: 16

```
gtcagtgggt taccaacccc agatctaagc tggcaactag atggaaagcc cgtacgccct    60
gacagtgctc acaagatgct ggtgcgtgag aacggggtgc actctctgat catagagcca   120
gtcacgtcac gtgatgccgg catctacaca tgtatagcta ccaaccgagc aggacagaac   180
tcattcagcc tggagcttgt ggttgctg                                      208
```

<210> SEQ ID NO 17
<211> LENGTH: 208
<212> TYPE: DNA
<213> ORGANISM: H. sapiens

<400> SEQUENCE: 17

```
gtcagtgggt taccaacccc agatctaagc tgtcaactag atggaaagcc cgtacgccct    60
gacagtgctc acaagatgct ggtgcgtgag aacggggtgc actctctgat catagagcca   120
gtcacgtcac gtgatgccgg catctacaca tgtatagcta ccaaccgagc aggacagaac   180
tcattcagcc tggagcttgt ggttgctg                                      208
```

<210> SEQ ID NO 18
<211> LENGTH: 122
<212> TYPE: DNA
<213> ORGANISM: H. sapiens

<400> SEQUENCE: 18

| | |
|---|---:|
| gtcagtgggt taccaacccc agatctaagc tggcaactag atggaaagcc cgtacgccct | 60 |
| gacagtgctc acaagatgct ggtgcgtgag aacggggtgc actctctgat catagagcca | 120 |
| gt | 122 |

<210> SEQ ID NO 19
<211> LENGTH: 122
<212> TYPE: DNA
<213> ORGANISM: H. sapiens

<400> SEQUENCE: 19

| | |
|---|---:|
| gtcagtgggt taccaacccc agatctaagc tgtcaactag atggaaagcc cgtacgccct | 60 |
| gacagtgctc acaagatgct ggtgcgtgag aacggggtgc actctctgat catagagcca | 120 |
| gt | 122 |

<210> SEQ ID NO 20
<211> LENGTH: 5809
<212> TYPE: DNA
<213> ORGANISM: H. sapiens

<400> SEQUENCE: 20

| | |
|---|---:|
| gtgaccacgg accaggcagt ctctaatgaa taggcaaggc cacaacctcc attctcccag | 60 |
| aaaagaagaa atgctcatct gaaattcatc acctctctgg agtcttcaaa ctgaccaagc | 120 |
| attgaaaaga acacagtttc agaaaacagt ttccagtgcc tctggccttc ctactgaaag | 180 |
| cagacacaga gtgcatgaag accgttcaaa tatgtcaggg acctcctccc atgagtcctt | 240 |
| ctatgactcc ctctcagaca tgcaggaaga agcaagaat actgacttct tcccgggcct | 300 |
| ttctgctttc ctcagccagg aagagataaa caagagtctt gacctggccc ggagagccat | 360 |
| agccgactcc gaaacagaag attttgactc ggaaaaggag atctcgcaga ttttcagtac | 420 |
| ttctcctgca agcctctgtg aacatccttc ccataaggag accaaattgg gtgaacacgc | 480 |
| ctcgaggaga cctcaggata caggtcaac acctgtccag cctctggcag agaaacaaac | 540 |
| taagagtatc tcttcacctg tttcaaagag gaaacctgcc atgtcacccc tgctcaccag | 600 |
| gcccagctac atccggagcc tccgaaaggc tgaaaagcgt ggtgcaaaaa ctcccagcac | 660 |
| aaacgtaaag cccaaaacgc cacatcaaag aaagggtggc ccccagagcc agctgtgtga | 720 |
| caaggcagct aatttaattg aggagctaac atccatatt aaagccgcaa agccaagaaa | 780 |
| cagaagccca aatggggagt cctcgtcacc agacagtggg tacctgtctc ctaaaaatca | 840 |
| gccgtcagcc ctgctgagtg cctcagccag ccagagccct atggaagacc aaggggagat | 900 |
| ggaaagagag gtcaagtccc ctggggccag gcattgctac caggacaacc aggacttggc | 960 |
| agtgccacac aaccgcaagt ctcacccaca gccccacagc gccctccact tcccagctgc | 1020 |
| acctcgattc atccaaaagc tgaggagcca agaagtagca gaagggagcc gagtttatct | 1080 |
| ggagtgtaga gtcactggaa accccactcc tcgagtcaga tggttctgtg aagggaaaga | 1140 |
| actgcacaac actcctgata ttcaaatcca ctgtgaggga gggaccctcc atacctgat | 1200 |
| catagcagag gcctttgagg acgacacagg tcgctcacc tgtttggcta cgaatcccag | 1260 |
| cggctcagac acaacatctg ctgaggtgtt cattgaaggt gccagttcaa cagattctga | 1320 |

```
cagtgaaagt ttagctttca aatcaagagc tggagctatg ccacaagctc aaaagaaaac   1380
aacttctgtt tccttgacaa taggatcatc atctccaaag acaggggtga ccacagctgt   1440
gattcaacca ctgtctgtcc ctgtgcaaca ggttcacagt ccaacttcat atctctgccg   1500
acctgatgga accactactg cctactttcc tcctgttttt acaaaggaac tgcaaaacac   1560
agccgtggcg aaggccagg tggtggttct ggagtgccgg gtccgtgggg cacccctct    1620 gcaggtccag tggtttcggc aagggagtga atccaagac tctccagatt ccgaattct    1680 acagaaaaaa cctagatcta cagctgaacc tgaggagatt tgcaccctag ttatcgctga   1740
gactttccct gaagatgcag ggatctttac atgttcagca agaaatgatt atggatcagc   1800
aaccagcact gcccagctgg ttgtcacctc agccaacact gaaaactgta gttacgagtc   1860
aatgggagaa tccaacaatg accacttcca acactttcca cctcccccte caatcttgga   1920 gacaagttcc ttggagttgg cttcaaagaa accatctgag atccagcagg tgaacaaccc   1980
tgagttaggc ctgagcaggg cagcccttca aatgcaattc aatgctgctg agagggaaac   2040
gaacggagtc catcccagcc gtggagtaaa tggactgatt aacggcaaag ctaacagtaa   2100
taaatctctt ccaacaccag ctgtcctgct ttcacccact aaggagccac cacctctgct   2160
tgccaaacca aaactaggat ttccaaagaa ggccagtaga actgctagaa tagcctccga   2220
tgaggaaatt caaggcacaa aggatgctgt tattcaagac ctggaacgaa aacttcgctt   2280
caaggaggac ctcctgaaca atggccagcc gaggttaaca tacgaagaaa gaatggctcg   2340
tcgactgcta ggtgctgaca gtgcaactgt ctttaatatt caggagccag aagaggaaac   2400
agctaatcag gaatacaaag tctccagctg tgaacagaga ctcatcagtg aaatagagta   2460
caggctagaa aggtctcctg tggatgaatc aggtgatgaa gttcagtatg agatgtgcc    2520 tgtggaaaat ggaatggcac cattctttga tgaagctg aaacattaca agatctttga    2580
gggaatgcca gtaactttca catgtagagt ggctggaaat ccaaagccaa agatctattg   2640
gtttaaagat gggaagcaga tctctccaaa gagtgatcac tacaccattc aaagagatct   2700
cgatgggacc tgctccctcc ataccacagc ctccaccta gatgatgatg gaattatac    2760 aattatggct gcaaaccctc agggccgcat cagttgtact ggacggctaa tggtacaggc   2820
tgtcaaccaa agaggtcgaa gtccccggtc tccctcaggc catcctcatg tcagaaggcc   2880
tcgttctaga tcaagggaca gtggagacga aaatgaacca attcaggagc gattcttcag   2940
acctcacttc ttgcaggctc ctggagatct gactgttcaa gaaggaaaac tctgcagaat   3000
ggactgcaaa gtcagtgggt taccaacccc agatctaagc tggcaactag atggaaagcc   3060
cgtacgccct gacagtgctc acaagatgct ggtgcgtgag aacggggtgc actctctgat   3120
catagagcca gtcacgtcac gtgatgccgg catctacaca tgtatagcta ccaaccgagc   3180
aggacagaac tcattcagcc tggagcttgt ggttgctgct aaagaagcac acaaccccc    3240 tgtgtttatt gagaagctcc aaaacacagg agttgctgat gggtacccag tgcggctgga   3300
atgtcgtgta ttgggagtgc caccacctca gatattttgg aagaaagaaa atgaatcact   3360
cactcacagc actgaccgag tgagcatgca ccaggacaac cacggctaca tctgcctgct   3420
cattcaggga gccacaaaag aagatgctgg gtggtatact gtgtcagcca agaatgaagc   3480
agggattgtg tcctgtactg ccaggctgga cgtttacatt tctcgacatt aatagtgaac   3540
cacaccagga gaacaaatac ccaacccagt ggcatcagca gtcacagagc accaagccaa   3600
aaaaagtacg gccctcagcc agtcgctatg cagcactttc ggaccaggga ctagacatca   3660
```

```
aagcagcgtt ccaacctgag gccaacccat ctcacctgac actgaatact gccttggtag    3720
aaagtgagga cctgtaatcc agcattcttg ttaaagctga acactgaaa cagccattgc    3780 cttgaccaac atattccttt gtcacattat gtaaaaggca gaaacatacc tttgactata    3840
agaaattaaa aaaaaaacac caaaataata tttttcttac ttgatatacc aaacttagtt    3900
taagtagata atgctaatac aaatatacac attgcacaga aaatacacat ttactgtcca    3960
atttaaaact ttggaattgc tgtgattaaa gtgatcaaaa tgccaaaata ctaaaggaaa    4020
tcaattgttc acaggtaact acaatttgta ttatctacaa gtgcctttaa acacaagata    4080
taggtgctgt gtagcctgat agtgtgaaat gtttaatgag ggagttgtac cacaaacagt    4140
actacaatga ttctgaagca cagtgtattc agacagatac agtgaaccaa gtgcaatatg    4200
taaggatgaa agaagaagag atgacaaaga atccaagta aatgccttgt ctttgcaaat    4260
gtttttatat taaatcataa ggaaggaact acttgcctta aatgttaata tcaaaagagt    4320
tttctaacaa ggttaatacc ttagttctta acatttttt tctttatgtg tagtgttttc    4380
atgctacctt ggtaggaaac ttatttacaa accatattaa aaggctaatt taaatataaa    4440
taatataaag tgctctgaat aaagcagaaa tatattacag ttcattccac agaaagcatc    4500
caaaccaccc aaatgaccaa ggcatatata gtatttggag gaatcagggg tttggaagga    4560
gtagggagga gaatgaagga aaatgcaacc agcatgatta tagtgtgttc atttagataa    4620
aagtagaagg cacaggagag gtagcaaagg ccaggcttt cttggtttt ttcaaacat    4680 aggtgaaaaa aacactgcca ttcacaagtc aaggaaccca gggccagctg gaagtgtgga    4740
gcacacatgc tgtggagcac acatgctgtg gagattgcag tgtgtctgag gtttgtgtag    4800
tagtggaaga ttttaggtat gtagagcaag ttgaaaatgg attgagactg catggtggca    4860
taaatgagaa attgcctgta gcatctagtc tacttgaagg aagtggagac ataaggagag    4920
acaaaaacag gtttgtgcca taaagtattt tttcaaagac accaagatgt ggtaaatgaa    4980
aattattagt tcacttccct gctgccatga aactttgcct taagaaggtg ctggattcca    5040
aggtttgtaa aggcatctcg gtaaagactg ctttttgaat gcatatgatt ttgcatcagc    5100
tagactgagt tgattctgac cagacttgat ggttttaagt cggaaccgat aaattttaaa    5160
aaggagaaaa aataatttga cctagtagta taaaacatga ggctttaatg gtactttgct    5220
atgaaaagaa aacactgtat tccttatgca aaacacatgt atctttcatt atttataagt    5280
ggcctctctt agctcagtta ctcaattcat acgtagtatt ttttaaaata attttatatc    5340
tgtgtaccac cccatatatt tcatattact gtttcacatg tacagctttc tacttctttg    5400
taagaacacc aaccaaccaa ggtttaagtg attaataggc ttgagcaccg ggtggcagat    5460
gttctatgca gtgtggttca agtttctttg accgcactta tatgcattgc taatatggaa    5520
tttaagatac catacacagt ctctcatgga cctatctcta ttgtagaatt atgacttatg    5580
tcttacttgc caaattttc tgaatgtgac cttttttgc tgatttgctg ggtttgggat    5640
taactagcat tattttgcca ccttttatatt gtatttataa aaaaaaaagt actatcaatc    5700
aatcatacta ctttggattg ttgtgctggt gtaatgtgga tttaacatca ataaatattt    5760
gacaaataat agttgcagtt ttgtgaagca aaataaatat tcagtttta              5809
```

<210> SEQ ID NO 21
<211> LENGTH: 18
<212> TYPE: DNA
<213> ORGANISM: H. sapiens

<400> SEQUENCE: 21

-continued cccagccgtg gagtaaat                                                          18

<210> SEQ ID NO 22
<211> LENGTH: 18
<212> TYPE: DNA
<213> ORGANISM: H. sapiens

<400> SEQUENCE: 22
cccagctgtg gagtaaat                                                          18

<210> SEQ ID NO 23
<211> LENGTH: 41
<212> TYPE: DNA
<213> ORGANISM: H. sapiens

<400> SEQUENCE: 23
ggagtccatc ccagccgtgg agtaaatgga ctgattaacg g                                41

<210> SEQ ID NO 24
<211> LENGTH: 41
<212> TYPE: DNA
<213> ORGANISM: H. sapiens

<400> SEQUENCE: 24
ggagtccatc ccagctgtgg agtaaatgga ctgattaacg g                                41

<210> SEQ ID NO 25
<211> LENGTH: 343
<212> TYPE: DNA
<213> ORGANISM: H. sapiens

<400> SEQUENCE: 25
ccaacactga aaactgtagt tacgagtcaa tgggagaatc caacaatgac cacttccaac            60
actttccacc tcccctcca atcttggaga caagttcctt ggagttggct tcaaagaaac            120
catctgagat ccagcaggtg aacaaccctg agttaggcct gagcagggca gcccttcaaa           180
tgcaattcaa tgctgctgag agggaaacga acggagtcca tcccagccgt ggagtaaatg           240
gactgattaa cggcaaagct aacagtaata aatctcttcc aacaccagct gtcctgcttt           300
cacccactaa ggagccacca cctctgcttg ccaaaccaaa act                             343

<210> SEQ ID NO 26
<211> LENGTH: 343
<212> TYPE: DNA
<213> ORGANISM: H. sapiens

<400> SEQUENCE: 26
ccaacactga aaactgtagt tacgagtcaa tgggagaatc caacaatgac cacttccaac            60
actttccacc tcccctcca atcttggaga caagttcctt ggagttggct tcaaagaaac            120
catctgagat ccagcaggtg aacaaccctg agttaggcct gagcagggca gcccttcaaa           180
tgcaattcaa tgctgctgag agggaaacga acggagtcca tcccagctgt ggagtaaatg           240
gactgattaa cggcaaagct aacagtaata aatctcttcc aacaccagct gtcctgcttt           300
cacccactaa ggagccacca cctctgcttg ccaaaccaaa act                             343

<210> SEQ ID NO 27
<211> LENGTH: 93
<212> TYPE: DNA
<213> ORGANISM: H. sapiens

```
<400> SEQUENCE: 27
ttcaatgctg ctgagaggga aacgaacgga gtccatccca gccgtggagt aaatggactg      60
attaacggca aagctaacag taataaatct ctt                                   93

<210> SEQ ID NO 28
<211> LENGTH: 93
<212> TYPE: DNA
<213> ORGANISM: H. sapiens

<400> SEQUENCE: 28
ttcaatgctg ctgagaggga aacgaacgga gtccatccca gctgtggagt aaatggactg      60
attaacggca aagctaacag taataaatct ctt                                   93

<210> SEQ ID NO 29
<211> LENGTH: 21
<212> TYPE: DNA
<213> ORGANISM: Artificial Sequence
<220> FEATURE:
<223> OTHER INFORMATION: synthetic probe

<400> SEQUENCE: 29
cggccagacg tccgcggcct t                                                21

<210> SEQ ID NO 30
<211> LENGTH: 21
<212> TYPE: DNA
<213> ORGANISM: Artificial Sequence
<220> FEATURE:
<223> OTHER INFORMATION: synthetic probe

<400> SEQUENCE: 30
aaggccgcgg acgtctggcc g                                                21

<210> SEQ ID NO 31
<211> LENGTH: 25
<212> TYPE: DNA
<213> ORGANISM: Artificial Sequence
<220> FEATURE:
<223> OTHER INFORMATION: synthetic probe

<400> SEQUENCE: 31
gccacggcca gacgtccgcg gcctt                                            25

<210> SEQ ID NO 32
<211> LENGTH: 25
<212> TYPE: DNA
<213> ORGANISM: Artificial Sequence
<220> FEATURE:
<223> OTHER INFORMATION: synthetic probe

<400> SEQUENCE: 32
aaggccgcgg acgtctggcc gtggc                                            25

<210> SEQ ID NO 33
<211> LENGTH: 25
<212> TYPE: DNA
<213> ORGANISM: Artificial Sequence
<220> FEATURE:
<223> OTHER INFORMATION: synthetic probe

<400> SEQUENCE: 33
cggccagacg tccgcggcct tcctc                                            25
```

```
<210> SEQ ID NO 34
<211> LENGTH: 29
<212> TYPE: DNA
<213> ORGANISM: Artificial Sequence
<220> FEATURE:
<223> OTHER INFORMATION: synthetic probe

<400> SEQUENCE: 34
gaggaaggcc gcggacgtct ggccgtggc                                29

<210> SEQ ID NO 35
<211> LENGTH: 29
<212> TYPE: DNA
<213> ORGANISM: Artificial Sequence
<220> FEATURE:
<223> OTHER INFORMATION: synthetic probe

<400> SEQUENCE: 35
gccacggcca gacgtccgcg gccttcctc                                29

<210> SEQ ID NO 36
<211> LENGTH: 29
<212> TYPE: DNA
<213> ORGANISM: Artificial Sequence
<220> FEATURE:
<223> OTHER INFORMATION: synthetic probe

<400> SEQUENCE: 36
gaggaaggcc gcggacgtct ggccgtggc                                29

<210> SEQ ID NO 37
<211> LENGTH: 20
<212> TYPE: DNA
<213> ORGANISM: Artificial Sequence
<220> FEATURE:
<223> OTHER INFORMATION: synthetic probe

<400> SEQUENCE: 37
ctaagctggc aactagatgg                                          20

<210> SEQ ID NO 38
<211> LENGTH: 20
<212> TYPE: DNA
<213> ORGANISM: Artificial Sequence
<220> FEATURE:
<223> OTHER INFORMATION: synthetic probe

<400> SEQUENCE: 38
ccatctagtt gccagcttag                                          20

<210> SEQ ID NO 39
<211> LENGTH: 21
<212> TYPE: DNA
<213> ORGANISM: Artificial Sequence
<220> FEATURE:
<223> OTHER INFORMATION: synthetic probe

<400> SEQUENCE: 39
gatctaagct ggcaactaga t                                        21

<210> SEQ ID NO 40
<211> LENGTH: 21
<212> TYPE: DNA
<213> ORGANISM: Artificial Sequence
<220> FEATURE:
<223> OTHER INFORMATION: synthetic probe
```

```
<400> SEQUENCE: 40
atctagttgc cagcttagat c                                              21

<210> SEQ ID NO 41
<211> LENGTH: 23
<212> TYPE: DNA
<213> ORGANISM: Artificial Sequence
<220> FEATURE:
<223> OTHER INFORMATION: synthetic probe

<400> SEQUENCE: 41
gatctaagct ggcaactaga tgg                                            23

<210> SEQ ID NO 42
<211> LENGTH: 23
<212> TYPE: DNA
<213> ORGANISM: Artificial Sequence
<220> FEATURE:
<223> OTHER INFORMATION: synthetic probe

<400> SEQUENCE: 42
ccatctagtt gccagcttag atc                                            23

<210> SEQ ID NO 43
<211> LENGTH: 24
<212> TYPE: DNA
<213> ORGANISM: Artificial Sequence
<220> FEATURE:
<223> OTHER INFORMATION: synthetic probe

<400> SEQUENCE: 43
ccatcccagc cgtggagtaa atgg                                           24

<210> SEQ ID NO 44
<211> LENGTH: 24
<212> TYPE: DNA
<213> ORGANISM: Artificial Sequence
<220> FEATURE:
<223> OTHER INFORMATION: synthetic probe

<400> SEQUENCE: 44
ccatttactc cacggctggg atgg                                           24

<210> SEQ ID NO 45
<211> LENGTH: 20
<212> TYPE: DNA
<213> ORGANISM: Artificial Sequence
<220> FEATURE:
<223> OTHER INFORMATION: synthetic probe

<400> SEQUENCE: 45
cccagccgtg gagtaaatgg                                                20

<210> SEQ ID NO 46
<211> LENGTH: 20
<212> TYPE: DNA
<213> ORGANISM: Artificial Sequence
<220> FEATURE:
<223> OTHER INFORMATION: synthetic probe

<400> SEQUENCE: 46
ccatttactc cacggctggg                                                20

<210> SEQ ID NO 47
<211> LENGTH: 30
```

```
<212> TYPE: DNA
<213> ORGANISM: Artificial Sequence
<220> FEATURE:
<223> OTHER INFORMATION: synthetic probe

<400> SEQUENCE: 47
gtccatccca gccgtggagt aaatggactg                                    30

<210> SEQ ID NO 48
<211> LENGTH: 30
<212> TYPE: DNA
<213> ORGANISM: Artificial Sequence
<220> FEATURE:
<223> OTHER INFORMATION: synthetic probe

<400> SEQUENCE: 48
cagtccattt actccacggc tgggatggac                                    30

<210> SEQ ID NO 49
<211> LENGTH: 20
<212> TYPE: DNA
<213> ORGANISM: Artificial Sequence
<220> FEATURE:
<223> OTHER INFORMATION: synthetic probe

<400> SEQUENCE: 49
acccgcttcg gccacggcca                                               20

<210> SEQ ID NO 50
<211> LENGTH: 28
<212> TYPE: DNA
<213> ORGANISM: Artificial Sequence
<220> FEATURE:
<223> OTHER INFORMATION: synthetic probe

<400> SEQUENCE: 50
gtcgcctgcc acccgcttcg gccacggc                                      28

<210> SEQ ID NO 51
<211> LENGTH: 20
<212> TYPE: DNA
<213> ORGANISM: Artificial Sequence
<220> FEATURE:
<223> OTHER INFORMATION: synthetic probe

<400> SEQUENCE: 51
gccttcctca gcgctctgct                                               20

<210> SEQ ID NO 52
<211> LENGTH: 30
<212> TYPE: DNA
<213> ORGANISM: Artificial Sequence
<220> FEATURE:
<223> OTHER INFORMATION: synthetic probe

<400> SEQUENCE: 52
gccttcctca gcgctctgct gccctcgcag                                    30

<210> SEQ ID NO 53
<211> LENGTH: 25
<212> TYPE: DNA
<213> ORGANISM: Artificial Sequence
<220> FEATURE:
<223> OTHER INFORMATION: synthetic probe

<400> SEQUENCE: 53
```
gcgctctgct gccctcgcag ccgcc                                     25

<210> SEQ ID NO 54
<211> LENGTH: 30
<212> TYPE: DNA
<213> ORGANISM: Artificial Sequence
<220> FEATURE:
<223> OTHER INFORMATION: synthetic probe

<400> SEQUENCE: 54
gccctcgcag ccgccgccgg cggccgtcaa                                30

<210> SEQ ID NO 55
<211> LENGTH: 20
<212> TYPE: DNA
<213> ORGANISM: Artificial Sequence
<220> FEATURE:
<223> OTHER INFORMATION: synthetic probe

<400> SEQUENCE: 55
cagtgggtta ccaaccccag                                           20

<210> SEQ ID NO 56
<211> LENGTH: 20
<212> TYPE: DNA
<213> ORGANISM: Artificial Sequence
<220> FEATURE:
<223> OTHER INFORMATION: synthetic probe

<400> SEQUENCE: 56
ccaaccccag atctaagctg                                           20

<210> SEQ ID NO 57
<211> LENGTH: 20
<212> TYPE: DNA
<213> ORGANISM: Artificial Sequence
<220> FEATURE:
<223> OTHER INFORMATION: synthetic probe

<400> SEQUENCE: 57
ggaaagcccg tacgccctga                                           20

<210> SEQ ID NO 58
<211> LENGTH: 20
<212> TYPE: DNA
<213> ORGANISM: Artificial Sequence
<220> FEATURE:
<223> OTHER INFORMATION: synthetic probe

<400> SEQUENCE: 58
cagtgctcac aagatgctgg                                           20

<210> SEQ ID NO 59
<211> LENGTH: 20
<212> TYPE: DNA
<213> ORGANISM: Artificial Sequence
<220> FEATURE:
<223> OTHER INFORMATION: synthetic probe

<400> SEQUENCE: 59
aatgctgctg agagggaaac                                           20

<210> SEQ ID NO 60
<211> LENGTH: 25
<212> TYPE: DNA
<213> ORGANISM: Artificial Sequence

```
<220> FEATURE:
<223> OTHER INFORMATION: synthetic probe

<400> SEQUENCE: 60
agagggaaac gaacggagtc catcc                                          25

<210> SEQ ID NO 61
<211> LENGTH: 30
<212> TYPE: DNA
<213> ORGANISM: Artificial Sequence
<220> FEATURE:
<223> OTHER INFORMATION: synthetic probe

<400> SEQUENCE: 61
gtggagtaaa tggactgatt aacggcaaag                                     30

<210> SEQ ID NO 62
<211> LENGTH: 21
<212> TYPE: DNA
<213> ORGANISM: Artificial Sequence
<220> FEATURE:
<223> OTHER INFORMATION: synthetic probe

<400> SEQUENCE: 62
gtaaatggac tgattaacgg c                                              21

<210> SEQ ID NO 63
<211> LENGTH: 120
<212> TYPE: DNA
<213> ORGANISM: H. sapiens

<400> SEQUENCE: 63
ggacaggcgt cccactgctc gtcgcctgcc acccgcttcg gccacggcca gacgtccgcg    60
gccttcctca gcgctctgct gccctcgcag ccgccgccgg cggccgtcaa cgccctgggg   120

<210> SEQ ID NO 64
<211> LENGTH: 19
<212> TYPE: DNA
<213> ORGANISM: Artificial Sequence
<220> FEATURE:
<223> OTHER INFORMATION: synthetic primer

<400> SEQUENCE: 64
ggacaggcgt ccactgctc                                                 19

<210> SEQ ID NO 65
<211> LENGTH: 20
<212> TYPE: DNA
<213> ORGANISM: Artificial Sequence
<220> FEATURE:
<223> OTHER INFORMATION: synthetic primer

<400> SEQUENCE: 65
ccccagggcg ttgacggccg                                                20

<210> SEQ ID NO 66
<211> LENGTH: 20
<212> TYPE: DNA
<213> ORGANISM: Artificial Sequence
<220> FEATURE:
<223> OTHER INFORMATION: synthetic primer

<400> SEQUENCE: 66
ggaccctctg aagctccagc                                                20
```

<210> SEQ ID NO 67
<211> LENGTH: 20
<212> TYPE: DNA
<213> ORGANISM: Artificial Sequence
<220> FEATURE:
<223> OTHER INFORMATION: synthetic primer

<400> SEQUENCE: 67 gcggggtga caccttgggg                                            20

<210> SEQ ID NO 68
<211> LENGTH: 20
<212> TYPE: DNA
<213> ORGANISM: Artificial Sequence
<220> FEATURE:
<223> OTHER INFORMATION: synthetic primer

<400> SEQUENCE: 68
ggaccctctg aagctccagc                                           20

<210> SEQ ID NO 69
<211> LENGTH: 23
<212> TYPE: DNA
<213> ORGANISM: Artificial Sequence
<220> FEATURE:
<223> OTHER INFORMATION: synthetic primer

<400> SEQUENCE: 69
ccgtggccga agcgggtggc agg                                       23

<210> SEQ ID NO 70
<211> LENGTH: 20
<212> TYPE: DNA
<213> ORGANISM: Artificial Sequence
<220> FEATURE:
<223> OTHER INFORMATION: synthetic primer

<400> SEQUENCE: 70
cctcgccgtc gcccccgccc                                           20

<210> SEQ ID NO 71
<211> LENGTH: 23
<212> TYPE: DNA
<213> ORGANISM: Artificial Sequence
<220> FEATURE:
<223> OTHER INFORMATION: synthetic primer

<400> SEQUENCE: 71
ccgtggccga agcgggtggc agg                                       23

<210> SEQ ID NO 72
<211> LENGTH: 20
<212> TYPE: DNA
<213> ORGANISM: Artificial Sequence
<220> FEATURE:
<223> OTHER INFORMATION: synthetic primer

<400> SEQUENCE: 72
cctcgccgtc gcccccgccc                                           20

<210> SEQ ID NO 73
<211> LENGTH: 23
<212> TYPE: DNA
<213> ORGANISM: Artificial Sequence
<220> FEATURE:
<223> OTHER INFORMATION: synthetic primer -continued

```
<400> SEQUENCE: 73
ccgtggccga agcgggtggc agg                                                    23

<210> SEQ ID NO 74
<211> LENGTH: 25
<212> TYPE: DNA
<213> ORGANISM: Artificial Sequence
<220> FEATURE:
<223> OTHER INFORMATION: synthetic primer

<400> SEQUENCE: 74
aggtgtcact tctcttttc ccccc                                                   25

<210> SEQ ID NO 75
<211> LENGTH: 24
<212> TYPE: DNA
<213> ORGANISM: Artificial Sequence
<220> FEATURE:
<223> OTHER INFORMATION: synthetic primer

<400> SEQUENCE: 75
ggggagggaa gtggaggacc gcgg                                                   24

<210> SEQ ID NO 76
<211> LENGTH: 20
<212> TYPE: DNA
<213> ORGANISM: Artificial Sequence
<220> FEATURE:
<223> OTHER INFORMATION: synthetic primer

<400> SEQUENCE: 76
cagtgggtta ccaaccccag                                                        20

<210> SEQ ID NO 77
<211> LENGTH: 20
<212> TYPE: DNA
<213> ORGANISM: Artificial Sequence
<220> FEATURE:
<223> OTHER INFORMATION: synthetic primer

<400> SEQUENCE: 77
gtgcaccccg ttctcacgca                                                        20

<210> SEQ ID NO 78
<211> LENGTH: 29
<212> TYPE: DNA
<213> ORGANISM: Artificial Sequence
<220> FEATURE:
<223> OTHER INFORMATION: synthetic primer

<400> SEQUENCE: 78
tcttgtacta ctgaaggagg aatttatgc                                              29

<210> SEQ ID NO 79
<211> LENGTH: 31
<212> TYPE: DNA
<213> ORGANISM: Artificial Sequence
<220> FEATURE:
<223> OTHER INFORMATION: synthetic primer

<400> SEQUENCE: 79
ttttccgtat tggttagtaa tgtagaatta g                                           31

<210> SEQ ID NO 80
```

```
<211> LENGTH: 23
<212> TYPE: DNA
<213> ORGANISM: Artificial Sequence
<220> FEATURE:
<223> OTHER INFORMATION: synthetic primer

<400> SEQUENCE: 80
gggaaacgaa cggagtccat ccc                                              23

<210> SEQ ID NO 81
<211> LENGTH: 20
<212> TYPE: DNA
<213> ORGANISM: Artificial Sequence
<220> FEATURE:
<223> OTHER INFORMATION: synthetic primer

<400> SEQUENCE: 81
agcaggacag ctggtgttgg                                                  20

<210> SEQ ID NO 82
<211> LENGTH: 24
<212> TYPE: DNA
<213> ORGANISM: Artificial Sequence
<220> FEATURE:
<223> OTHER INFORMATION: synthetic primer

<400> SEQUENCE: 82
cacaacacag ggattctcag aaga                                             24

<210> SEQ ID NO 83
<211> LENGTH: 20
<212> TYPE: DNA
<213> ORGANISM: Artificial Sequence
<220> FEATURE:
<223> OTHER INFORMATION: synthetic primer

<400> SEQUENCE: 83
agctggtgtt ggaagagatt                                                  20

<210> SEQ ID NO 84
<211> LENGTH: 18
<212> TYPE: DNA
<213> ORGANISM: Artificial Sequence
<220> FEATURE:
<223> OTHER INFORMATION: synthetic primer

<400> SEQUENCE: 84
ccgacgtgtt cccactgc                                                    18

<210> SEQ ID NO 85
<211> LENGTH: 20
<212> TYPE: DNA
<213> ORGANISM: Artificial Sequence
<220> FEATURE:
<223> OTHER INFORMATION: synthetic primer

<400> SEQUENCE: 85
cgcacggaga gaaatgtgtg                                                  20

<210> SEQ ID NO 86
<211> LENGTH: 208
<212> TYPE: DNA
<213> ORGANISM: H. sapiens
<220> FEATURE:
<221> NAME/KEY: misc_feature
<222> LOCATION: 33
<223> OTHER INFORMATION: n = A,T,C or G
```

<400> SEQUENCE: 86

```
gtcagtgggt taccaacccc agatctaagc tgncaactag atggaaagcc cgtacgccct      60
gacagtgctc acaagatgct ggtgcgtgag aacggggtgc actctctgat catagagcca    120
gtcacgtcac gtgatgccgg catctacaca tgtatagcta ccaaccgagc aggacagaac    180
tcattcagcc tggagcttgt ggttgctg                                       208
```

<210> SEQ ID NO 87
<211> LENGTH: 1106
<212> TYPE: PRT
<213> ORGANISM: H. sapiens

<400> SEQUENCE: 87

```
Met Ser Gly Thr Ser Ser His Glu Ser Phe Tyr Asp Ser Leu Ser Asp
1               5                   10                  15

Met Gln Glu Glu Ser Lys Asn Thr Asp Phe Phe Pro Gly Leu Ser Ala
            20                  25                  30

Phe Leu Ser Gln Glu Glu Ile Asn Lys Ser Leu Asp Leu Ala Arg Arg
        35                  40                  45

Ala Ile Ala Asp Ser Glu Thr Glu Asp Phe Asp Ser Glu Lys Glu Ile
    50                  55                  60

Ser Gln Ile Phe Ser Thr Ser Pro Ala Ser Leu Cys Glu His Pro Ser
65                  70                  75                  80

His Lys Glu Thr Lys Leu Gly Glu His Ala Ser Arg Arg Pro Gln Asp
                85                  90                  95

Asn Arg Ser Thr Pro Val Gln Pro Leu Ala Glu Lys Gln Thr Lys Ser
            100                 105                 110

Ile Ser Ser Pro Val Ser Lys Arg Lys Pro Ala Met Ser Pro Leu Leu
        115                 120                 125

Thr Arg Pro Ser Tyr Ile Arg Ser Leu Arg Lys Ala Glu Lys Arg Gly
    130                 135                 140

Ala Lys Thr Pro Ser Thr Asn Val Lys Pro Lys Thr Pro His Gln Arg
145                 150                 155                 160

Lys Gly Gly Pro Gln Ser Gln Leu Cys Asp Lys Ala Ala Asn Leu Ile
                165                 170                 175

Glu Glu Leu Thr Ser Ile Phe Lys Ala Ala Lys Pro Arg Asn Arg Ser
            180                 185                 190

Pro Asn Gly Glu Ser Ser Ser Pro Asp Ser Gly Tyr Leu Ser Pro Lys
        195                 200                 205

Asn Gln Pro Ser Ala Leu Leu Ser Ala Ser Ala Ser Gln Ser Pro Met
    210                 215                 220

Glu Asp Gln Gly Glu Met Glu Arg Glu Val Lys Ser Pro Gly Ala Arg
225                 230                 235                 240

His Cys Tyr Gln Asp Asn Gln Asp Leu Ala Val Pro His Asn Arg Lys
                245                 250                 255

Ser His Pro Gln Pro His Ser Ala Leu His Phe Pro Ala Ala Pro Arg
            260                 265                 270

Phe Ile Gln Lys Leu Arg Ser Gln Glu Val Ala Glu Gly Ser Arg Val
        275                 280                 285

Tyr Leu Glu Cys Arg Val Thr Gly Asn Pro Thr Pro Arg Val Arg Trp
    290                 295                 300

Phe Cys Glu Gly Lys Glu Leu His Asn Thr Pro Asp Ile Gln Ile His
305                 310                 315                 320
```

-continued

```
Cys Glu Gly Gly Asp Leu His Thr Leu Ile Ile Ala Glu Ala Phe Glu
            325                 330                 335

Asp Asp Thr Gly Arg Tyr Thr Cys Leu Ala Thr Asn Pro Ser Gly Ser
        340                 345                 350

Asp Thr Thr Ser Ala Glu Val Phe Ile Glu Gly Ala Ser Ser Thr Asp
    355                 360                 365

Ser Asp Ser Glu Ser Leu Ala Phe Lys Ser Arg Ala Gly Ala Met Pro
370                 375                 380

Gln Ala Gln Lys Lys Thr Ser Val Ser Leu Thr Ile Gly Ser Ser
385                 390                 395                 400

Ser Pro Lys Thr Gly Val Thr Thr Ala Val Ile Gln Pro Leu Ser Val
                405                 410                 415

Pro Val Gln Gln Val His Ser Pro Thr Ser Tyr Leu Cys Arg Pro Asp
            420                 425                 430

Gly Thr Thr Thr Ala Tyr Phe Pro Pro Val Phe Thr Lys Glu Leu Gln
        435                 440                 445

Asn Thr Ala Val Ala Glu Gly Gln Val Val Leu Glu Cys Arg Val
    450                 455                 460

Arg Gly Ala Pro Pro Leu Gln Val Gln Trp Phe Arg Gln Gly Ser Glu
465                 470                 475                 480

Ile Gln Asp Ser Pro Asp Phe Arg Ile Leu Gln Lys Pro Arg Ser
                485                 490                 495

Thr Ala Glu Pro Glu Ile Cys Thr Leu Val Ile Ala Glu Thr Phe
            500                 505                 510

Pro Glu Asp Ala Gly Ile Phe Thr Cys Ser Ala Arg Asn Asp Tyr Gly
        515                 520                 525

Ser Ala Thr Ser Thr Ala Gln Leu Val Val Thr Ser Ala Asn Thr Glu
    530                 535                 540

Asn Cys Ser Tyr Glu Ser Met Gly Glu Ser Asn Asp His Phe Gln
545                 550                 555                 560

His Phe Pro Pro Pro Pro Ile Leu Glu Thr Ser Ser Leu Glu Leu
                565                 570                 575

Ala Ser Lys Lys Pro Ser Glu Ile Gln Gln Val Asn Asn Pro Glu Leu
            580                 585                 590

Gly Leu Ser Arg Ala Ala Leu Gln Met Gln Phe Asn Ala Ala Glu Arg
        595                 600                 605

Glu Thr Asn Gly Val His Pro Ser Arg Gly Val Asn Gly Leu Ile Asn
    610                 615                 620

Gly Lys Ala Asn Ser Asn Lys Ser Leu Pro Thr Pro Ala Val Leu Leu
625                 630                 635                 640

Ser Pro Thr Lys Glu Pro Pro Leu Leu Ala Lys Pro Lys Leu Gly
                645                 650                 655

Phe Pro Lys Lys Ala Ser Arg Thr Ala Arg Ile Ala Ser Asp Glu Glu
            660                 665                 670

Ile Gln Gly Thr Lys Asp Ala Val Ile Gln Asp Leu Glu Arg Lys Leu
        675                 680                 685

Arg Phe Lys Glu Asp Leu Leu Asn Asn Gly Gln Pro Arg Leu Thr Tyr
    690                 695                 700

Glu Glu Arg Met Ala Arg Arg Leu Leu Gly Ala Asp Ser Ala Thr Val
705                 710                 715                 720

Phe Asn Ile Gln Glu Pro Glu Glu Thr Ala Asn Gln Glu Tyr Lys
                725                 730                 735

Val Ser Ser Cys Glu Gln Arg Leu Ile Ser Glu Ile Glu Tyr Arg Leu
```

```
                740                 745                 750
Glu Arg Ser Pro Val Asp Glu Ser Gly Asp Glu Val Gln Tyr Gly Asp
            755                 760                 765

Val Pro Val Glu Asn Gly Met Ala Pro Phe Phe Glu Met Lys Leu Lys
        770                 775                 780

His Tyr Lys Ile Phe Glu Gly Met Pro Val Thr Phe Thr Cys Arg Val
785                 790                 795                 800

Ala Gly Asn Pro Lys Pro Lys Ile Tyr Trp Phe Lys Asp Gly Lys Gln
            805                 810                 815

Ile Ser Pro Lys Ser Asp His Tyr Thr Ile Gln Arg Asp Leu Asp Gly
        820                 825                 830

Thr Cys Ser Leu His Thr Thr Ala Ser Thr Leu Asp Asp Asp Gly Asn
    835                 840                 845

Tyr Thr Ile Met Ala Ala Asn Pro Gln Gly Arg Ile Ser Cys Thr Gly
        850                 855                 860

Arg Leu Met Val Gln Ala Val Asn Gln Arg Gly Arg Ser Pro Arg Ser
865                 870                 875                 880

Pro Ser Gly His Pro His Val Arg Arg Pro Arg Ser Arg Ser Arg Asp
            885                 890                 895

Ser Gly Asp Glu Asn Glu Pro Ile Gln Glu Arg Phe Phe Arg Pro His
        900                 905                 910

Phe Leu Gln Ala Pro Gly Asp Leu Thr Val Gln Glu Gly Lys Leu Cys
    915                 920                 925

Arg Met Asp Cys Lys Val Ser Gly Leu Pro Thr Pro Asp Leu Ser Trp
    930                 935                 940

Gln Leu Asp Gly Lys Pro Val Arg Pro Asp Ser Ala His Lys Met Leu
945                 950                 955                 960

Val Arg Glu Asn Gly Val His Ser Leu Ile Ile Glu Pro Val Thr Ser
            965                 970                 975

Arg Asp Ala Gly Ile Tyr Thr Cys Ile Ala Thr Asn Arg Ala Gly Gln
        980                 985                 990

Asn Ser Phe Ser Leu Glu Leu Val Val Ala Ala Lys Glu Ala His Lys
    995                1000                1005

Pro Pro Val Phe Ile Glu Lys Leu Gln Asn Thr Gly Val Ala Asp Gly
    1010                1015                1020

Tyr Pro Val Arg Leu Glu Cys Arg Val Leu Gly Val Pro Pro Pro Gln
1025                1030                1035                1040

Ile Phe Trp Lys Lys Glu Asn Glu Ser Leu Thr His Ser Thr Asp Arg
            1045                1050                1055

Val Ser Met His Gln Asp Asn His Gly Tyr Ile Cys Leu Leu Ile Gln
        1060                1065                1070

Gly Ala Thr Lys Glu Asp Ala Gly Trp Tyr Thr Val Ser Ala Lys Asn
    1075                1080                1085

Glu Ala Gly Ile Val Ser Cys Thr Ala Arg Leu Asp Val Tyr Ile Ser
    1090                1095                1100

Arg His
1105

<210> SEQ ID NO 88
<211> LENGTH: 40
<212> TYPE: PRT
<213> ORGANISM: H. sapiens
<220> FEATURE:
<221> NAME/KEY: VARIANT
<222> LOCATION: 11
```

-continued

<223> OTHER INFORMATION: Xaa = Any Amino Acid

<400> SEQUENCE: 88

Val Ser Gly Leu Pro Thr Pro Asp Leu Ser Xaa Gln Leu Asp Gly Lys
1               5                   10                  15

Pro Val Arg Pro Asp Ser Ala His Lys Met Leu Val Arg Glu Asn Gly
            20                  25                  30

Val His Ser Leu Ile Ile Glu Pro
        35                  40

<210> SEQ ID NO 89
<211> LENGTH: 40
<212> TYPE: PRT
<213> ORGANISM: H. sapiens

<400> SEQUENCE: 89

Val Ser Gly Leu Pro Thr Pro Asp Leu Ser Trp Gln Leu Asp Gly Lys
1               5                   10                  15

Pro Val Arg Pro Asp Ser Ala His Lys Met Leu Val Arg Glu Asn Gly
            20                  25                  30

Val His Ser Leu Ile Ile Glu Pro
        35                  40

<210> SEQ ID NO 90
<211> LENGTH: 40
<212> TYPE: PRT
<213> ORGANISM: mouse

<400> SEQUENCE: 90

Val Ser Gly Leu Pro Thr Pro Asp Leu Ser Trp Gln Leu Asp Gly Lys
1               5                   10                  15

Pro Ile Arg Pro Asp Ser Ala His Lys Met Leu Val Arg Glu Asn Gly
            20                  25                  30

Val His Ser Leu Ile Ile Glu Pro
        35                  40

<210> SEQ ID NO 91
<211> LENGTH: 29
<212> TYPE: DNA
<213> ORGANISM: Artificial Sequence
<220> FEATURE:
<223> OTHER INFORMATION: synthetic primer

<400> SEQUENCE: 91
tcttgtacta ctgaaggagg aatttatgc                                    29

<210> SEQ ID NO 92
<211> LENGTH: 31
<212> TYPE: DNA
<213> ORGANISM: Artificial Sequence
<220> FEATURE:
<223> OTHER INFORMATION: synthetic primer

<400> SEQUENCE: 92
ttttccgtat tggttagtaa tgtagaatta g                                 31

<210> SEQ ID NO 93
<211> LENGTH: 343
<212> TYPE: DNA
<213> ORGANISM: H. sapiens
<220> FEATURE:
<221> NAME/KEY: misc_feature
<222> LOCATION: 228

<223> OTHER INFORMATION: n = A,T,C or G

<400> SEQUENCE: 93

```
ccaacactga aaactgtagt tacgagtcaa tgggagaatc aacaatgac cacttccaac      60
actttccacc tccccctcca atcttggaga caagttcctt ggagttggct tcaaagaaac    120
catctgagat ccagcaggtg aacaaccctg agttaggcct gagcagggca gcccttcaaa    180
tgcaattcaa tgctgctgag agggaaacga acggagtcca tcccagcngt ggagtaaatg    240
gactgattaa cggcaaagct aacagtaata aatctcttcc aacaccagct gtcctgcttt    300
cacccactaa ggagccacca cctctgcttg ccaaaccaaa act                      343
```

<210> SEQ ID NO 94
<211> LENGTH: 113
<212> TYPE: PRT
<213> ORGANISM: H. sapiens
<220> FEATURE:
<221> NAME/KEY: VARIANT
<222> LOCATION: 76
<223> OTHER INFORMATION: Xaa = Any Amino Acid

<400> SEQUENCE: 94

```
Asn Thr Glu Asn Cys Ser Tyr Glu Ser Met Gly Glu Ser Asn Asn Asp
1               5                  10                  15
His Phe Gln His Phe Pro Pro Pro Pro Ile Leu Glu Thr Ser Ser
            20                  25                  30
Leu Glu Leu Ala Ser Lys Lys Pro Ser Glu Ile Gln Gln Val Asn Asn
        35                  40                  45
Pro Glu Leu Gly Leu Ser Arg Ala Ala Leu Gln Met Gln Phe Asn Ala
    50                  55                  60
Ala Glu Arg Glu Thr Asn Gly Val His Pro Ser Xaa Gly Val Asn Gly
65                  70                  75                  80
Leu Ile Asn Gly Lys Ala Asn Ser Asn Lys Ser Leu Pro Thr Pro Ala
                85                  90                  95
Val Leu Leu Ser Pro Thr Lys Glu Pro Pro Leu Leu Ala Lys Pro
            100                 105                 110
Lys
```

<210> SEQ ID NO 95
<211> LENGTH: 22
<212> TYPE: PRT
<213> ORGANISM: H. sapiens

<400> SEQUENCE: 95

```
Ala Glu Arg Glu Thr Asn Gly Val His Pro Ser Arg Gly Val Asn Gly
1               5                   10                  15
Leu Ile Asn Gly Lys Ala
            20
```

<210> SEQ ID NO 96
<211> LENGTH: 22
<212> TYPE: PRT
<213> ORGANISM: mouse

<400> SEQUENCE: 96

```
Ala Glu Arg Glu Thr Asn Gly Val His Pro Ser His Gly Val Asn Gly
1               5                   10                  15
Leu Ile Asn Gly Lys Ala
            20
```

-continued

```
<210> SEQ ID NO 97
<211> LENGTH: 24
<212> TYPE: DNA
<213> ORGANISM: Artificial Sequence
<220> FEATURE:
<223> OTHER INFORMATION: synthetic primer

<400> SEQUENCE: 97
cacaacacag ggattctcag aaga                                          24

<210> SEQ ID NO 98
<211> LENGTH: 20
<212> TYPE: DNA
<213> ORGANISM: Artificial Sequence
<220> FEATURE:
<223> OTHER INFORMATION: synthetic primer

<400> SEQUENCE: 98
agctggtgtt ggaagagatt                                               20

<210> SEQ ID NO 99
<211> LENGTH: 772
<212> TYPE: PRT
<213> ORGANISM: H. sapiens

<400> SEQUENCE: 99

Pro Glu Ser Pro Gly Gly Arg Gly Ile Lys Pro Asp Thr Cys Pro Ala
1               5                   10                  15

Pro Gly Pro Arg Ser Pro Leu Gln Leu Pro Leu Ala Pro Asp Ala Glu
            20                  25                  30

Ser Gly Ser Ser Gly Arg Arg Pro Gly Glu Pro Arg Asp Pro Leu Lys
        35                  40                  45

Leu Gln Gln Leu Gln Asn Gln Ile Arg Leu Glu Gln Glu Ala Gly Ala
    50                  55                  60

Arg Gln Pro Pro Ala Pro Arg Ser Ala Pro Pro Ser Pro Pro Phe
65                  70                  75                  80

Pro Pro Pro Pro Ala Phe Pro Glu Leu Ala Ala Cys Thr Pro Pro Ala
                85                  90                  95

Ser Pro Glu Pro Met Ser Ala Leu Ala Ser Arg Ser Ala Pro Ala Met
            100                 105                 110

Gln Ser Ser Gly Ser Phe Asn Tyr Ala Arg Pro Lys Gln Phe Ile Ala
        115                 120                 125

Ala Gln Asn Leu Gly Pro Ala Ser Gly His Gly Thr Pro Ala Ser Ser
    130                 135                 140

Pro Ser Ser Ser Leu Pro Ser Pro Met Ser Pro Thr Pro Arg Gln
145                 150                 155                 160

Phe Gly Arg Ala Pro Val Pro Pro Phe Ala Gln Pro Phe Gly Ala Glu
                165                 170                 175

Pro Glu Ala Pro Trp Gly Ser Ser Pro Ser Pro Pro Pro Pro
            180                 185                 190

Pro Pro Val Phe Ser Pro Thr Ala Ala Phe Pro Val Pro Asp Val Phe
        195                 200                 205

Pro Leu Pro Pro Pro Pro Pro Leu Pro Ser Pro Gly Gln Ala Ser
    210                 215                 220

His Cys Ser Ser Pro Ala Thr Arg Phe Gly His Gly Gln Thr Pro Ala
225                 230                 235                 240

Ala Phe Leu Ser Ala Leu Leu Pro Ser Gln Pro Pro Ala Ala Val
                245                 250                 255
```

-continued

```
Asn Ala Leu Gly Leu Pro Lys Gly Val Thr Pro Ala Gly Phe Pro Lys
            260                 265                 270

Lys Ala Ser Arg Thr Ala Arg Ile Ala Ser Asp Glu Glu Ile Gln Gly
            275                 280                 285

Thr Lys Asp Ala Val Ile Gln Asp Leu Glu Arg Lys Leu Arg Phe Lys
            290                 295                 300

Glu Asp Leu Leu Asn Asn Gly Gln Pro Arg Leu Thr Tyr Glu Glu Arg
305                 310                 315                 320

Met Ala Arg Arg Leu Leu Gly Ala Asp Ser Ala Thr Val Phe Asn Ile
                325                 330                 335

Gln Glu Pro Glu Glu Thr Ala Asn Gln Glu Tyr Lys Val Ser Ser
            340                 345                 350

Cys Glu Gln Arg Leu Ile Ser Glu Ile Glu Tyr Arg Leu Glu Arg Ser
            355                 360                 365

Pro Val Asp Glu Ser Gly Asp Glu Val Gln Tyr Gly Asp Val Pro Val
            370                 375                 380

Glu Asn Gly Met Ala Pro Phe Phe Glu Met Lys Leu Lys His Tyr Lys
385                 390                 395                 400

Ile Phe Glu Gly Met Pro Val Thr Phe Thr Cys Arg Val Ala Gly Asn
                405                 410                 415

Pro Lys Pro Lys Ile Tyr Trp Phe Lys Asp Gly Lys Gln Ile Ser Pro
            420                 425                 430

Lys Ser Asp His Tyr Thr Ile Gln Arg Asp Leu Asp Gly Thr Cys Ser
            435                 440                 445

Leu His Thr Thr Ala Ser Thr Leu Asp Asp Asp Gly Asn Tyr Thr Ile
            450                 455                 460

Met Ala Ala Asn Pro Gln Gly Arg Ile Ser Cys Thr Gly Arg Leu Met
465                 470                 475                 480

Val Gln Ala Val Asn Gln Arg Gly Arg Ser Pro Arg Ser Pro Ser Gly
                485                 490                 495

His Pro His Val Arg Arg Pro Arg Ser Arg Ser Arg Asp Ser Gly Asp
            500                 505                 510

Glu Asn Glu Pro Ile Gln Glu Arg Phe Phe Arg Pro His Phe Leu Gln
            515                 520                 525

Ala Pro Gly Asp Leu Thr Val Gln Glu Gly Lys Leu Cys Arg Met Asp
            530                 535                 540

Cys Lys Val Ser Gly Leu Pro Thr Pro Asp Leu Ser Trp Gln Leu Asp
545                 550                 555                 560

Gly Lys Pro Val Arg Pro Asp Ser Ala His Lys Met Leu Val Arg Glu
                565                 570                 575

Asn Gly Val His Ser Leu Ile Ile Glu Pro Val Thr Ser Arg Asp Ala
            580                 585                 590

Gly Ile Tyr Thr Cys Ile Ala Thr Asn Arg Ala Gly Gln Asn Ser Phe
            595                 600                 605

Ser Leu Glu Leu Val Val Ala Ala Lys Glu Ala His Lys Pro Pro Val
            610                 615                 620

Phe Ile Glu Lys Leu Gln Asn Thr Gly Val Ala Asp Gly Tyr Pro Val
625                 630                 635                 640

Arg Leu Glu Cys Arg Val Leu Gly Val Pro Pro Gln Ile Phe Trp
                645                 650                 655

Lys Lys Glu Asn Glu Ser Leu Thr His Ser Thr Asp Arg Val Ser Met
            660                 665                 670
```

```
His Gln Asp Asn His Gly Tyr Ile Cys Leu Leu Ile Gln Gly Ala Thr
            675                 680                 685

Lys Glu Asp Ala Gly Trp Tyr Thr Val Ser Ala Lys Asn Glu Ala Gly
        690                 695                 700

Ile Val Ser Cys Thr Ala Arg Leu Asp Val Tyr Thr Gln Trp His Gln
705                 710                 715                 720

Gln Ser Gln Ser Thr Lys Pro Lys Val Arg Pro Ser Ala Ser Arg
                725                 730                 735

Tyr Ala Ala Leu Ser Asp Gln Gly Leu Asp Ile Lys Ala Ala Phe Gln
                740                 745                 750

Pro Glu Ala Asn Pro Ser His Leu Thr Leu Asn Thr Ala Leu Val Glu
            755                 760                 765

Ser Glu Asp Leu
    770

<210> SEQ ID NO 100
<211> LENGTH: 1080
<212> TYPE: DNA
<213> ORGANISM: H. sapiens

<400> SEQUENCE: 100
tgagagtgaa atgggcgagc atacttcact gacttagcgc ttggtccaga atgaactgct      60
ggccccacac ttgggcctgc taacgtgtgc ccgttccctg ggtgttctct gcagctggcc     120
taagtgccaa gcgatgtcca caagctgagc tcactcctgg aatacacgtt cctggccgtt     180
ccatctctga aggtgtcact tctcttttc cccccaggga ccctctgaag ctccagcaac      240
tccagaacca aatccgactg gagcaggagg ccggcgctcg gcagcctccg ccagccccgc     300
gcagcgcgcc gccctcgccc ccttccccgc cgccgcccgc cttccccgag ctcgcggcct     360
gcacgccgcc cgcgtccccg gagcccatga gcgcgctggc ctcccgctcc gccccgcca      420 tgcagtcctc cggctccttc aactacgcgc gccccaagca gttcatcgcc gcgcagaacc     480
tcgggcccgc gtcgggccac ggcacgccgg cctccagccc cagctcgtcc agcctcccgt     540
cgcccatgtc cccgacgccg aggcagttcg gccgcgcccc cgtgccgccc ttcgcgcagc     600
ccttcggcgc tgagcccgag gccccgtggg gctcctcctc gccgtcgccc cgccccgc      660 caccccggt cttcagcccc acggctgcct tccggtgcc cgacgtgttc ccactgccgc      720
cgccaccacc gccgctcccg agcccgggac aggcgtccca ctgctcgtcg cctgccaccc     780
gcttcggcca cagccagacg cccgcggcct tcctcagcgc tctgctgccc tcgcagccgc     840
cgccggcggc cgtcaacgcc ctggggctgc ccaagggtgt caccccccg tgagtaaccg      900 ccgcggtcct ccacttccct gccctccgc ctcgggtcgc cctgggactc ccacatctcc     960
atacacgcgc tcccatcagc ctgcaaccca gagcgcccca gtaacatttc acacatttct    1020
ctccgtgcga tgtaaaaatt cttaacggca atttgactca gtgattcttg cgtagccact    1080

<210> SEQ ID NO 101
<211> LENGTH: 410
<212> TYPE: DNA
<213> ORGANISM: H. sapiens

<400> SEQUENCE: 101
agccacctct tgtactactg aaggaggaat ttatgcagac ttcttagcta ccagtgattt      60
cactctgttt aatacaaaa atttacatgt atttctttta tgatttaggt cagtgggtta     120
ccaaccccag atctaagctg gcaactagat ggaaagcccg tacgccctga cagtgctcac     180
```

-continued

```
aagatgctgg tgcgtgagaa cggggtgcac tctctgatca tagagccagt cacgtcacgt    240
gatgccggca tctacacatg tatagctacc aaccgagcag gacagaactc attcagcctg    300
gagcttgtgg ttgctggtag gctcatctgt gaatccttgc tctctgacag aatgaacatc    360
agacttacaa atgtaaacta attctacatt actaaccaat acggaaaata                410
```

<210> SEQ ID NO 102
<211> LENGTH: 480
<212> TYPE: DNA
<213> ORGANISM: H. sapiens

<400> SEQUENCE: 102

```
tgcgtcagat gagagcagca caatcacctc ttctttaaca acttcacaca acacagggat     60
tctcagaaga ctctgacagt gtgaaatcac ttgttgaact agtggcatct tcttatgttt    120
ttcctctctt tccccttcct tagccaacac tgaaaactgt agttacgagt caatgggaga    180
atccaacaat gaccacttcc aacactttcc acctcccccct ccaatcttgg agacaagttc    240
cttggagttg gcttcaaaga aaccatctga gatccagcag gtgaacaacc ctgagttagg    300
cctgagcagg gcagcccttc aaatgcaatt caatgctgct gagagggaaa cgaacggagt    360
ccatcccagc cgtggagtaa atggactgat taacggcaaa gctaacagta ataaatctct    420
tccaacacca gctgtcctgc tttcacccac taaggagcca ccacctctgc ttgccaaacc    480
```

<210> SEQ ID NO 103
<211> LENGTH: 7
<212> TYPE: PRT
<213> ORGANISM: H. sapiens

<400> SEQUENCE: 103

Ser Gln Thr Pro Ala Ala Phe
1               5

<210> SEQ ID NO 104
<211> LENGTH: 7
<212> TYPE: PRT
<213> ORGANISM: chicken

<400> SEQUENCE: 104

Gly Gln Ser Pro Ala Ala Phe
1               5

<210> SEQ ID NO 105
<211> LENGTH: 7
<212> TYPE: PRT
<213> ORGANISM: zebra fish

<400> SEQUENCE: 105

Cys Gln Thr Pro Pro Ala Pro
1               5

<210> SEQ ID NO 106
<211> LENGTH: 7
<212> TYPE: PRT
<213> ORGANISM: H. sapiens

<400> SEQUENCE: 106

Ser Gln Thr Ser Ala Ala Phe
1               5

<210> SEQ ID NO 107
<211> LENGTH: 19

<212> TYPE: DNA
<213> ORGANISM: H. sapiens

<400> SEQUENCE: 107
cagccagacg tccgcggcc                                                    19

<210> SEQ ID NO 108
<211> LENGTH: 6
<212> TYPE: PRT
<213> ORGANISM: H. sapiens

<400> SEQUENCE: 108

Ser Gln Thr Pro Ala Ala
1               5

<210> SEQ ID NO 109
<211> LENGTH: 6
<212> TYPE: PRT
<213> ORGANISM: H. sapiens

<400> SEQUENCE: 109

Ser Gln Thr Ser Ala Ala
1               5

<210> SEQ ID NO 110
<211> LENGTH: 2695
<212> TYPE: DNA
<213> ORGANISM: H. sapiens

<400> SEQUENCE: 110
aaatgcttta ctcttctcac cctaagggct cctgaattta gcttttatt acacagaacc         60 cagtaaacta attaatggaa atctaaaaat tatccttcct cttcttagaa aagaaatata       120
ctgcatgatg atttgtgctt ttcgatttaa tgtcacacaa tcgtttttac actgtatgtg       180
ctttccctcc ccacagcccc agtcccagcc ccagtctcgc agttccattc cttcagggca       240
gcttccattc taccgtgagt ttttattgct ttcccctaaa acgctgccct ggagtcgcgt       300
ttattggaca ctctttagtc tgtaaaggaa aaaacacaa acaccggagg agaatcatcc        360
taacaagccg acaacatatc tatgggccta aaaaacttaa attcttttccc gttattagca      420 cttctcgatc gttccaggaa agcccgattt gtagcttggc tgccccagga aggggcctgc       480
gaccagaaag atgcaaaggg cgggacaagg ttacgagtgg gtgcgggaa gcctccctaa        540 cctgggggcc gcgtcccaga gctgcgagcc acgcctcctc tctcccgccc gccgcgccgc       600
cggactctta ttttgaaggg cggcgggtga aggctcggag cctcctgagt cacccggcgg       660
gcgaggtata aagcccgata cctgccccgc gcccggtccg cggagcccgc tgcagctccc       720
gctcgctccg gacgcggaat cgggcagcag cggaggcgg cccggagagc cgaggtaggc        780
gcggggaatc ggccctgagg ctggtggaag aaatgtgtga attaaaggga gtgcagcgtg       840
cagggtgggc cgcgagtcgg gagtgcaggg ctcgggacag ggtgggggcg gggaggacaa       900
gagactcgtc agcgcacttt ccacccggcc ggttccttcc cgagccctct ccctcccccg       960
gcccgcggga gcacagatcc ctgaaagcgg agctccagat aggaatgtct gcatcatctt      1020
ggcagggccc agacgggaga agatgctctg ctgccacgag cgatccctcc cgctctccta      1080
actcttctct gaacacctcg caccccacg gcccccgcc cctctcttaa tcttggccac        1140
gctccctgag gggtcagacc tggggtggga gagcagagaa agcggggctg cagagacag       1200 gggtgagggc cgggagaggc gatgacatca ttccctggca gctggcgggg agagggtggg     1260

```
gacggagggg tcccccgac ctgagccgag ccctcccttc ccaagcccat cctcctttct    1320
ttgggatggt tcaccccacc tgggcgccat tcaaaggaag tttgcgcgta actcggggcg    1380
tcctttcccc ggccgggtgc tgtgcccggc ccgcagtcgg tgtttcttct gggcctgggg    1440
gcggcgtgga gccggcggct cagtcccctc agtcccaggc cttggcagcc gctttgttca    1500
cgccgggcgc gggccgaacc cgaacctcag ctgcagcact ggcagcgcgc accggccacg    1560
cgtgggttcc cggccacggc cgggccaaca agggagggtc ccgtgagcag ccaggctggc    1620
cctccccggg cctgggtgag ctcccaaagc tggagcgcag ggctctaggc cggccccgcc    1680
ccggggctgg gggcttcccg cccgtttgtc tcattttaac ttttggggc agctctgtcc    1740 cgaatggtga gtggtccaga ctctagaaag gggtttggtc gcttgagccc ggattgaggc    1800
ttgggacctt tgctctcttg ctggggacga aggggggcgc gctgggcagg agaggggcg    1860 tctcggtcgg gtctccctgg gctcgggcat cttcccaccc tgcggagccg ggtcttgcgc    1920
tgcgtgcccc gaacaggccc gggcacaccg agtcccgtta ctggtcttca ggcgaaattc    1980
caggacgggt gtgcattcat caacctggga gtctctagga gccagagatg actggctcta    2040
cattttaatg cgtaatcaca gagaaactag cacgagaaaa ggacagaggg accgacccaa    2100
gcttcagaga catggaataa tatgatcctg gttcataagc cttgaaaagc tcccctccgc    2160
caggttaagg aatggtgtca ccagccttgg ctgtgaggat aatttcttga tttgtgttat    2220
gcaggctcct gtcaggactg tctccttaac tcccactacc taaggaaaag atagccagag    2280
aattgtccag ggatttgggt ttgggttgct tctagaaaga cagcatcttt cttgctattt    2340
tttttttcac atcccccaa aacaatttt tccccttc agacttggca gactttgatt    2400
tagataagag gtttgagtta atttgatttt ccccatgtct gtttagatca atggatatag    2460
gagatagttt gaagctaatg taccccctatg cctttgtgtg agtgtaagat ttataacttg    2520
agggaggcag ttaataaata gcacatcctt gaaccataaa catacgagat agacaagagc    2580
tagataataa acagttttc ccccaatccc taagctttac ttatttttt tactgattct    2640 tgtactttgt cattagaaaa aggagtgggg ttggtttccc agtgaccgca ttcat         2695
```

<210> SEQ ID NO 111
<211> LENGTH: 1475
<212> TYPE: DNA
<213> ORGANISM: H. sapiens

<400> SEQUENCE: 111

```
cgggacaagg ttacgagtgg gtgcggggaa gcctccctaa cctggggggcc gcgtcccaga     60 gctgcgagcc acgcctcctc tctcccgccc gccgcgccgc cggactctta ttttgaaggg    120
cggcgggtga aggctcggag cctcctgagt cacccggcgg gcgaggtata aagcccgata    180
cctgccccgc gccggtccg cggatcccgc tcgctccgga cgcggaatcg ggcagcagcg    240
ggaggcggcc cggagagccg aggtaggcgc gggaatcgg ccctgaggct ggtgaagaa    300 atgtgtgaat taaagggagt gcagcgtgca gggtgggccg cgagtcggga gtgcagggct    360
cgggacaggg tgggggcggg gaggacaaga gactcgtcag cgcactttcc acccggccgg    420
ttccttcccg agccctctcc ctcccccggc ccgcgggagc acagatccct gaaagcggag    480
ctccagatag gaatgtctgc atcatcttgg cagggcccag acgggagaag atgctctgct    540
gccacggacg atccctcccg ctctcctaac tcttctctga acacctcgca ccccacggc    600 ccccgcccc tctcttaatc ttggccacgc tccctgaggg gtcagacctg gggtgggaga    660
gcagagaaag cggggctggc agagacaggg gtgagggccg ggagaggcga tgacatcatt    720
```

-continued

```
ccctggcagc tggcggggag agggtgggga cggagtggtc cccccgacct gagccgagcc    780
ctcccttccc aagcccatcc tcctttcttt gggatggttc accccacctg ggcgccattc    840
aaaggaagtt tgcgcgtaac tcgggcgtc ctttccccgg ccgggtgctg tgcccggccc     900
gcagtcggtg tttcttctgg gcctgggggc ggcgtggagc cggcggctca gtcccctcag    960
tcccaggcct tggcagccgc tttgttcacg ccgggcgcgg gccgaacccg aacctcagct   1020
gcagcactgg cagcgcgcac cggccacgcg tgggttcccg gccacggccg ggccaacaag   1080
ggagggtccc gtgagcagcc aggctggccc tccccgggcc tgggtgagct cccaaagctg   1140
gagcgcaggg ctctaggccg gccccgcccc ggggctgggg gcttcccgcc cgtttgtctc   1200
attttaactt ttgggggcag ctctgtcccg aatggtgagt ggtccagact ctagaaaggg   1260
gtttggtcgc ttgagcccgg attgaggctt gggacctttg ctctcttgct ggggacggaa   1320
gggggcgcgc tgggcaggag aggggggcgtc tcggtcgggt ctccctgggc tcgggcatct   1380
tcccaccctg cggagccggg tcttgcgctg cgtgccccga acaggcccgg gcacaccgag   1440
tcccgttact ggtcttcagg cgaaattcca ggacg                              1475
```

<210> SEQ ID NO 112
<211> LENGTH: 118
<212> TYPE: DNA
<213> ORGANISM: H. sapiens

<400> SEQUENCE: 112

```
cgggcgaggt ataaagcccg atacctgccc cgcgcccggt ccgcggagcc cgctgcagct     60
cccgctcgct ccggacgcgg aatcgggcag cagcgggagg cggcccggag agccgagg     118
```

<210> SEQ ID NO 113
<211> LENGTH: 22
<212> TYPE: DNA
<213> ORGANISM: Artificial Sequence
<220> FEATURE:
<223> OTHER INFORMATION: synthetic probe

<400> SEQUENCE: 113

```
gcggagcccg ctgcagctcc cg                                              22
```

<210> SEQ ID NO 114
<211> LENGTH: 20
<212> TYPE: DNA
<213> ORGANISM: Artificial Sequence
<220> FEATURE:
<223> OTHER INFORMATION: synthetic probe

<400> SEQUENCE: 114

```
cggagcccgc tgcagctccc                                                 20
```

<210> SEQ ID NO 115
<211> LENGTH: 20
<212> TYPE: DNA
<213> ORGANISM: Artificial Sequence
<220> FEATURE:
<223> OTHER INFORMATION: synthetic primer

<400> SEQUENCE: 115

```
ccccgcgccc ggtccgcgga                                                 20
```

<210> SEQ ID NO 116
<211> LENGTH: 20
<212> TYPE: DNA

```
<213> ORGANISM: Artificial Sequence
<220> FEATURE:
<223> OTHER INFORMATION: synthetic primer

<400> SEQUENCE: 116
cgcgtccgga gcgagcggga                                              20
```

COMPOSITIONS AND METHODS FOR DETECTING CANCER

CROSS-REFERENCE

This application is a divisional of U.S. patent application Ser. No. 11/840,112, filed Aug. 16, 2007, issued on Dec. 14, 2010 as U.S. Pat. No. 7,851,144, which application claims the benefit of U.S. Provisional Patent Application No. 60/838,746, filed Aug. 18, 2006. These applications are incorporated herein by reference in their entirety.

STATEMENT REGARDING FEDERALLY SPONSORED RESEARCH

This invention was made with U.S. government support under grant numbers GM061743 and NS043253, awarded by the National Institutes of Health. The U.S. government has certain rights in the invention.

BACKGROUND

Pancreatic cancer is the fourth leading cause of cancer death in the United States. It is difficult to detect, early to metastasize and resistant to treatment. Nearly every person diagnosed with pancreatic cancer will die from it, usually within 12 months of diagnosis. Familial clustering of pancreatic cancers is commonly recognized, occurring in at least 10% of all pancreatic cancer. The risk of pancreatic cancer increases further with each family member who is affected.

Current methods for diagnosing pancreatic cancer include computed tomography scanning, magnetic resonance imaging, positron emission tomography scanning, endoscopic ultrasonography, laparoscopy, endoscopic retrograde cholangiopancreatography, percutaneous transhepatic cholangiography, and biopsy.

Early detection and diagnosis are important for the successful treatment of cancer in general. Despite advances in detection of various cancers, there is an ongoing need for diagnostic methods and tools for detection of cancers. In particular, there is a need in the art for methods of detecting pancreatic cancer.

LITERATURE

U.S. Pat. No. 6,642,009; Parast and Otey (2000) *J. Cell Biol.* 150:643-655; Mykkänen et al. (2001) *Molec. Biol. Cell* 12:3060-3073; Boukhelifa et al. (2001) *Molec. Biol. Cell* 12:2721-2729; Boring et al. (1994) *CA Cancer J Clin* 44:7-26; Hruban et al. (1999) *Annals of Oncology* 10 Suppl 4:69-73; Silverman et al. (1999) *British Journal of Cancer* 80:1830-7; Eberle et al. (2002) *Am J Hum Genet*, 70:1044-8; Ghadirian et al. (1991) *Int J Pancreatol* 10:183-96; Lynch et al. (1996) *Semin Onocol.* 23:251-75; Pohl et al. (2005) *Cancer Res.* 65:1994; Rachlin and Otey (2006) *J. Cell Sci.* 119: 995-1004; WO 04/016809; WO 03/025138; WO 02/059377; U.S. Patent Publication No. 2004/0029114; WO 06/017635; WO 05/094306; WO 06/002433; U.S. Patent Publication No. 2006/0024692; WO 04/031413; WO 04/031410; U.S. Patent Publication No. 2004/0076955; WO 03/039443.

SUMMARY OF THE INVENTION

The present invention provides methods and compositions involving detecting the presence of and/or assessing the risk of cancer in a subject. These methods include methods of detecting and diagnosing cancer in an individual; methods of identifying individuals at risk of developing a cancer; and methods of staging a cancer. The methods generally involve detecting a palladin gene nucleotide sequence alteration that has been found to be associated with cancer and/or detecting a level of a palladin mRNA and/or protein in a biological sample. The present invention further provides nucleic acid probes, nucleic acid primers, and antibodies, as well as kits comprising one or more of the same, for use in a subject method.

BRIEF DESCRIPTION OF THE DRAWINGS

FIGS. 1A and 1B provide a nucleotide sequence (AB023209; SEQ ID NO:1) of an mRNA encoding palladin. Mutations associated with pancreatic cancer are underlined and in bold text.

FIGS. 3A-C depict identification of 4q32-34 genes differentially expressed in sporadic pancreatic cancer and in Family X pre-cancer.

FIG. 5 depicts an alignment of actinin binding site amino acid sequences of palladin from various species (human, chimp, mouse, rat: SEQ ID NO:103; chicken: SEQ ID NO:104; zebra fish: SEQ ID NO:105; and Family X: SEQ ID NO:106). The Pro→Ser substitution is boxed.

FIG. 10 depicts an exemplary palladin target nucleic acid (SEQ ID NO:63). The sequence corresponds to nucleotides 621-780 of a SEQ ID NO:1, and includes a C→T substitution (in bold and underlined) at a position corresponding to nucleotide 715 in SEQ ID NO:1. FIG. 10 also depicts an exemplary primer pair (SEQ ID NOs:64 and 65) for amplifying the exemplary target nucleic acid.

FIG. 11 depicts a palladin amino acid sequence (BAA76836.1; SEQ ID NO:99). Mutations associated with pancreatic cancer are underlined and in bold text.

FIG. 12 depicts a palladin amino acid sequence (NP_057165.3; SEQ ID NO:87).

FIGS. 13A and 13B depict a palladin mRNA nucleotide sequence (NM_016081; SEQ ID NO:20).

FIG. 14 depicts a genomic DNA sequence from GenBank Accession No. AC080188 (*Homo sapiens* BAC clone RP11-635L1; SEQ ID NO:101), including exon 9 sequences (depicted in bold text). Nucleotide 183561 (underlined and in bold text) corresponds to nucleotide 1671 of SEQ ID NO:1.

FIG. 15 depicts a genomic DNA sequence from GenBank Accession No. AC084353 (*Homo sapiens* BAC clone RP11-592K15; SEQ ID NO:102), including nucleotide 27251 (underlined and in bold text), which corresponds to nucleotide 2060 of the sequence depicted in FIG. 12.

FIG. 16 depicts a genomic DNA sequence from GenBank Accession No. AC080188 (*Homo sapiens* BAC clone RP11-

635L1, including exon 2 sequences (depicted in bold text). Nucleotide 140301 (underlined and in bold text) corresponds to nucleotide 715 of SEQ ID NO:1.

Figure 17:
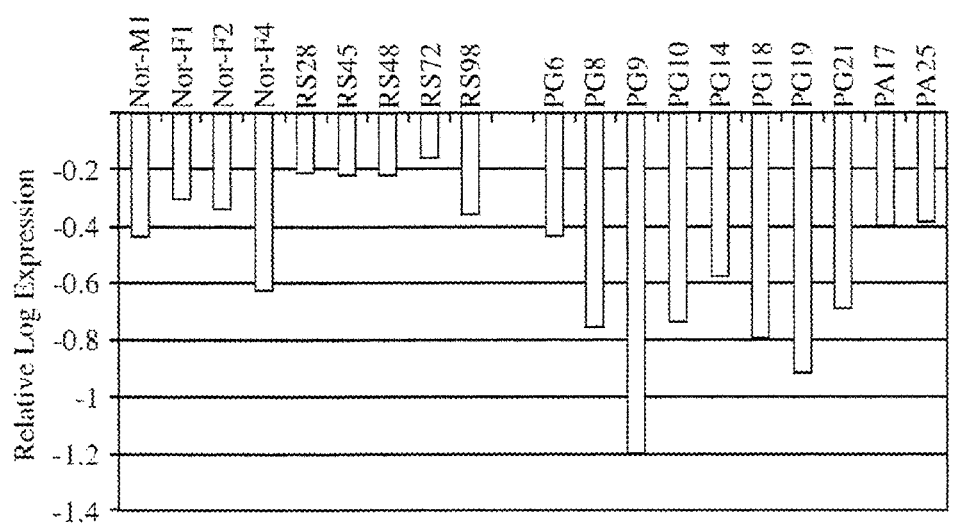

FIG. 17 depicts relative log expression, normalized to GAPDH and to a standard sample using the ddCt method, of palladin mRNA in white blood cells from normal individuals ("Nor" and "RS"), and individuals with pancreatic cancer ("PG" or "PA").

Figure 18:
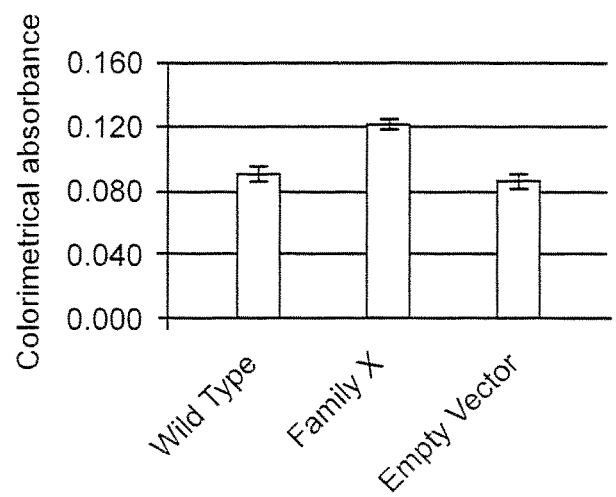

FIG. 18 depicts the effect of palladin mutation on cell mobility.

FIG. 19 depicts the nucleotide sequence of a palladin 90 kDa isoform promoter, including a 12-base pair insertion. The promoter sequence is boxed; the 12-bp insertion is in bold.

DEFINITIONS

The terms "polynucleotide," "oligonucleotide," "nucleic acid" and "nucleic acid molecule" are used interchangeably herein to include a polymeric form of nucleotides, either ribonucleotides or deoxyribonucleotides. The terms refer only to the primary structure of the molecule. Thus, the terms include triple-, double- and single-stranded DNA, as well as triple-, double- and single-stranded RNA. RNA includes, e.g., messenger RNA. The terms "polynucleotide," "oligonucleotide," "nucleic acid" and "nucleic acid molecule" also include modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (C or T (U)); S=C or G; W=A or T (U); M=A or C; K=G or T (U); V=A, C or G; and N=any nucleotide (A, T (U), C, or G). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides.

The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention. Usually two sequences are sufficiently complementary when at least about 85%, at least about 90%, at least about 95%, or at least about 98% of the nucleotides share base pair organization over a defined length of the molecule.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which the recited material is unaccompanied by at least some of the material with which it is normally associated in its natural state, where the isolated compound constitutes at least about 50%, at least about 75%, or at least about 90%, or more, by weight of the total protein in a given sample. For example, the term "isolated" with respect to a polynucleotide generally refers to a nucleic acid molecule devoid, in whole or part, of sequences normally associated with it in nature; or a sequence, as it exists in nature, but having heterologous sequences in association therewith; or a molecule disassociated from the chromosome.

"Purified" as used herein means that the recited material comprises at least about 75%, at least about 80%, or at least about 90% by weight of the total material. As used herein, the term "substantially pure" refers to a compound that is removed from its natural environment and is at least 60% free, at least 75% free, at least 90% free, at least 95% free, at least 98% free, or at least 99% or more free, from other components with which it is naturally associated.

A polynucleotide "derived from" or "specific for" a designated sequence, such as a target sequence of a target nucleic acid, refers to a polynucleotide sequence which comprises a contiguous sequence of approximately at least about 6 nucleotides, at least about 8 nucleotides, at least about 10-12 nucleotides, or at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from" or "specific for" a designated sequence include polynucleotides that are in a sense or an antisense orientation relative to the original polynucleotide.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms.

Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples. In many embodiments, a biological sample will include cells (e.g., pancreatic cells; non-pancreatic cells).

In some embodiments, a biological sample will include tissue. In some embodiments, a biological sample will include RNA (e.g., mRNA) obtained from cells or tissue; a cDNA copy of an RNA obtained from cells or tissues; an amplified copy of an mRNA or a cDNA obtained from cells or tissues; and the like. In some embodiments, a biological sample will include genomic DNA obtained from cells or tissue. The tissue may appear histologically normal, or may appear histologically abnormal (e.g., neoplastic).

In some embodiments, a biological sample will include tissue (e.g., pancreatic tissue; non-pancreatic tissue). In some embodiments, a biological sample will include RNA (e.g., mRNA) obtained from cells or tissue (e.g., pancreatic cells; non-pancreatic cells; pancreatic tissue; non-pancreatic tissue); a cDNA copy of an RNA obtained from cells or tissues; an amplified copy of an mRNA or a cDNA obtained from cells or tissues; and the like. In some embodiments, a biological sample will include genomic DNA obtained from cells or tissue (e.g., pancreatic cells; non-pancreatic cells; pancreatic tissue; non-pancreatic tissue).

An "indicator cell" as used herein is a cell which is subjected to analysis for a parameter that is indicative of the presence of cancer in a subject from whom the indicator cell was obtained. Where the parameter is the presence or absence of a palladin mutation, the indicator cell is a cell from blood or a tissue suspected of containing a pre-cancerous or cancerous cell having a palladin mutation (e.g., pancreatic cell, breast cell, head and neck squamous cell, and the like). Where the parameter is the presence or absence of an aberrant expression level of palladin, the indicator cell can be a cell from blood or a tissue suspected of having an aberrant expression level of palladin or a cell other than a cancerous or pre-cancerous cell, e.g., a white blood cell. "Indicator cell" as used herein is most often used in the context of detection of palladin expression levels in a white blood cell, but could represent any cell in the body.

A "DNA-dependent DNA polymerase" is an enzyme that synthesizes a complementary DNA copy from a DNA template. Examples include DNA polymerase I from *E. coli* and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

A "DNA-dependent RNA polymerase" or a "transcriptase" is an enzyme that synthesizes multiple RNA copies from a double-stranded or partially-double stranded DNA molecule having a (usually double-stranded) promoter sequence. The RNA molecules ("transcripts") are synthesized in the 5' to 3' direction beginning at a specific position just downstream of the promoter. Examples of transcriptases are the DNA-dependent RNA polymerase from *E. coli* and bacteriophages T7, T3, and SP6.

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

"RNAse H" is an enzyme that degrades the RNA portion of an RNA:DNA duplex. These enzymes may be endonucleases or exonucleases. Most reverse transcriptase enzymes normally contain an RNAse H activity in addition to their polymerase activity. However, other sources of the RNAse H are available without an associated polymerase activity. RNA degradation mediated by an RNAse H may result in separation of RNA from a RNA:DNA complex, or the RNAse H may cut the RNA at various locations such that portions of the RNA melt off or permit enzymes to unwind portions of the RNA.

As used herein, the term "target nucleic acid region" or "target nucleic acid" or "target molecules" refers to a nucleic acid molecule with a "target sequence" to be detected (e.g., in a method involving nucleic acid hybridization and/or amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" refers to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with its use in synthesis of primer extension products, and are in many embodiments in the range of between 8 nucleotides and 100 nucleotides (nt) in length, such as 10 nt to 75 nt, 15 nt to 60 nt, 15 nt to 40 nt, 18 nt to 30 nt, 20 nt to 40 nt, 21 nt to 50 nt, 22 nt to 45 nt, 25 nt to 40 nt, and so on, e.g., in the range of between 18 nt and 40 nt, between 20 nt and 35 nt, between 21 and 30 nt in length, inclusive, and any length between the stated ranges. Primers can be in the range of between 10-50 nucleotides long, such as 15-45, 18-40, 20-30, 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Primers are in many embodiments single-stranded for maximum efficiency in amplification, but may alternatively be double-stranded. If double-stranded, the primer is in many embodiments first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are in many embodiments in the range of between 8 nt and 100 nt in length, such as 8 to 75 nt, 10 to 74 nt, 12 to 72 nt, 15 to 60 nt, 15 to 40 nt, 18 to 30 nt, 20 to 40 nt, 21 to 50 nt, 22 to 45 nt, 25 to 40 nt in length, and so on, e.g., in the range of between 18-40 nt, 20-35 nt, or 21-30 nt in length, and any length between the stated ranges. In some embodiments, a probe is in the range of between 10-50 nucleotides long, such as 15-45, 18-40, 20-30, 21-28, 22-25 and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. For example, when an "oligonucleotide probe" is to be used in a 5' nuclease assay, such as the TAQMAN™ assay, the probe includes at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

Probes and primers contemplated herein include those useful in various amplification and/or detection systems, including those in which primers and probes are provided as bi-functional molecules. Exemplary amplification and/or detection systems include Sunrise™ primer-based systems, Molecular Beacons, the Taqman™ system, an Amplifluor™ hairpin primer-based system, a Scorpions technology (e.g., bi-functional molecules containing a PCR primer element covalently linked to a probe element), and a Light Upon Extension or LUX™-based system. Further exemplary detection systems include those based on a melt-curve analysis, and using intercalating dyes such as the fluorescent dye SYBR Green.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens), intercalating dyes and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

The term "assessing" includes any form of measurement, and includes determining if an element is present or not. The terms "determining," "measuring," "evaluating," "assessing," and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The term "binds specifically," in the context of antibody binding, refers to high avidity and/or high affinity binding of an antibody to a specific polypeptide i.e., epitope of a polypeptide, e.g., a palladin polypeptide. For example, antibody binding to an epitope on a specific a subject deacylase or fragment thereof is stronger than binding of the same antibody to any other epitope, particularly those which may be present in molecules in association with, or in the same sample, as the specific polypeptide of interest, e.g., binds more strongly to a specific palladin polypeptide than to any other palladin epitopes so that by adjusting binding conditions the antibody binds almost exclusively to the specific palladin epitope and not to any other palladin epitope, or to any other polypeptide which does not comprise the epitope. Antibodies that bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a palladin polypeptide, e.g. by use of appropriate controls. In general, specific antibodies bind to a given polypeptide with a binding affinity of $10^{-7}$ M or more, e.g., $10^{-8}$ M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

The terms "cancer," "neoplasm," and "tumor" are used interchangeably herein to refer to cells that exhibit relatively autonomous growth, so that they exhibit an aberrant growth phenotype characterized by a significant loss of control of cell proliferation. Cancerous cells can be benign or malignant.

The terms "individual," "host," "subject," and "patient," used interchangeably herein, refer to a mammal, including human and non-human primates; rodents (e.g., mice, rats, etc.); livestock (e.g., bovine, ovine, caprine, porcine, etc., mammals); mammalian pets (e.g, canines, felines, etc.); horses; lagomorphs; etc. In some embodiments, an individual is a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a nucleic acid probe" includes a plurality of such probes and reference to "the nucleic acid primer pair" includes reference to one or more nucleic acid primer pairs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods for detecting and diagnosing cancer in an individual; methods of identifying individuals at risk of developing a cancer; and methods of staging a cancer and/or metastases. The methods generally involve detecting a palladin gene nucleotide sequence alteration (e.g., a substitution, an insertion, a deletion, a change in methylation status, etc.) that has been found to be associated with cancer and/or detecting a level of a palladin mRNA or palladin polypeptide in a cell or tissue. The present invention further provides nucleic acid probes and nucleic acid primers, as well as kits comprising same, for use in a subject method. It is to be understood that this invention is not limited to the particular methods and materials described herein.

The present invention provides, for example, methods for detecting and diagnosing pancreatic cancer in an individual; methods of identifying individuals at risk of developing pancreatic cancer; and methods of staging pancreatic cancer. The methods generally involve detecting a palladin gene nucleotide sequence alteration that has been found to be associated with pancreatic cancer and/or detecting a level of a palladin mRNA or palladin polypeptide in a cell or tissue. The present invention further provides nucleic acid probes and nucleic acid primers, as well as kits comprising same, for use in a subject method.

The following observations were made: 1) a C→T nucleotide substitution at position 715 of the human palladin gene is associated with increased risk of developing pancreatic cancer; 2) a G→T nucleotide substitution at position 1671 of the human palladin gene is associated with increased risk of developing pancreatic cancer; 3) a C→T nucleotide substitution at position 2060 of the human palladin gene is associated with cancerous phenotype in pancreatic cells; 4) palladin mRNA, e.g., palladin mRNA that encodes the 90 kD isoform of palladin, is overexpressed in pre-cancerous and pancreatic cells; 5) the level of palladin mRNA, e.g., palladin mRNA that encodes the 90 kD isoform of palladin, in a pancreatic cell increases with neoplastic progression; 6) lower than normal levels of palladin mRNA in white blood cells is associated with pancreatic cancer; 7) palladin mRNA is abnormally expressed in a variety of cancers; and 8) a 12-base pair insertion in the promoter of the 90 kDa isoform of palladin is associated with an increased risk of developing pancreatic cancer.

Cancers that can be detected and/or diagnosed using a subject method include, but are not limited to, pancreatic cancer, breast cancer, and head and neck squamous cell carcinoma.

Methods for detecting a cancerous or precancerous cell, e.g., a cancerous or precancerous pancreatic cell, as well as methods for identifying individuals at risk of developing a cancer such as pancreatic cancer, may involve detecting a nucleotide substitution in a palladin target nucleic acid (such as palladin genomic DNA; palladin mRNA; a cDNA copy of a palladin mRNA; an amplified copy of a palladin mRNA or cDNA) present in a biological sample. Examples of palladin gene nucleotide substitutions associated with a cancerous or precancerous cell (e.g., a precancerous pancreatic cell, a cancerous pancreatic cell) and/or an increased risk of developing cancer (e.g., pancreatic cancer) include the following: 1) a C→T nucleotide substitution at position 715 of AB023209 (see, e.g., FIG. 1A); 2) a G→T nucleotide substitution at position 1671 of AB023209 (see, e.g., FIG. 1A); and 3) a C→T nucleotide substitution at position 2060 of NM-016081 (see, e.g., FIGS. 13A and 13B). Mutations in palladin, however, are not limited to the ones listed herein.

Methods for detecting a cancerous or precancerous cell, e.g., a cancerous or precancerous pancreatic cell, as well as methods for identifying individuals at risk of developing a cancer such as pancreatic cancer, can also involve detecting an insertion in a palladin target nucleic acid (such as palladin genomic DNA; palladin mRNA; a cDNA copy of a palladin mRNA; an amplified copy of a palladin mRNA or cDNA) present in a biological sample. Examples of palladin gene nucleotide sequence insertions associated with a cancerous or precancerous cell (e.g., a precancerous pancreatic cell, a cancerous pancreatic cell) and/or an increased risk of developing cancer (e.g., pancreatic cancer) include an insertion in the promoter region of the gene encoding the 90 kDa isoform of palladin.

Methods for detecting a cancerous or precancerous cell, e.g., a cancerous or precancerous pancreatic cell, as well as methods for identifying individuals at risk of developing a cancer such as pancreatic cancer, can also involve detecting a change in the methylation status of palladin target nucleic acid (such as palladin genomic DNA; palladin mRNA; a cDNA copy of a palladin mRNA; an amplified copy of a palladin mRNA or cDNA) present in a biological sample. For example, hypomethylation of a palladin gene promoter associated with a cancerous or precancerous cell (e.g., a precancerous pancreatic cell, a cancerous pancreatic cell) and/or an increased risk of developing cancer (e.g., pancreatic cancer).

Detection of a nucleotide sequence alteration in a palladin target nucleic acid can be carried out using, e.g., nucleic acid hybridization with a nucleic acid probe specific for the nucleotide substitution. Detection of a nucleotide sequence alteration in a palladin target nucleic acid can also be carried out by first amplifying a target palladin nucleic acid that comprises the nucleotide substitution, using a nucleic acid primer pair; then detecting the nucleotide substitution by hybridization with a nucleic acid probe.

For example, detection of the 715 C→T nucleotide substitution can be carried out using, e.g., nucleic acid hybridization with a nucleic acid probe specific for the 715 C→T nucleotide substitution. Detection of the 715 C→T nucleotide substitution can also be carried out by first amplifying a target palladin nucleic acid that comprises the 715 C→T nucleotide substitution, using a nucleic acid primer pair; then detecting the 715 C→T nucleotide substitution by hybridization with a nucleic acid probe.

Methods for detecting a cancerous or precancerous cell, as well as methods of staging a cancer, may involve detecting a level of palladin mRNA present in a biological sample (for example, a cell, or a biological sample comprising a cell). Detecting a level of palladin mRNA present in a cell may involve nucleic acid hybridization with a nucleic acid probe that detects a target palladin nucleic acid that is overexpressed in a cancerous cell (e.g., a cancerous pancreatic cell). Detecting a level of palladin mRNA present in a cell may involve nucleic acid hybridization with a nucleic acid probe that detects a target palladin nucleic acid that is expressed at lower than normal levels in an indicator cell, e.g., a cell other than a cancer cell. Detecting a level of palladin mRNA can also be carried out using any of a variety of nucleic acid amplification methods, e.g., a quantitative polymerase chain reaction or other nucleic acid amplification method.

Methods for detecting a cancerous or precancerous cell, as well as methods of staging a cancer, may involve detecting a level of palladin protein/polypeptide present in a biological sample. Detecting a level of palladin protein/polypeptide present in a cell or tissue or fluid may involve protein binding with a antibody probe that detects a target palladin protein that is overexpressed in a pre-cancerous or cancerous biologic sample (for example, cancerous pancreatic tissue). Examples of methods for protein detection include, but are not limited, to Western Blotting, enzyme-linked immunosorbent assays, immunostaining, and in-situ hybridization. Other methods of detecting polypeptides include direct detection through the use of proteomics, such as mass spectroscopy measurements, and the like.

As discussed above, subject detection, diagnostic, and staging methods generally involve nucleic acid hybridization, and/or nucleic acid amplification, and/or protein detection. The present invention provides nucleic acid probes and nucleic acid primers that are suitable for use in such methods. In some embodiments, nucleic acid probes and nucleic acid primer pairs are useful for detecting a palladin nucleic acid comprising a nucleotide sequence alteration that is associated with pancreatic cancer. In other embodiments, nucleic acid probes and nucleic acid primer pairs are useful for detecting a palladin nucleic acid that is over-expressed in a pancreatic cell. Probes and primers useful in detecting a palladin nucleic acid comprising a nucleotide substitution can also be used in detecting palladin expression levels. Kits that include a nucleic acid probe, a nucleic acid primer pair, an antibody reagent, or two or more of the foregoing, are also provided.

Target Nucleic Acids

Target palladin nucleic acids include palladin nucleic acids that include one or more palladin gene nucleotide sequence alterations (e.g., substitutions, deletions, insertions, etc.) that are associated with an increased risk of developing cancer (e.g., pancreatic cancer, breast cancer, head and neck squamous cell carcinoma, etc.) and/or are associated with a precancerous or cancerous state of a cell such as a pancreatic cell and/or are indicative of the presence of a cancerous cell in the individual. For example, a palladin gene nucleotide sequence alteration will in some cases be associated with abnormal levels of palladin mRNA and/or polypeptide in a pancreatic cell.

In some embodiments, abnormal levels of a palladin mRNA that, when present in a cell, are associated with a precancerous or cancerous state of the cell, are levels that are significantly higher or lower than normal levels of the palladin mRNA found in a non-cancerous cell of the same cell type. In some embodiments, abnormal levels of a palladin mRNA that, when present in a test cell, are indicative of the presence of a cancerous cell in the individual from whom the test cell was obtained, are levels that are significantly higher or lower than normal levels of the palladin mRNA typically found in the test cell in an individual who does not have cancer.

An abnormally high level of a palladin mRNA that, when present in a cell, is associated with a precancerous or cancerous state of the cell, is a level that is at least about 25%, at least about 50%, at least about 100% (or 2-fold), at least about 3-fold, at least about 5-fold, at least about 10-fold, at least about 25-fold, or at least about 50-fold, or more, higher than the level of the palladin mRNA in a non-cancerous cell of the same cell type.

For example, an abnormally high level of a palladin mRNA that, when present in a pancreatic cell, is associated with a precancerous or cancerous state of the cell, is a level that is at least about 25%, at least about 50%, at least about 100% (or 2-fold), at least about 3-fold, at least about 5-fold, at least about 10-fold, at least about 25-fold, or at least about 50-fold, or more, higher than the level of the palladin mRNA in a non-cancerous pancreatic cell.

An abnormally low level of a palladin mRNA that, when present in a cell, is associated with a precancerous or cancerous state of the cell, is a level that is about 75% or less, about 60% or less, about 50% or less, about 25% or less, or about 10% or less, than the level of the palladin mRNA in a non-cancerous cell of the same cell type For example, an abnormally low level of a palladin mRNA that, when present in a pancreatic cell, is associated with a precancerous or cancerous state of the cell, is a level that is about 75% or less, about 60% or less, about 50% or less, about 25% or less, or about 10% or less, than the level of the palladin mRNA in a non-cancerous pancreatic cell.

An abnormally low level of a palladin mRNA that, when present in a test cell (also referred to as an "indicator cell"), is indicative of the presence of a cancerous cell in the individual from whom the test cell was obtained, is a level that is about 75% or less, about 60% or less, about 50% or less, about 25% or less, or about 10% or less, than the level of the palladin mRNA typically found in the test cell in an individual who does not have cancer. As one non-limiting example, it was found that the level of palladin mRNA in white blood cells (WBC) from individuals with pancreatic cancer was abnormally low when compared to the level of palladin mRNA present in WBC from normal individuals (e.g., individuals without pancreatic cancer).

Non-limiting examples of palladin gene nucleotide substitutions associated with a precancerous or cancerous cell (e.g., a precancerous pancreatic cell, a cancerous pancreatic cell) and/or an increased risk of developing a cancer such as pancreatic cancer include the following: 1) a C→T nucleotide substitution at position 715 of AB023209 (see, e.g., FIG. 1A); 2) a G→T nucleotide substitution at position 1671 of AB023209 (see, e.g., FIG. 1A); and 3) a C→T nucleotide substitution at position 2060 of NM-016081 (see, e.g., FIGS. 13A and 13B).

It should be noted that in the diagnostic methods based on detection of palladin mutations or palladin expression levels, while detection of a palladin mutation and/or aberrant (abnormal) palladin expression levels indicates the presence of a cancerous or pre-cancerous cell in the subject, the detection of the absence of a palladin mutation or the absence of aberrant (abnormal) expression levels does not necessarily indicate the absence of a cancerous or pre-cancerous state.

715 C→T Nucleotide Substitution

Target palladin nucleic acids include palladin nucleic acids that include the 715 C→T substitution; and palladin nucleic acids that are overexpressed in cancerous and precancerous cells (e.g., cancerous and precancerous pancreatic cells). A target palladin nucleic acid that is overexpressed in a cancerous or a precancerous cell (e.g., a cancerous or a precancerous pancreatic cell) may or may not include the 715 C→T substitution. In some embodiments, a target palladin nucleic acid that is overexpressed in a cancerous or precancerous cell (e.g., a cancerous or a precancerous pancreatic cell) is a palladin mRNA that encodes the 90 kD isoform of palladin. In some embodiments, a target palladin nucleic acid that is overexpressed in a cancerous or a precancerous cell (e.g., a cancerous or a precancerous pancreatic cell) includes nucleotide sequences found in exon 2 of the palladin gene, e.g., all or part of the sequence depicted in nucleotides 132 through 803 of the sequence shown in FIG. 1A.

In some embodiments, a nucleic acid probe hybridizes to and provides for detection of a palladin nucleic acid comprising a nucleotide substitution that is associated with cancer (e.g., pancreatic cancer). In some embodiments, a nucleotide substitution associated with cancer (e.g., pancreatic cancer) is a C-to-T (C→T) substitution at a location corresponding to nucleotide 715 of SEQ ID NO:1. As depicted in FIG. 1, the underlined and bolded "C" at position 715 is the wild-type sequence; substitution of the C at position 715 with a T is associated with cancer (e.g., pancreatic cancer). In some embodiments, the target nucleic acid is a palladin mRNA, e.g., a C→T substitution at a position corresponding to nucleotide 715 of SEQ ID NO:1 is detected in a palladin mRNA. In other embodiments, the target nucleic acid is a cDNA, e.g., a C→T substitution at a position corresponding to nucleotide 715 of SEQ ID NO:1 is detected in a cDNA copy of a palladin mRNA. In other embodiments, the target nucleic acid is genomic DNA, e.g., a C→T substitution at a position corresponding to nucleotide 715 of SEQ ID NO:1 is detected in palladin genomic DNA, e.g., exon 2 of the palladin gene. For example, a genomic DNA comprising exon 2 sequences and including nucleotide 140301 of the sequence set forth in GenBank Accession No. AC080188 (corresponding to nucleotide 715 of SEQ ID NO:1) is depicted in FIG. 16.

In some embodiments, the target nucleic acid comprises a nucleotide sequence that has at least about 70%, at least about 75%, at least about 80%, at least about 85%, at least about 90%, at least about 95%, or at least about 98% nucleotide sequence identity with a stretch of at least about 25, at least about 50, at least about 100, at least about 150, at least about 200, at least about 250, at least about 300, at least about 350, at least about 400, at least about 450, at least about 500, at least about 550, at least about 600, or at least about 670 contiguous nucleotides of nucleotide 132 to nucleotide 803 of SEQ ID NO:1 (or a complement thereof), which is an exon that includes the C→T substitution at position 715.

In some embodiments, the target nucleic acid comprises a nucleotide sequence of from about nucleotide 132 to about nucleotide 803 of SEQ ID NO:1 (or a complement thereof). In some embodiments, the target nucleic acid comprises from about nucleotide 132 to about nucleotide 802, from about nucleotide 135 to about nucleotide 800, from about nucleotide 140 to about nucleotide 800, from about nucleotide 150 to about nucleotide 800, from about nucleotide 175 to about nucleotide 800, from about nucleotide 200 to about 800, from about nucleotide 250 to about nucleotide 800, from about nucleotide 300 to about nucleotide 800, from about nucleotide 350 to about nucleotide 800, from about nucleotide 400 to about nucleotide 800, from about 450 to about nucleotide 800, from about nucleotide 500 to about nucleotide 800, from about nucleotide 550 to about nucleotide 800, from about nucleotide 600 to about nucleotide 800, from about nucleotide 650 to about nucleotide 800, or from about nucleotide 700 to about nucleotide 800 of SEQ ID NO:1, or the complement of any of the foregoing. In some embodiments, the target nucleic acid will comprise a C at a position corresponding to nucleotide 715 of SEQ ID NO:1; in other embodiments, the target nucleic acid will comprise a T at a position corresponding to nucleotide 715 of SEQ ID NO:1.

In some embodiments, the target nucleic acid comprises a nucleotide sequence of from about nucleotide 132 to about nucleotide 802 of SEQ ID NO:1 (or a complement thereof). In some embodiments, the target nucleic acid comprises from about nucleotide 132 to about nucleotide 802, from about nucleotide 135 to about nucleotide 750, from about nucleotide 140 to about nucleotide 750, from about nucleotide 150 to about nucleotide 750, from about nucleotide 175 to about nucleotide 750, from about nucleotide 200 to about 750, from about nucleotide 250 to about nucleotide 750, from about nucleotide 300 to about nucleotide 750, from about nucleotide 350 to about nucleotide 750, from about nucleotide 400 to about nucleotide 750, from about 450 to about nucleotide 750, from about nucleotide 500 to about nucleotide 750, from about nucleotide 550 to about nucleotide 750, from about nucleotide 600 to about nucleotide 750, from about nucleotide 650 to about nucleotide 750, from about nucleotide 700 to about nucleotide 750 of SEQ ID NO:1, or the complement of any of the foregoing. In some embodiments, the target nucleic acid will comprise a C at a position corresponding to nucleotide 715 of SEQ ID NO:1; in other embodiments, the target nucleic acid will comprise a T at a position corresponding to nucleotide 715 of SEQ ID NO:1.

In some embodiments, the target nucleic acid comprises a nucleotide sequence of from about nucleotide 132 to about nucleotide 803 of SEQ ID NO:1 (or a complement thereof). In some embodiments, the target nucleic acid comprises from about nucleotide 132 to about nucleotide 803, from about nucleotide 135 to about nucleotide 725, from about nucleotide 140 to about nucleotide 725, from about nucleotide 150 to about nucleotide 725, from about nucleotide 175 to about nucleotide 725, from about nucleotide 200 to about nucleotide 725, from about nucleotide 250 to about nucleotide 725, from about nucleotide 300 to about nucleotide 725, from about nucleotide 350 to about nucleotide 725, from about nucleotide 400 to about nucleotide 725, from about 450 to about nucleotide 725, from about nucleotide 500 to about nucleotide 725, from about nucleotide 550 to about nucleotide 725, from about nucleotide 600 to about nucleotide 725, from about nucleotide 650 to about nucleotide 725, from about nucleotide 675 to about nucleotide 725, or from about nucleotide 700 to about nucleotide 725 of SEQ ID NO:1, or the complement of any of the foregoing. In some embodiments, the target nucleic acid will comprise a C at a position corresponding to nucleotide 715 of SEQ ID NO:1; in other embodiments, the target nucleic acid will comprise a T at a position corresponding to nucleotide 715 of SEQ ID NO:1.

In some embodiments, a suitable target nucleic acid comprises at least the sequence 5'-GACGCCCGCG-3' (SEQ ID NO:2), or a complement thereof, or at least the sequence 5'-GACGTCCGCG-3' (SEQ ID NO:3), or a complement thereof, where the bold and underlined nucleotides represent alternative residues at a position corresponding to 715 of SEQ ID NO:1. In some embodiments, a suitable target nucleic acid comprises at least the sequence 5'-GCCACGGCCAGACG CCCGCGGCCTTCCTCA-3' (SEQ ID NO:4), or the complement thereof, or at least the sequence 5'-GCCACG-GCCAGACGTCCGCGGCCTTCCTCA-3' (SEQ ID NO:5), where the bold and underlined nucleotides represent alternative residues at a position corresponding to 715 of SEQ ID NO:1.

In one non-limiting exemplary embodiment, the target nucleic acid comprises Target Region 1, where Target Region 1 is:

5'-ggacctctgaagctccagcaactcca-gaaccaaatccgactggagcaggaggccggcgctcgg cagcctccgccagc-cccgcgcagcgcgccgccctcgcccccttcccgccgccgcccgccttcc ccgagctcgcggcctgcacgccgc-ccgcgtcccggagcccatgagcgcgctggcctcccgctc cgccccgccatg-cagtcctccggctccttcaactacgcgcgccccaagcagttcatcgccgcg cagaacctcgggcccgcgtcgggccacg-gcacgccggcctccagcccagctcgtccagcctcc cgtcgcccatgtc-cccgacgccgaggcagttcggccgcgcccccgtgccgcccttcgcgcagcc cttcggcgctgagcccgaggc-cccgtggggctcctcctcgccgtcgcccccgccccccgccaccc ccggtct-tcagccccacggctgccttcccggtgc-ccgacgtgttcccactgccgccgccaccac cgccgctcccgagcccgggacaggcgtc-ccactgctcgtcgcctgccaccccgcttcggccacgg ccagacg Tccgcggccttcctcagcgctctgctgccctcgcagccgccgccggcgg-ccgtcaac gccctggggctgcccaagggtgtcaccccgc-3' (SEQ ID NO:6; corresponding to nucleotides 132-803 of SEQ ID NO:1, but including the C→T substitution, shown in bold and underlined), or the complement thereof.

In one non-limiting exemplary embodiment, the target nucleic acid comprises Target Region 1a, where Target Region 1a is:

5'-caccgccgctcccgagcccgggacag-gcgtcccactgctcgtcgcctgccaccccgcttcggcca cggccagacg Tccgcggccttcctcagcgctctgctgccctcgcagccgccgccggcggccgtc aacgccctgggg-3' (SEQ ID NO:7; corresponding to nucleotides 641-780 of SEQ ID NO:1, but including the C→T substitution, shown in bold and underlined), or the complement thereof.

In one non-limiting exemplary embodiment, the target nucleic acid comprises Target Region 1b, where Target Region 1b is:

5'-gccttcccgg tgcccgacgt gttcccactg ccgccgccac caccgc-cgct cccgagcccg ggacaggcgt cccactgctc gtcgcctgcc acccgct-tcg gccacggcca-3' (SEQ ID NO:8; corresponding to nucleotides 601-710 of SEQ ID NO:1), or a complement thereof.

In one non-limiting exemplary embodiment, the target nucleic acid comprises Target Region 1c, where Target Region 1c is:

5'-tggggctcct cctcgccgtc gcccccgccc ccgccacccc cggtct-tcag ccccacggct gccttcccgg tgcccgacgt gttcccactg ccgccgccac caccgccgct cccgagcccg-3' (SEQ ID NO:9; corresponding to nucleotides 541-660 of SEQ ID NO:1), or the complement thereof.

In one non-limiting exemplary embodiment, the target nucleic acid comprises Target Region 1d, where Target Region 1d is:

5'-ggacaggcgt cccactgctc gtcgcctgcc acccgcttcg gccacg-gcca gacgtccgcg gccttcctca gcgctctgct gccctcgcag ccgccgc-cgg cggccgtcaa cgccctgggg-3' (SEQ ID NO:10; corresponding to nucleotides 621-780 of SEQ ID NO:1, but including the C→T substitution), or the complement thereof.

In another non-limiting exemplary embodiment, the target nucleic acid comprises Target Region 2, where Target Region 2 is:

5'-ggaccctctgaagctccagcaactcca-gaaccaaatccgactggagcaggaggccggcgctcgg cagcctccgccagc-cccgcgcagcgcgccgccctcgcccccttcccgccgccgcccgccttcc ccgagctcgcggcctgcacgccgc-ccgcgtcccggagcccatgagcgcgctggcctcccgctc cgccccgccatg-cagtcctccggctccttcaactacgcgcgccccaagcagttcatcgccgcg cagaacctcgggcccgcgtcgggccacg- gcacgccggcctccagccccagctcgtccagcctcc cgtcgcccatgtc- cccgacgccgaggcagttcggccgcgcccccgtgccgcccttcgcgcagcc cttcggcgctgagcccgaggc- cccgtggggctcctcctcgccgtcgcccccgcccccgccaccc ccggtct- tcagccccacggctgccttcccggtgc- ccgacgtgttcccactgccgccgccaccac cgccgctcccgagcccgggacaggcgtc- ccactgctcgtcgcctgccacccgcttcggccacgg ccagacg Cccgcggccttcctcagcgctctgctgccctcgcagccgccgccggcggcc- gtcaac gccctggggctgcccaagggtgtcacccccgc-3' (SEQ ID NO:11; corresponding to nucleotides 132-803 of SEQ ID NO:1), or the complement thereof.

1671 G→T Nucleotide Substitution

Target palladin nucleic acids include palladin nucleic acids that include the 1671 G→T substitution; palladin nucleic acids that are abnormally expressed in cancerous and precancerous cells (e.g., cancerous and precancerous pancreatic cells); and palladin nucleic acids that are abnormally expressed in non-cancerous cells that are indicative of the presence of a cancerous cell. A target palladin nucleic acid that is abnormally expressed in a cancerous or a precancerous cell (e.g., a cancerous or a precancerous pancreatic cell) or an indicator cell may or may not include the 1671 G→T substitution. In some embodiments, a target palladin nucleic acid that is overexpressed in a cancerous or precancerous cell (e.g., a cancerous or a precancerous pancreatic cell) is a palladin mRNA that encodes the 90 kD isoform of palladin. In some embodiments, a target palladin nucleic acid that is overexpressed in a cancerous or a precancerous cell (e.g., a cancerous or a precancerous pancreatic cell) includes nucleotide sequences found in exon 9 of the palladin gene, e.g., all or part of the sequence depicted in nucleotides 1639 through 1846 of the sequence shown in FIG. 1A.

In some embodiments, a nucleic acid probe hybridizes to and provides for detection of a palladin nucleic acid comprising a nucleotide substitution that is associated with cancer (e.g., pancreatic cancer). In some embodiments, a nucleotide substitution associated with cancer is a G-to-T (G→T) substitution at a location corresponding to nucleotide 1671 of SEQ ID NO:1, and as depicted in FIG. 1A. As depicted in FIG. 1A, the underlined and bolded "G" at position 1671 is the wild-type sequence; substitution of the G at position 1671 with a T is associated with pancreatic cancer. In some embodiments, the target nucleic acid is a palladin mRNA, e.g., a G→T substitution at a position corresponding to nucleotide 1671 of SEQ ID NO:1 (GenBank AB023209) is detected in a palladin mRNA. In other embodiments, the target nucleic acid is a cDNA, e.g., a G→T substitution at a position corresponding to nucleotide 1671 of SEQ ID NO:1 (GenBank AB023209) is detected in a cDNA copy of a palladin mRNA. In other embodiments, the target nucleic acid is genomic DNA, e.g., a G→T substitution at a position corresponding to nucleotide 1671 of SEQ ID NO:1 is detected in palladin genomic DNA, e.g., exon 9 of the palladin gene. For example, a genomic DNA comprising exon 9 sequences and including nucleotide 183561 of the sequence set forth in GenBank Accession No. AC080188 (where nucleotide 183561 corresponds to nucleotide 1671 of SEQ ID NO:1) is depicted in FIG. 14.

In some embodiments, the target nucleic acid comprises a nucleotide sequence that has at least about 70%, at least about 75%, at least about 80%, at least about 85%, at least about 90%, at least about 95%, or at least about 98% nucleotide sequence identity with a stretch of at least about 25, at least about 50, at least about 100, at least about 150, or at least about 200 contiguous nucleotides of nucleotide 1639 to nucleotide 1846 of SEQ ID NO:1 (or a complement thereof), which is an exon that includes the G→T substitution at position 1671.

In some embodiments, the target nucleic acid comprises a nucleotide sequence of from about nucleotide 1639 to about nucleotide 1846 of SEQ ID NO:1 (or a complement thereof). In some embodiments, the target nucleic acid comprises from about nucleotide 1639 to about nucleotide 1846, from about nucleotide 1639 to about nucleotide 1840, from about nucleotide 1639 to about nucleotide 1800, from about nucleotide 1639 to about nucleotide 1750, from about nucleotide 1639 to about nucleotide 1700, from about nucleotide 1645 to about nucleotide 1846, from about nucleotide 1650 to about nucleotide 1846, or from about nucleotide 1660 to about nucleotide 1846 of SEQ ID NO:1, or the complement of any of the foregoing. In some embodiments, the target nucleic acid will comprise a G at a position corresponding to nucleotide 1671 of SEQ ID NO:1; in other embodiments, the target nucleic acid will comprise a T at a position corresponding to nucleotide 1671 of SEQ ID NO:1.

In some embodiments, a suitable target nucleic acid comprises at least the sequence 5'-atctaagctggcaactagat-3' (SEQ ID NO:12), or a complement thereof, or at least the sequence 5'-atctaagctgtcaactagat-3' (SEQ ID NO:13), or a complement thereof, where the bold and underlined nucleotides represent alternative residues at a position corresponding to 1671 of SEQ ID NO:1. In some embodiments, a suitable target nucleic acid comprises at least the sequence 5'-ccaacccca-gatctaagctggcaactagatggaaagcccg-3' (SEQ ID NO:14), or the complement thereof, or at least the sequence 5'-ccaacccca-gatctaagctgtcaactagatggaaagcccg-3' (SEQ ID NO:15), where the bold and underlined nucleotides represent alternative residues at a position corresponding to 1671 of SEQ ID NO:1.

In one non-limiting exemplary embodiment, the target nucleic acid comprises Target Region 3, where Target Region 3 is:
5'-gtcagtgggttaccaacccca- gatctaagctggcaactagatggaaagc- ccgtacgccctgacagtgctcacaagatgctggtgcgtgag aacggggtg- cactctctgatcatagagccagtcacgtcacgtgatgccggcatctacacatgtat- agctaccaaccgagcaggacagaact cattcagcctggagcttgtggttgc- tg (SEQ ID NO:16; corresponding to nucleotides 1639-1846 of SEQ ID NO:1), or the complement thereof.

In one non-limiting exemplary embodiment, the target nucleic acid comprises Target Region 3a, where Target Region 3a is:
5'-gtcagtgggttaccaacccagatctaagctg tcaactagatggaaagcccgtacgccctgacagtgctcacaagatgctggt- gcgtgaga acggggtgcactctctgatcatagagc- cagtcacgtcacgtgatgccggcatcta- cacatgtatagctaccaaccgagcaggacagaactc attcagcctggagcttgt- gttgctg (SEQ ID NO:17; corresponding to nucleotides 1639-1846 of SEQ ID NO:1, but including the G→T substitution, shown in bold and underlined), or the complement thereof.

In one non-limiting exemplary embodiment, the target nucleic acid comprises Target Region 3b, where Target Region 3b is:
5'-gtcagtgggttaccaacccca- gatctaagctggcaactagatggaaagc- ccgtacgccctgacagtgctcacaagatgctggtgcgtgag aacggggtg- cactctctgatcatagagccagt (SEQ ID NO:18; corresponding to nucleotides 1639-1760 of SEQ ID NO:1), or the complement thereof.

In one non-limiting exemplary embodiment, the target nucleic acid comprises Target Region 3c, where Target Region 3c is:

5'-gtcagtgggttaccaacccagatctaagag
tcaactagatggaaagcccgtacgccctgacagtgctcacaagatgctggtgc-
gtgaga acggggtgcactctctgatcatagagccagt (SEQ ID NO:19;
corresponding to nucleotides 1639-1760 of SEQ ID NO:1,
but including the G→T substitution, shown in bold and
underlined), or the complement thereof.

2060 C→T Nucleotide Substitution

Target palladin nucleic acids include palladin nucleic acids that include the 2060 C→T substitution; and palladin nucleic acids that are overexpressed in cancerous and precancerous cells (e.g., cancerous and precancerous pancreatic cells). A target palladin nucleic acid that is overexpressed in a cancerous or a precancerous cell (e.g., a cancerous or a precancerous pancreatic cell) may or may not include the 2060 C→T substitution. In some embodiments, a target palladin nucleic acid that is overexpressed in a cancerous or precancerous cell (e.g., a cancerous or a precancerous pancreatic cell) is a palladin mRNA that encodes the 140 kD isoform of palladin. In some embodiments, a target palladin nucleic acid that is overexpressed in a cancerous or a precancerous cell (e.g., a cancerous or a precancerous pancreatic cell) includes nucleotide sequences found in exon 10 of the palladin gene, e.g., all or part of the sequence depicted in nucleotides 1833-2175 of the sequence shown in FIGS. 13A and 13B (se, e.g., GenBank Accession No. NM 016081).

In some embodiments, a nucleic acid probe hybridizes to and provides for detection of a palladin nucleic acid comprising a nucleotide substitution that is associated with cancer, e.g., pancreatic cancer. In some embodiments, a nucleotide substitution associated with cancer is a C-to-T (G→T) substitution at a location corresponding to nucleotide 2060 of SEQ ID NO:20 (GenBank NM_016081, and as depicted in FIGS. 13A and 13B. As depicted in FIGS. 13A and 13B, the underlined and bolded "C" at position 2060 is the wild-type sequence; substitution of the C at position 2060 with a T is associated with cancer. In some embodiments, the target nucleic acid is a palladin mRNA, e.g., a C→T substitution at a position corresponding to nucleotide 2060 of SEQ ID NO:20 (GenBank NM_016081; FIGS. 13A and 13B) is detected in a palladin mRNA. In other embodiments, the target nucleic acid is a cDNA, e.g., a C→T substitution at a position corresponding to nucleotide 2060 of SEQ ID NO:1 (GenBank NM_016081) is detected in a cDNA copy of a palladin mRNA. In other embodiments, the target nucleic acid is genomic DNA, e.g., a C→T substitution at a position corresponding to nucleotide 2060 of SEQ ID NO:20 (GenBank NM_016081) is detected in palladin genomic DNA, e.g., exon 10 of the palladin gene. For example, a genomic DNA comprising nucleotide 27251 of the sequence set forth in GenBank Accession No. AC084353 (corresponding to nucleotide 2060 of the sequence depicted in FIGS. 13A and 13B) is depicted in FIG. 15.

In some embodiments, the target nucleic acid comprises a nucleotide sequence that has at least about 70%, at least about 75%, at least about 80%, at least about 85%, at least about 90%, at least about 95%, or at least about 98% nucleotide sequence identity with a stretch of at least about 25, at least about 50, at least about 100, at least about 150, at least about 200, at least about 250, at least about 300, or at least about 340 contiguous nucleotides of nucleotide 1833 to nucleotide 2175 of SEQ ID NO:20 (GenBank NM_016081; or a complement thereof), which is an exon that includes the C→T substitution at position 2060.

In some embodiments, the target nucleic acid comprises a nucleotide sequence of from about nucleotide 1833 to about nucleotide 2175 of SEQ ID NO:20 (GenBank NM_016081), or a complement thereof. In some embodiments, the target nucleic acid comprises from about nucleotide 1833 to about nucleotide 2080, from about nucleotide 1833 to about nucleotide 2090, from about nucleotide 1833 to about nucleotide 2100, from about nucleotide 1833 to about nucleotide 2150, from about nucleotide 1833 to about nucleotide 2160, from about nucleotide 1850 to about nucleotide 2175, from about nucleotide 1900 to about nucleotide 2175, from about nucleotide 1950 to about nucleotide 2175, or from about nucleotide 2000 to about nucleotide 2175 of SEQ ID NO:20 (GenBank NM_016081), or the complement of any of the foregoing. In some embodiments, the target nucleic acid will comprise a C at a position corresponding to nucleotide 2060 of SEQ ID NO:20 (GenBank NM_016081); in other embodiments, the target nucleic acid will comprise a T at a position corresponding to nucleotide 2060 of SEQ ID NO:20 (GenBank NM_016081).

In some embodiments, a suitable target nucleic acid comprises at least the sequence 5'-cccagccgtggagtaaat-3' (SEQ ID NO:21; GenBank NM_016081), or a complement thereof, or at least the sequence 5'-cccagctgtggagtaaat-3' (SEQ ID NO:22; corresponding to nucleotides 2054-2071 of SEQ ID NO:20, GenBank NM_016081), or a complement thereof, where the bold and underlined nucleotides represent alternative residues at a position corresponding to 2060 of SEQ ID NO:20 (GenBank NM_016081). In some embodiments, a suitable target nucleic acid comprises at least the sequence 5'-ggagtccatcccagccgtggagtaaatggactgattaacgg-3' (SEQ ID NO:23; nucleotides 2045-2085 of SEQ ID NO:20, GenBank NM_016081, FIGS. 13A and 13B), or the complement thereof, or at least the sequence 5'-ggagtccatcccagc tgtggagtaaatggactgattaacgg-3' (SEQ ID NO:24; GenBank NM_016081), where the bold and underlined nucleotides represent alternative residues at a position corresponding to 2060 of SEQ ID NO:20 (GenBank NM_016081).

In one non-limiting exemplary embodiment, the target nucleic acid comprises Target Region 4, where Target Region 4 is:
5'-ccaacactgaaaactgtagttacgagt-
caatgggagaatccaacaatgaccact-
tccaacactttccacctcccctccaatcttggagacaa gttccttggagttggct-
tcaaagaaaccatctgagatccagcaggtgaacaaccctgagttaggcctgagc-
agggcagccttcaaatgca attcaatgctgctgagagggaaac-
gaacggagtccatcccagc
cgtggagtaaatggactgattaacggcaaagctaacagtaataaatct cttccaa-
caccagctgtcctgctttcacccac-
taaggagccaccacctctgcttgccaaaccaaaact (SEQ ID NO:25; corresponding to nucleotides 1833-2175 of SEQ ID NO:25 (GenBank NM_016081)), or the complement thereof.

In one non-limiting exemplary embodiment, the target nucleic acid comprises Target Region 4a, where Target Region 4a is:
5'-ccaacactgaaaactgtagttacgagt-
caatgggagaatccaacaatgaccact-
tccaacactttccacctcccctccaatcttggagacaa gttccttggagttggct-
tcaaagaaaccatctgagatccagcaggtgaacaaccctgagttaggcctga-
gcagggcagccttcaaatgca attcaatgctgctgagagggaaac-
gaacggagtccatcccagc
tgtggagtaaatggactgattaacggcaaagctaacagtaataaatct cttccaa-
caccagctgtcctgctttcacccac-
taaggagccaccacctctgcttgccaaaccaaaact (SEQ ID NO:26; corresponding to nucleotides 1833-2175 of SEQ ID NO:20 (GenBank NM_016081), but including the C→T substitution at a position corresponding to nucleotide 2060 of NM_016801), or the complement thereof.

In one non-limiting exemplary embodiment, the target nucleic acid comprises Target Region 4b, where Target Region 4b is:

5'-ttcaatgctgctgagagggaaacgaacg-
gagtccatcccagccgtggagtaaatg-
gactgattaacggcaaagctaacagtaataaatctc tt (SEQ ID NO:27; corresponding to nucleotides 2018 to 2110 of SEQ ID NO:20 (GenBank NM_016081), or the complement thereof.

In one non-limiting exemplary embodiment, the target nucleic acid comprises Target Region 4c, where Target Region 4c is:

5'-ttcaatgctgctgagagggaaacgaacggagtccatcccagc tgtggagtaaatggactgattaacggcaaagctaacagtaataaatctct t (SEQ ID NO:28; corresponding to nucleotides 2018 to 2110 of SEQ ID NO:20 (GenBank NM_016081) but including the C→T substitution at a position corresponding to nucleotide 2060 of NM_016801), or the complement thereof.

Insertions in a Palladin Promoter

Target palladin nucleic acids include palladin nucleic acids that include a palladin gene promoter that includes a nucleotide sequence insertion, e.g., an insertion of one or more nucleotides not present in a palladin gene promoter present in a normal (non-cancerous) cell. Thus, the insertion in the palladin gene promoter is associated with an increased risk of developing cancer (e.g., pancreatic cancer), and/or the presence of a pre-cancerous or cancerous cell (e.g., a pre-cancerous or cancerous pancreatic cell).

In some embodiments, a nucleic acid probe hybridizes to a region of a palladin gene promoter that includes a nucleotide sequence insertion, e.g., an insertion of 1 nt to 5 nt, from 5 nt to 10 nt, from 10 nt to 15 nt, from 15 nt to 20 nt, from 20 nt to 25 nt, from 25 nt to 30 nt, from 30 nt to 35 nt, from 35 nt to 40 nt, from 40 nt to 50 nt, or more than 50 nt.

A target nucleic acid can include a palladin gene promoter of any isoform of palladin. For example, in some embodiments, the target nucleic acid is a promoter region of the palladin gene that encodes the 90 kDa isoform of palladin. FIG. 19 depicts a nucleotide sequence (SEQ ID NO:110) that includes a promoter for the gene encoding the 90 kDa isoform of palladin, where the promoter region is boxed (e.g., nucleotides 501-1987 of SEQ ID NO:110. The promoter region includes a 12-base pair insertion after nucleotide 704 of SEQ ID NO:110. The 12-bp insertion is associated with an increased risk of developing cancer and/or the presence of a pre-cancerous or cancerous cell. A promoter without the 12-base pair insertion would include nucleotides 501-704 and 717-1987 of SEQ ID NO:110. The 12-base pair insertion is nucleotides 705-716 of SEQ ID NO:110. An example of a promoter region of a palladin gene encoding the 90 kDa isoform of palladin, without the 12-base pair insertion, is SEQ ID NO:111, which includes nucleotides 501-704 and 717-1987 of SEQ ID NO:110.

In some embodiments, a target nucleic acid comprises a nucleotide sequence that has at least about 70%, at least about 75%, at least about 80%, at least about 85%, at least about 90%, at least about 95%, or at least about 98% nucleotide sequence identity with a stretch of at least about 25, at least about 50, at least about 100, at least about 150, at least about 200, at least about 250, at least about 500, at least about 750, at least about 1000, at least about 1250, or at least 1475 contiguous nucleotides of the nucleotide sequence set forth in SEQ ID NO:111. SEQ ID NO:111 provides a nucleotide sequence of a palladin promoter without nucleotide sequence insertions.

In some embodiments, a target nucleic acid comprises a nucleotide sequence that has at least about 70%, at least about 75%, at least about 80%, at least about 85%, at least about 90%, at least about 95%, or at least about 98% nucleotide sequence identity with a stretch of at least about 25, at least about 50, at least about 100, at least about 150, at least about 200, at least about 250, at least about 500, at least about 750, at least about 1000, at least about 1250, or at least 1487 contiguous nucleotides of the nucleotide sequence set forth in nucleotides 501-1987 of SEQ ID NO:110 (see FIG. 19). In some embodiments, a target nucleic acid includes a nucleotide sequence insertion, compared to the sequence set forth in SEQ ID NO:111. For example, in some embodiments, the target nucleic acid includes a nucleotide sequence insertion at a position corresponding to nucleotide 704 of the sequence set forth in SEQ ID NO:111.

In one non-limiting exemplary embodiment, a target nucleic acid comprises the nucleotide sequence of Target Region 5, where Target Region 5 is the nucleotide sequence set forth in SEQ ID NO:111.

In another non-limiting exemplary embodiment, a target nucleic acid comprises the nucleotide sequence of Target Region 5a, where Target Region 5a has the sequence:

5'-CGGGCGAGGTATAAAGCCCGATACCTGC-
CCCGCGCCCGGTCCGCGGAGCCCGCTG CAGCTC-
CCGCTCGCTCCGGACGCG-
GAATCGGGCAGCAGCGGGAGGCGGCCCGGAG
AGCCGAGG-3' (SEQ ID NO:112), where the sequence corresponds to nucleotides 658-775 of the nucleotide sequence depicted in FIG. 19 and set forth in SEQ ID NO:110, and where the 12-base pair insertion is in bold; or the complement of the sequence.

Sources of Target Nucleic Acids

Where the detection methods involve detection of a palladin-encoding nucleic acid, the target nucleic acids are detected in samples obtained from a tissue comprising cells. In some embodiments, the cells are obtained from a tissue suspected of comprising cancer cells. For example, in some embodiments, the cells are obtained from pancreatic tissue. As another example, the cells are obtained from breast tissue and/or axillary lymph nodes. As yet another example, the cells are obtained from the upper aerodigestive tract (including cells, e.g., squamous cells, obtained from the lips, mouth, tongue, nose, throat, larynx, pharynx, and upper trachea; but not including cells obtained from the stomach or intestines), and tissues such as cervical lymph nodes. In other embodiments, the cells are indicator cells, e.g., the cells themselves are not suspected of comprising cancer cells, but serve as an indication of the presence of cancer cells in an individual. Such indicator cells include, e.g., white blood cells. For example, peripheral blood mononuclear cells are suitable indicator cells.

For example, target nucleic acids can be detected in samples obtained from pancreatic cells, particularly human pancreatic cells. Pancreatic cells suitable for analysis include, but are not limited to, ductal pancreatic epithelial cells; pancreatic acinar cells; pancreatic stroma and/or extra-cellular matrix; pancreatic stem cells; and pancreatic islet cells. In addition, other targets for palladin detection can include, but are not limited to, biologic sources of tissue including peripheral white blood cells and pancreatic juice.

Head and neck cancers are malignant growths originating in the lip and oral cavity, nasal cavity, pharynx, larynx, thyroid, paranasal sinuses, salivary glands and cervical lymph nodes of the neck. Squamous cell carcinomas represent more than 90% of all head and neck cancers, and originate from the squamous cells that line the upper aerodigestive tract. Suitable sources of target nucleic acids in the context of head and neck squamous cell carcinoma include tissues obtained from any of: the lip, the oral cavity (mouth), nasal cavity, pharynx, larynx, thyroid, paranasal sinuses, salivary glands, and cervical lymph nodes of the neck. Suitable sources of target nucleic acids include a tissue sample from any of the aforementioned sources, where the tissue sample includes squamous cells. Suitable sources of target nucleic acids include cells obtained by oral rinse; oral swab; and tissue biopsy from any of the aforementioned sites.

In the context of breast cancer, suitable sources of target nucleic acids include breast cells and lymph node cells, e.g., cells obtained via fine needle aspiration biopsy; cells obtained via core needle biopsy; cells obtained from lymph nodes in the vicinity of the breast (e.g., axillary lymph nodes); and the like.

In the context of breast cancer, breast cancers that can be detected using a subject method include mammary carcinoma, adenocarcinoma, ductal carcinoma in situ, lobular (small cell) carcinoma, intraductal carcinoma, medullary breast cancer, mucinous breast cancer, tubular breast cancer, papillary breast cancer, Paget's disease, inflammatory breast cancer, and hormone dependent tumors of the breast.

Nucleic Acid Probes

As discussed above, the present invention provides detection, diagnostic, and staging methods, e.g., methods for detecting and diagnosing cancer (e.g., pancreatic cancer, breast cancer, head and neck squamous cell cancer, etc.) in an individual; methods of identifying individuals at risk of developing cancer (e.g., pancreatic cancer); and methods of staging cancer (e.g., pancreatic cancer, breast cancer, head and neck squamous cell cancer, etc.). The methods generally involve detecting a nucleotide sequence alteration (e.g., nucleotide substitution, a nucleotide sequence insertion, a nucleotide sequence deletion, a change in methylation status, etc.), a level of palladin mRNA, or both. In aspects where detection of the presence of palladin gene having a cancer-associated nucleotide substitution is desired, a subject method provides for detection one of more of the following exemplary nucleotide substitutions: 1) a C→T nucleotide substitution at a position corresponding to nucleotide 715 ("a 715 C→T substitution") of a human palladin nucleic acid, e.g., nucleotide 715 of a palladin nucleic acid as set forth in GenBank Accession No. AB023209 and depicted in FIG. 1A, where nucleotide 715 is underlined and in bold text; 2) a G→T nucleotide substitution at a position corresponding to nucleotide 1671 ("a 1671 G→T substitution") of a human palladin nucleic acid, e.g., nucleotide 1671 of a palladin nucleic acid as set forth in GenBank Accession No. AB023209 and depicted in FIG. 1A, where nucleotide 1671 is underlined and in bold text; 3) a C→T substitution at a position corresponding to nucleotide 2060 ("a 2060 C→T substitution") of a human palladin nucleic acid, e.g., a nucleotide 2060 of a palladin nucleic acid as set forth in GenBank Accession No. NM_016081 and depicted in FIGS. 13A and 13B, where nucleotide 2060 is underlined and in bold text. In aspects where detection of the presence of palladin gene promoter having a cancer-associated nucleotide sequence insertion is desired, a subject method provides for detection of, e.g., a nucleotide insertion in a promoter of a palladin gene encoding palladin, e.g., encoding the 90 kDa isoform of palladin. In other aspects, a subject method provides for detection of a level of a palladin mRNA in a cell. Both of these methods (detecting a nucleotide sequence alteration; and detecting a palladin mRNA level) can be carried out using a method involving nucleic acid hybridization, amplification, or both.

Nucleic acid hybridization can be carried out using a nucleic acid probe that detects: a) a cancer-associated nucleotide sequence alteration in a palladin target nucleic acid; b) a level of a palladin mRNA that is abnormally expressed in a cancerous or precancerous cell; or c) both a cancer-associated nucleotide sequence alteration in a palladin target nucleic acid and a level of a palladin mRNA that is abnormally expressed in a cancerous or precancerous cell.

For example, nucleic acid hybridization can be carried out using a nucleic acid probe that detects: a) a pancreatic cancer-associated nucleotide sequence alteration in a palladin target nucleic acid; b) a level of a palladin mRNA that is abnormally expressed in a cancerous or precancerous pancreatic cell; or c) both a pancreatic cancer-associated nucleotide sequence alteration in a palladin target nucleic acid and a level of a palladin mRNA that is abnormally expressed in a cancerous or precancerous pancreatic cell.

For example, nucleic acid hybridization can be carried out using a nucleic acid probe that detects: a) a cancer-associated nucleotide substitution (e.g., a defined by a 715 C→T substitution, a 1671 G→T substitution, or a 2060 C→T substitution in a palladin target nucleic acid); b) a level of a palladin mRNA that is overexpressed in a cancerous or precancerous cell; or c) both a 715 C→T substitution a 1671 G→T substitution, or a 2060 C→T substitution in a palladin target nucleic acid and a level of a palladin mRNA that is overexpressed in a cancerous or precancerous cell. In addition, nucleic acid hybridization can be used to detect a nucleotide sequence insertion in a palladin promoter. The following is a description of exemplary probes that can be used in a subject method.

Where the method involves detection of a cancer-associated nucleotide sequence alteration (e.g., a nucleotide substitution, a nucleotide sequence insertion, a nucleotide sequence deletion, a change in methylation status, etc.) in palladin, suitable nucleic acid probes include nucleic acid probes that hybridize to and provide for detection of a palladin nucleic acid comprising a nucleotide substitution that is associated with cancer, e.g., a palladin 715 C→T substitution, a 1671 G→T substitution, or a 2060 C→T substitution; and nucleic acid probes that hybridize to and provide for detection of a palladin nucleic acid comprising a nucleotide sequence insertion that is associated with cancer. Where abnormal expression of palladin is to be detected, nucleic acid probes suitable for use include nucleic acid probes that hybridize to and provide for detection of a palladin nucleic acid that is overexpressed or underexpressed in an indicator cell, a cancerous cell, or a precancerous cell. The present invention provides such nucleic acid probes.

Suitable nucleic acid probes are in some embodiments in the range of between 10-50 nucleotides long, such as 10 to 50, 12 to 45, 15 to 40, 20 to 35, 25 to 30 nucleotides, and the like. For example, probes will in some embodiments be in the range of between 18 to 40, 19 to 35, 20 to 30, 21 to 29, 22 to 28, 23 to 27, 24-25 nucleotides long, and any length between the stated ranges. Probes of about 20 to 22 nucleotides in length are of particular interest in some embodiments.

A suitable probe may be coupled to a label for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Exemplary fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Current technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. In some embodiments, the probe is attached to the solid support by a linker which serves to distance the probe from the solid support. The linker is in many embodiments at least 15-30 atoms in length, or at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. In some embodiments, polymers such as functionalized polyethylene glycol are used because they do not significantly interfere with the hybridization of probe to the target oligonucleotide. In some embodiments, the linked is polyethylene glycol.

The linkages between the solid support, the linker and the probe are normally not cleaved during removal of base protecting groups under basic conditions at high temperature. Examples of suitable linkages include carbamate and amide linkages.

Examples of suitable types of solid supports for immobilization of the oligonucleotide probe include controlled pore glass, glass plates, polystyrene, avidin-coated polystyrene beads, cellulose, nylon, acrylamide gel and activated dextran.

Probes for use in detection of a pancreatic cancer-associated nucleotide substitution in a palladin gene, and probes useful in assessing palladin expression levels are described in more detail below.

Probes for Detecting a Cancer-Associated Nucleotide Substitutions in Palladin

In some embodiments, a suitable nucleic acid probe hybridizes to and provides for detection of a palladin nucleic acid (e.g., genomic DNA; mRNA; cDNA; amplified copies of any of the foregoing; etc.) comprising a nucleotide substitution associated with cancer (e.g., pancreatic cancer, breast cancer, head and neck squamous cell cancer, etc.).

Probes for Detecting a 715 C→T Substitution

Non-limiting examples of nucleic acid probes that hybridize to a nucleic acid comprising Target Region 1, and that detect the presence of the C→T substitution depicted in Target Region 1 include:

Probe 1: 5'-CGGCCAGACGTCCGCGGCCTT-3' (SEQ ID NO:29), or the complement thereof, e.g., 5'-AAGGCCGCGGACGTCTGGCCG-3' (SEQ ID NO:30);

Probe 2: 5'-GCCACGGCCAGACGTCCGCGGCCTT-3' (SEQ ID NO:31), or the complement thereof, e.g., 5'-AAGGCCGCGGACGTCTGGCCGTGGC-3' (SEQ ID NO:32);

Probe 3: 5'-CGGCCAGACGTCCGCGGCCTTCCTC-3' (SEQ ID NO:33), or the complement thereof, e.g., 5'-GAGGAAGGCCGCGGACGTCTGGCCGTGGC-3' (SEQ ID NO:34); and Probe 4: 5'-GCCACGGCCAGACGTCCGCGGCCTTCCTC-3' (SEQ ID NO:35), or the complement thereof, e.g., 5'-GAGGAAGGCCGCGGACGTCTGGCCGTGGC-3' (SEQ ID NO:36).

Any of Probes 1-4, above, or any of the complements thereof, will in some embodiments include additional 5' and/or 3' sequences. The additional 5' and/or 3' sequences will in some embodiments provide for hybridization with the target region. In other embodiments, the additional 5' and/or 3' sequences will provide restriction endonuclease recognition sites, for cloning the probe into a vector.

Probes for Detecting a 1671 G→T Substitution

Non-limiting examples of nucleic acid probes that hybridize to a nucleic acid comprising Target Region 3, and that detect the presence of the G→T substitution depicted in Target Region 3 include:

Probe 5: 5'-ctaagctggcaactagatgg-3' (SEQ ID NO:37), or the complement thereof, e.g., 5'-ccatctagttgccagcttag-3' (SEQ ID NO:38);

Probe 6: 5'-gatctaagctggcaactagat-3' (SEQ ID NO:39), or the complement thereof, e.g., 5'-atctagttgccagcttagatc-3' (SEQ ID NO:40); and Probe 7: 5'-gatctaagctggcaactagatgg-3' (SEQ ID NO:41), or the complement thereof, e.g., 5'-ccatctagttgccagcttagatc-3' (SEQ ID NO:42).

Any of Probes 5-7, above, or any of the complements thereof, will in some embodiments include additional 5' and/or 3' sequences. The additional 5' and/or 3' sequences will in some embodiments provide for hybridization with the target region. In other embodiments, the additional 5' and/or 3' sequences will provide restriction endonuclease recognition sites, for cloning the probe into a vector.

Probes for Detecting a 2060 C→T Substitution

Non-limiting examples of nucleic acid probes that hybridize to a nucleic acid comprising Target Region 4, and that detect the presence of the C→T substitution depicted in Target Region 4 include:

Probe 8: 5'-ccatcccagccgtggagtaaatgg (SEQ ID NO:43), or the complement thereof, e.g., 5'-ccatttactccacggctgggatgg-3' (SEQ ID NO:44);

Probe 9: 5'-cccagccgtggagtaaatgg-3' (SEQ ID NO:45), or the complement thereof, e.g., 5'-ccatttactccacggctggg-3' (SEQ ID NO:46); and Probe 10: 5'-gtccatcccagccgtggagtaaatggactg-3' (SEQ ID NO:47), or the complement thereof, e.g., 5'-cagtccatttactccacggctgggatggac-3' (SEQ ID NO:48).

Any of Probes 8-10, above, or any of the complements thereof, will in some embodiments include additional 5' and/or 3' sequences. The additional 5' and/or 3' sequences will in some embodiments provide for hybridization with the target region. In other embodiments, the additional 5' and/or 3' sequences will provide restriction endonuclease recognition sites, for cloning the probe into a vector.

Probes for Detecting Abnormal Expression of a Palladin Nucleic Acid

In some embodiments, a suitable nucleic acid probe hybridizes to and provides for detection of a palladin nucleic acid that is abnormally expressed (e.g., over-expressed or underexpressed) in a cell (e.g., a cell from a tissue suspected of comprising a cancer cell; or an indicator cell such as a white blood cell). In these embodiments, suitable target nucleic acids include a palladin mRNA; a cDNA copy of all or a portion of (e.g., a subsequence of) a palladin mRNA; a nucleic acid amplification product generated by amplifying a cDNA copy of a palladin mRNA; and the like. In some embodiments, a target nucleic acid will include all or a part of an exon (e.g., exon 2, exon 9, exon 10) of the palladin gene, and may or may not include a nucleotide substitution that is associated with pancreatic cancer. In some of these embodiments, a nucleic acid probe will comprise a variable nucleotide that is associated with pancreatic cancer (e.g., will comprise one or more of: a) a nucleotide sequence that includes either a C or a T at a position corresponding to 715 of SEQ ID NO:1; b) a nucleotide sequence that includes either a G or a T at a position corresponding to 1671 of SEQ ID NO:1; and c) a nucleotide sequence that includes either a C or a T at a position corresponding to 2060 of the sequence set forth in FIGS. 13A and 13B and in NM_016801). In other embodiments, a nucleic acid probe will not include a nucleotide sequence that includes any of the aforementioned nucleotides (e.g., a) a nucleotide sequence that includes either a C or a T at a position corresponding to 715 of SEQ ID NO:1; b) a nucleotide sequence that includes either a G or a T at a position corresponding to 1671 of SEQ ID NO:1; and c) a nucleotide sequence that includes either a C or a T at a position corresponding to 2060 of the sequence set forth in FIGS. 13A and 13B and in NM_016801).

Exemplary, non-limiting examples of probes that are suitable for detecting a palladin nucleic acid that is abnormally expressed in a cell include any of Probes 1-10, or a complement thereof, as described above.

Further suitable probes for detecting a palladin nucleic acid that is abnormally expressed in a cell include, e.g.:

Probe 11: 5'-acccgcttcg gccacggcca-3' (SEQ ID NO:49; corresponding to nucleotides 691-710 of SEQ ID NO:1), or the complement thereof;

Probe 12: 5'-gtcgcctgcc acccgcttcg gccacggc-3' (SEQ ID NO:50; corresponding to nucleotides 681-708 of SEQ ID NO:1) or the complement thereof;

Probe 13: 5'-gccttcctca gcgctctgct-3' (SEQ ID NO:51; corresponding to nucleotides 721-740 of SEQ ID NO:1), or the complement thereof;

Probe 14: 5'-gccttcctca gcgctctgct gccctcgcag-3' (SEQ ID NO:52; corresponding to nucleotides 721-750 of SEQ ID NO:1), or the complement thereof;

Probe 15: 5'-gcgctctgct gccctcgcag ccgcc-3' (SEQ ID NO:53, corresponding to nucleotides 731-755 of SEQ ID NO:1), or the complement thereof;

Probe 16: 5'-gccctcgcag ccgccgccgg cggccgtcaa-3' (SEQ ID NO:54, corresponding to nucleotides 741-770 of SEQ ID NO:1), or the complement thereof;

Probe 17: 5'-cagtgggtta ccaaccccag-3' (SEQ ID NO:55, corresponding to nucleotides 1641-1660 of SEQ ID NO:1), or the complement thereof;

Probe 18: 5'-ccaaccccag atctaagctg-3' (SEQ ID NO:56, corresponding to nucleotides 1651-1670 of SEQ ID NO:1), or the complement thereof;

Probe 19: 5'-ggaaagcccg tacgccctga-3' (SEQ ID NO:57, corresponding to nucleotides 1681-1700 of SEQ ID NO:1), or the complement thereof;

Probe 20: 5'-cagtgctcac aagatgctgg-3' (SEQ ID NO:58, corresponding to nucleotides 1701-1720 of SEQ ID NO:1), or the complement thereof;

Probe 21: 5'-aatgctgctg agagggaaac (SEQ ID NO:59, corresponding to nucleotides 2021-2040 of the sequence set forth in FIGS. 13A and 13B (NM_016081), or the complement thereof;

Probe 22: 5'-agagggaaac gaacggagtc catcc-3' (SEQ ID NO:60, corresponding to nucleotides 2031-2055 of the sequence set forth in FIGS. 13A and 13B (NM_016081), or the complement thereof;

Probe 23: 5'-gtggagtaaa tggactgatt aacggcaaag-3' (SEQ ID NO:61, corresponding to nucleotides 2061-2090 of the sequence set forth in FIGS. 13A and 13B (NM_016081), or the complement thereof; and Probe 24: 5'-gtaaa tggactgatt aacggc-3' (SEQ ID NO:62, corresponding to nucleotides 2066-2086 of the sequence set forth in FIGS. 13A and 13B (NM_016081), or the complement thereof.

Any of Probes 11-16, above, or any of the complements thereof, is suitable for detecting a palladin nucleic acid comprising all or a portion of Target Region 1, as described above. Any of Probes 17-20, above, or any of the complements thereof, is suitable for detecting a palladin nucleic acid comprising all or a portion of Target Region 3, as described above. Any of Probes 21-24, above, or any of the complements thereof, is suitable for detecting a palladin nucleic acid comprising all or a portion of Target Region 4, as described above.

Any of Probes 11-24, above, or any of the complements thereof, will in some embodiments include additional 5' and/or 3' sequences. The additional 5' and/or 3' sequences will in some embodiments provide for hybridization with the target region. In other embodiments, the additional 5' and/or 3' sequences will provide restriction endonuclease recognition sites, for cloning the probe into a vector.

Probes for Detecting a Cancer-Associated Nucleotide Sequence Insertions in a Palladin Nucleic Acid In some embodiments, a suitable nucleic acid probe hybridizes to and provides for detection of a palladin nucleic acid (e.g., genomic DNA; mRNA; cDNA; amplified copies of any of the foregoing; etc.) comprising a nucleotide sequence insertion associated with cancer (e.g., pancreatic cancer, breast cancer, head and neck squamous cell cancer, etc.).

For example, in some embodiments, a suitable nucleic acid probe hybridizes to and provides for detection of a palladin nucleic acid (e.g., a genomic DNA) comprising a nucleotide sequence insertion in a palladin promoter. In a particular non-limiting embodiment, a suitable nucleic acid probe hybridizes to and provides for detection of a palladin nucleic acid (e.g., a genomic DNA) comprising a nucleotide sequence insertion in a promoter of a palladin gene encoding the 90 kDa isoform of palladin.

For example, in some embodiments, a suitable nucleic acid probe hybridizes to and provides for detection of a nucleotide sequence insertion in the nucleotide sequence set forth in SEQ ID NO:111. A 12-base pair insertion was found in a palladin gene promoter, and is shown in FIG. 19. In some embodiments, a suitable nucleic acid probe hybridizes to and provides for detection of this 12-base pair insertion.

Non-limiting examples of a suitable probe include the following:

```
Probe 25:
5'-GCGGAGCCCGCTGCAGCTCCCG-3', (SEQ ID NO: 113)
``` corresponding to nucleotides 700-721 of the nucleotide sequence depicted in FIG. 19 and set forth in SEQ ID NO:110.

```
Probe 26:
5'-CGGAGCCCGCTGCAGCTCCC-3'.   (SEQ ID NO: 114)
``` corresponding to nucleotides 701-720 of the nucleotide sequence depicted in FIG. 19 and set forth in SEQ ID NO:110.

Probes 25 and 26, above, or any of the complements thereof, are suitable for detecting a palladin nucleic acid comprising all or a portion of Target Region 5a, as described above.

Nucleic Acid Primers

As discussed above, a subject method (e.g., a method for detecting and diagnosing cancer in an individual; a method of identifying individuals at risk of developing cancer; a method of staging cancer) will in some embodiments involve amplification of a target palladin nucleic acid. For example, a subject method that involves detection of a 715 C→T substitution, a 1671 G→T, or a 2060 C→T substitution in a palladin nucleic acid, or detection of a nucleotide substitution in a palladin gene, will in some embodiments comprise amplifying a target palladin nucleic acid, using a nucleic acid primer pair, forming a nucleic acid amplification product; and detecting the 715 C→T substitution, the 1671 G→T, or the 2060 C→T substitution, or an insertion in a palladin gene promoter, in the amplification product. In other aspects, a subject method provides for detection of a level of a palladin mRNA in a cell. In some embodiments, methods of detecting a level of a palladin mRNA in a cell will involve amplifying a target palladin nucleic acid, using a pair of nucleic acid primers.

As noted above, the present invention provides methods that involve detecting a palladin nucleic acid (e.g., a palladin mRNA) that is over-expressed in an indicator cell which is a cancerous or pre-cancerous cell. A palladin nucleic acid that is over-expressed in a cancerous tissue is a palladin nucleic acid (e.g., a palladin mRNA) that is present in a cancerous cell at a level that is at least about 25%, at least about 50%, at least about 2-fold, at least about 2.5-fold, at least about 5-fold, at least about 7.5-fold, at least about 10-fold, at least about 15-fold, at least about 20-fold, at least about 25-fold, at least about 30-fold, at least about 35-fold, at least about 40-fold, at least about 50-fold, or more, higher than the level of palladin nucleic acid (e.g., palladin mRNA) present in a control cell, e.g., a non-cancerous cell of the same cell type.

For example, the present invention provides methods that involve detecting a palladin nucleic acid (e.g., a palladin mRNA) that is over-expressed in a cancerous or pre-cancerous pancreatic cell. A palladin nucleic acid that is over-expressed in a cancerous pancreatic tissue is a palladin nucleic acid (e.g., a palladin mRNA) that is present in a cancerous pancreatic cell at a level that is at least about 25%, at least about 50%, at least about 2-fold, at least about 2.5-fold, at least about 5-fold, at least about 7.5-fold, at least about 10-fold, at least about 15-fold, at least about 20-fold, at least about 25-fold, at least about 30-fold, at least about 35-fold, at least about 40-fold, at least about 50-fold, or more, higher than the level of palladin nucleic acid (e.g., palladin mRNA) present in a control cell, e.g., a non-cancerous pancreatic cell of the same cell type.

A palladin nucleic acid that is over-expressed in a pre-cancerous pancreatic tissue is a palladin nucleic acid (e.g., a palladin mRNA) that is present in a pre-cancerous pancreatic cell at a level that is at least about 25%, at least about 50%, at least about 2-fold, at least about 2.5-fold, at least about 5-fold, at least about 7.5-fold, at least about 10-fold, at least about 15-fold, at least about 20-fold, at least about 25-fold, at least about 30-fold, at least about 35-fold, at least about 40-fold, at least about 50-fold, or more, higher than the level of palladin nucleic acid (e.g., palladin mRNA) present in a control cell, e.g., a non-cancerous pancreatic cell of the same cell type.

As noted above, in some embodiments, the methods provide for detection of a cancer in an individual, where a palladin target nucleic acid is detected in an indicator cell in a biological sample obtained from the individual, and where a level of palladin target nucleic acid that is lower than normal indicates the presence of cancer in the individual. A palladin target nucleic acid that is expressed at lower than normal levels is expressed at a level that is less than about 80%, less than about 70%, less than about 60%, less than about 50%, less than about 40%, less than about 30%, less than about 20%, or less than about 10% of the level present in an indicator cell from an individual not having cancer.

In general, primers provide for amplification of a palladin target nucleic acid to produce a palladin target nucleic acid amplification product (also referred to as an "amplicon"). Primers will in some embodiments be used in conjunction with a nucleic acid probe. 5' primers generally bind to a region to provide for amplification of the target nucleic, and in many embodiments bind to a 5' portion of the target sequence, as shown in FIGS. 10 and 14-16. 3' primers generally bind to a sequence that is complementary to a 3' portion of the nucleic acid generated by extension from the 5' primer, as exemplified in FIGS. 10 and 14-16.

Target nucleotide sequences to which 5' and 3' primers hybridize will be separated from one another by from about 10 nucleotides to about 650 nucleotides, e.g., from about 10 nucleotides to about 20 nucleotides, from about 20 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 100 nucleotides, from about 100 nucleotides to about 150 nucleotides, from about 150 nucleotides to about 200 nucleotides, from about 200 nucleotides to about 250 nucleotides, from about 250 nucleotides to about 300 nucleotides, from about 300 nucleotides to about 400 nucleotides, from about 400 nucleotides to about 500 nucleotides, or from about 500 nucleotides to about 650 nucleotides.

The amplification product that is generated will have a length of from about 30 nucleotides to about 670 nucleotides, e.g., from about 30 nucleotides to about 50 nucleotides, from about 50 nucleotides to about 100 nucleotides, from about 100 nucleotides to about 150 nucleotides, from about 150 nucleotides to about 200 nucleotides, from about 200 nucleotides to about 250 nucleotides, from about 250 nucleotides to about 300 nucleotides, from about 300 nucleotides to about 400 nucleotides, from about 400 nucleotides to about 500 nucleotides, or from about 500 nucleotides to about 670 nucleotides.

In certain embodiments, primers are designed so as to have a sequence complementary to one or more variant nucleotides within a target region sequence and/or to have a 3' end adjacent a variant nucleotide of a sequence of a target region. In some embodiments involving amplification-based detection, probes are designed so as to have a sequence complementary to a sequence flanked by the sequence(s) complementary to one or more primers used for amplification.

The amplification product will in many embodiments have a length in a range of from about 30 nucleotides (or base pairs, bp) to about 1000 nucleotides (or base pairs), e.g., from about 30 bp to about 50 bp, from about 50 bp to about 60 bp, from about 60 bp to about 70 bp, from about 70 bp to about 80 bp, from about 80 bp to about 90 bp, from about 90 bp to about 100 bp, from about 100 bp to about 150 bp, from about 150 bp to about 200 bp, from about 200 bp to about 250 bp, from about 250 bp to about 300 bp, from about 300 bp to about 350 bp, from about 350 bp to about 400 bp, from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp (e.g., about 1 kb).

In some embodiments, the primer sequences are in the range of between 10-75 nucleotides in length, such as 10 to 70 nucleotides, 12 to 65 nucleotides, 15 to 60 nucleotides, 20 to 55 nucleotides, 25 to 50 nucleotides, 30 to 45 nucleotides, and the like. In some embodiments, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest in some embodiments.

In some embodiments, the first and/or the second primer comprises a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); radioactive labels, e.g. $^{32}$P, $^{35}$S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In one non-limiting exemplary embodiment, where the target nucleic acid comprises Target Region 1d, where Target Region 1d is:

5'-ggacaggcgt cccactgctc gtcgcctgcc acccgcttcg gccacggcca gacgtccgcg gccttcctca gcgctctgct gccctcgcag ccgccgcgg cggccgtcaa cgccctgggg-3' (SEQ ID NO:63; corresponding to nucleotides 621-780 of SEQ ID NO:1), or the complement thereof, a suitable primer pair is:

Primer Pair A:

```
primer 1:
5'-ggacaggcgtccactgctc-3';      (SEQ ID NO: 64)
and primer 2:
5'-ccccagggcgttgacggccg-3'.     (SEQ ID NO: 65)
```

Target region 1d, and a suitable primer pair for amplifying a target nucleic acid comprising Target region 1d, are depicted in FIG. 10.

Primer pair A is suitable for use in methods of detecting a nucleotide substitution that is associated with pancreatic cancer. Primer pair A will in some embodiments be used to amplify a palladin nucleic acid comprising Target Region 1d. In some embodiments, the amplification product generated using Primer pair A and a nucleic acid target comprising Target Region 1d will then be analyzed using a nucleic acid probe that hybridizes to an detects a nucleotide substitution that is associated with pancreatic cancer, as described above. For example, any of probes 1-4 are suitable for use.

Primer pair A is also suitable for use in a method of detecting a palladin nucleic acid that is overexpressed in an indicator cell that is a cancerous or precancerous cell (e.g., a cancerous or precancerous pancreatic cell) or that is underexpressed in an indicator cell that is a white blood cell.

In other non-limiting exemplary embodiments, where the target nucleic acid comprises Target Region 1, where Target Region 1 is:

5'-ggaccctctgaagctccagcaactcca-gaaccaaatccgactggagcaggaggccggcgctcgg cagcctccgccagc-cccgcgcagcgcgccgccctcgcccccttcccgccgccgcccgccttcc ccgagctcgcggcctgcacgccgc-ccgcgtccccggagcccatgagcgcgctggcctcccgctc cgcccccgccatg-cagtcctccggctccttcaactacgcgcgccccaagcagttcatcgccgcg cagaacctcgggcccgcgtcgggccacg-gcacgccggcctccagcccagctcgtccagcctcc cgtcgcccatgtc-cccgacgccgaggcagttcggccgcgccccccgtgccgcccttcgcgcagcc cttcggcgctgagcccgaggc-cccgtggggctcctcctcgccgtcgcccccgccccgccaccc ccggtct-tcagccccacggctgccttcccggtgc-ccgacgtgttcccactgccgccgccaccac cgccgctcccgagcccgggacaggcgtc-ccactgctcgtcgcctgccacccgcttcggccacgg ccagacg Tccgcggccttcctcagcgctctgctgccctcgcagccgccgccggcggccgt-caac gccctggggctgcccaaggggtgtcaccccgc-3' (SEQ ID NO:6; corresponding to nucleotides 132-803 of SEQ ID NO:1, but including the C→T substitution, shown in bold and underlined), or the complement thereof, suitable primer pairs include:

Primer Pair B:
Primer 1: 5'-GGACCCTCTGAAGCTCCAGC-3' (SEQ ID NO:66); and
Primer 2: 5'-GCGGGGGTGACACCCTTGGG-3' (SEQ ID NO:67), where
Primer 1 of pair B corresponds to nucleotides 132-151 of SEQ ID NO:1; and Primer 2 of pair B corresponds to the complement of nucleotides 784-803 of SEQ ID NO:1.

Primer Pair C:
Primer 1: 5'-GGACCCTCTGAAGCTCCAGC-3' (SEQ ID NO:68); and
Primer 2: 5'-CCGTGGCCGAAGCGGGTGGCAGG-3' (SEQ ID NO:69), where
Primer 1 of pair C corresponds to nucleotides 132-151 of SEQ ID NO:1; and Primer 2 of pair C corresponds to the complement of nucleotides 685-707 of SEQ ID NO:1.

Primer Pair D:
  Primer 1: 5'-CCTCGCCGTCGCCCCCGCCC-3' (SEQ ID NO:70); and
  Primer 2: 5'-CCGTGGCCGAAGCGGGTGGCAGG-3' (SEQ ID NO:71), where
  Primer 1 of pair D corresponds to nucleotides 551 to 575 of SEQ ID NO:1; and Primer 2 of pair D corresponds to the complement of nucleotides 685-707 of SEQ ID NO:1.
Primer Pair E:
  Primer 1: 5'-CCTCGCCGTCGCCCCCGCCC-3' (SEQ ID NO:72); and
  Primer 2: 5'-CCGTGGCCGAAGCGGGTGGCAGG-3' (SEQ ID NO:73),
  where Primer 1 of pair E corresponds to nucleotides 551 to 575 of SEQ ID NO:1; and Primer 2 of pair E corresponds to the complement of nucleotides 685-707 of SEQ ID NO:1.

Primer pair B is suitable for use in methods of detecting a nucleotide substitution that is associated with cancer (e.g., pancreatic cancer). Primer pair B will in some embodiments be used to amplify a palladin nucleic acid comprising Target Region 1. In some embodiments, the amplification product generated using Primer pair B and a nucleic acid target comprising Target Region 1 will then be analyzed using a nucleic acid probe that hybridizes to and detects a nucleotide substitution that is associated with pancreatic cancer, as described above. For example, any of probes 1-4 are suitable for use.

Primer pair B is also suitable for use in a method of detecting a palladin nucleic acid that is overexpressed in a cancerous or precancerous pancreatic cell. Primer pairs C, D, and E are suitable for use in a method of detecting a palladin nucleic acid that is overexpressed in a cancerous or precancerous pancreatic cell.

Primer Pair F:

```
Primer 1:
5'-AGGTGTCACTTCTCTTTTTCCCCCC-3';     (SEQ ID NO: 74)
and

Primer 2:
5'-GGGGAGGGAAGTGGAGGACCGCGG-3',      (SEQ ID NO: 75)
``` where Primer 1 of pair F corresponds to nucleotides 139671 to 139695 of the genomic sequence depicted in FIG. 16; and where Primer 2 of pair F corresponds to the complement of nucleotides 140401 to 140425 of the sequence depicted in FIG. 16.

Primer pair F is suitable for use in methods of detecting a nucleotide substitution that is associated with cancer. Primer pair F will in some embodiments be used to amplify a genomic palladin nucleic acid comprising exon 2 (e.g., as shown in bold text in FIG. 16). In some embodiments, the amplification product generated using Primer pair F and a nucleic acid target comprising palladin exon 2 will then be analyzed using a nucleic acid probe that hybridizes to an detects a nucleotide substitution that is associated with cancer, as described above.

Primer Pair G:

```
Primer 1:
5'- cagtgggtta ccaacccag -3';        (SEQ ID NO: 76)
and

Primer 2:
5'-gtgcaccccgttctcacgca-3'.          (SEQ ID NO: 77)
```

Primer 1 of pair G corresponds to nucleotides 1641-1660 of SEQ ID NO:1; and Primer 2 of pair G corresponds to the complement of nucleotides 1721-1740 if SEQ ID NO:1.

Primer pair G is suitable for use in methods of detecting a nucleotide substitution that is associated with cancer. Primer pair G will in some embodiments be used to amplify a palladin nucleic acid comprising Target Region 3. In some embodiments, the amplification product generated using Primer pair G and a nucleic acid target comprising Target Region 3 will then be analyzed using a nucleic acid probe that hybridizes to and detects a nucleotide substitution that is associated with cancer, as described above.

Primer pair G is also suitable for use in a method of detecting a palladin nucleic acid that is overexpressed in an indicator cells that is a cancerous or precancerous cell (e.g., a cancerous or precancerous pancreatic cell), or that is underexpressed in an indicator cell that is a white blood cell Primer Pair H

```
Primer 1:
5' TCTTGTACTACTGAAGGAGGAATTTATGC;    (SEQ ID NO: 78)
and

Primer 2:
5' TTTTCCGTATTGGTTAGTAATGTAGAATTAG,  (SEQ ID NO: 79)
``` where Primer 1 of primer pair H corresponds to nucleotides 183428-18356 of BAC RP11-635L1 (GenBank Accession No. AC080188; as depicted in FIG. 14), and Primer 2 of primer pair H corresponds to the complement of nucleotides 183798-183828 of BAC RP11-635L1 (GenBank Accession No. AC080188; as depicted in FIG. 14). Primers 1 and 2 of primer pair H are underlined in the sequence set forth in FIG. 14.

Primer pair H is suitable for use in methods of detecting a nucleotide substitution that is associated with cancer. Primer pair H will in some embodiments be used to amplify a palladin nucleic acid comprising palladin exon 9 (as shown in bold text in FIG. 14). In some embodiments, the amplification product generated using Primer pair H and a nucleic acid target comprising palladin exon 9 will then be analyzed using a nucleic acid probe that hybridizes to and detects a nucleotide substitution that is associated with cancer, as described above.

Primer Pair I:

```
Primer 1:
5'-gggaaac gaacggagtc catccc-3';     (SEQ ID NO: 80)
and

Primer 2:
5'-agcaggacagctggtgttgg-3'.          (SEQ ID NO: 81)
```

Primer 1 of pair I corresponds to nucleotides 2034-2056 of the sequence depicted in FIGS. 13A and 13B (NM_016081); and Primer 2 of pair I corresponds to the complement of nucleotides 2111-2130 of the sequence depicted in FIGS. 13A and 13B (NM_016081).

Primer pair I is suitable for use in methods of detecting a nucleotide substitution that is associated with cancer. Primer pair G will in some embodiments be used to amplify a palladin nucleic acid comprising Target Region 4. In some embodiments, the amplification product generated using Primer pair G and a nucleic acid target comprising Target Region 4 will then be analyzed using a nucleic acid probe that hybridizes to an detects a nucleotide substitution that is associated with cancer, as described above. For example, any of probes 8-10 are suitable for use.

Primer pair I is also suitable for use in a method of detecting a palladin nucleic acid that is overexpressed in a cancerous or precancerous cell.

Primer Pair J

```
Primer 1:
5' CACAACACAGGGATTCTCAGAAGA      (SEQ ID NO: 82)

Primer 2:
5' AGCTGGTGTTGGAAGAGATT,         (SEQ ID NO: 83)
``` where primer 1 of pair J corresponds to nucleotides 26927-26950 of the genomic DNA sequence set forth in BAC RP11-592K15 (GenBank Accession No. AC084353; as depicted in FIG. 15), and Primer 2 of primer pair J corresponds to the complement of nucleotides 27294-27313 of BAC RP11-592K15 (GenBank Accession No. AC084353; as depicted in FIG. 15). Primers 1 and 2 of primer pair J are underlined in the sequence set forth in FIG. 15.

Primer pair J is suitable for use in methods of detecting a nucleotide substitution that is associated with cancer. Primer pair J will in some embodiments be used to amplify a palladin nucleic acid comprising at least a portion of palladin exon 10. In some embodiments, the amplification product generated using Primer pair J and a nucleic acid target comprising at least a portion of palladin exon 10 will then be analyzed using a nucleic acid probe that hybridizes to and detects a nucleotide substitution that is associated with cancer, as described above.

Primer Pair K

Primer 1: 5'-CCCCGCGCCCGGTCCGCGGA-3' (SEQ ID NO:115), corresponding to nucleotides 685-704 of the nucleotide sequence depicted in FIG. 19 and set forth in SEQ ID NO:110; and Primer 2: 5'-CGCGTCCGGAGCGAGCGGGA-3' (SEQ ID NO:116), corresponding to the complement of nucleotides 717-736 of the nucleotide sequence depicted in FIG. 19 and set forth in SEQ ID NO:110.

Primer pair K flanks the 12-base pair insertion depicted in FIG. 19; and is suitable for amplifying a target palladin nucleic acid that includes a nucleotide sequence insertion in a palladin promoter.

Internal Control Nucleic Acids

In certain embodiments, an internal control (IC) or an internal standard is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

In another embodiment, an IC, as described herein, is combined with RNA isolated from the sample according to standard techniques known to those of skill in the art, and described herein. The RNA is then reverse-transcribed using a reverse transcriptase to provide copy DNA. The cDNA sequences can be optionally amplified (e.g., by PCR) using labeled primers. The amplification products are separated, typically by electrophoresis, and the amount of radioactivity (proportional to the amount of amplified product) is determined. The amount of mRNA in the sample can then calculated where desired by comparison with the signal produced by the known standards.

Synthesis of Primers and Probes

Primers and probes described above are designed based on the sequences disclosed herein and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Compositions

The present invention further provides compositions comprising a nucleic acid suitable for use in a subject method (e.g., a nucleic acid probe as described above; a primer pair as described above). Compositions comprising a subject nucleic acid will in some embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like. In some embodiments, a subject nucleic acid is lyophilized.

Antibodies

Detection of a precancerous or cancerous cell (e.g., a cancerous or precancerous pancreatic cell, breast cancer cell, head and neck squamous cell carcinoma, etc.) can also be accomplished by detecting a palladin protein that is encoded by a palladin nucleic acid comprising a mutation associated with cancer, or by detecting a palladin protein that is present in an indicator cell at an abnormal level. For example, where the palladin gene mutation associated with cancer (e.g., pancreatic cancer, breast cancer, head and neck squamous cell cancer, etc.) results in a mutated palladin polypeptide, e.g., a palladin polypeptide that differs in amino acid sequence from "wild-type" palladin, the mutated palladin polypeptide can be detected. Detection of a mutated palladin polypeptide in a biological sample indicates the presence in the biological sample, or in a cell or tissue from which the biological sample was derived, of a precancerous or cancerous cell (e.g., a precancerous or cancerous pancreatic cell, precancerous or cancerous breast cell, head and neck squamous cell carcinoma, etc.).

As another example, the presence or absence of cancer in a subject is assessed by detecting an abnormal level of palladin polypeptide in an indicator cell (e.g., an elevated level in a pancreatic cell, breast cell, upper aerodigestive tract cell, axillary lymph node cell, etc., relative to a normal (non-cancerous) palladin polypeptide level; or decreased in a white blood cell relative to a normal white blood cell palladin polypeptide level in white blood cells of a non-cancerous subject). In this example, detection of a level of palladin polypeptide provides for detection of a cancerous or precancerous cell in the subject from whom the indicator cell was obtained.

The present invention provides antibody reagents, including isolated antibodies, which bind specifically to a palladin polypeptide, e.g., a palladin polypeptide comprising an epitope that includes an amino acid substitution encoded by a palladin gene mutation associated with pancreatic cancer. A palladin-specific antibody is useful for detecting a palladin polypeptide (including a mutant palladin polypeptide), and therefore finds use in certain embodiments in diagnostic methods, e.g., methods involving detection of pancreatic cancer. In certain embodiments, a palladin-specific antibody is isolated, e.g., is in an environment other than its naturally-occurring environment. Suitable anti-palladin antibodies include antibodies of any isotype; single-chain Fv; Fab; Fab; Fv; F(ab')$_2$; artificial antibodies; and the like. In some embodiments, the antibody is other than the 1E6 antibody described in Rachlin and Otey (2006) *J. Cell Sci.* 119:995-1004.

Suitable antibodies are obtained by immunizing a host animal with peptides comprising all or a portion of a palladin protein. Suitable host animals include mouse, rat sheep, goat, hamster, rabbit, etc. The host animal will generally be from a different species than the immunogen where the immunogen is from a naturally occurring source, e.g., a human sample, where representative host animals include, but are not limited to, e.g., rabbits, goats, mice, etc.

The immunogen may comprise the complete protein, or fragments and derivatives thereof. Generally, immunogens comprise all or a part of the protein, where these residues contain any post-translation modifications found on the native target protein. Immunogens are produced in a variety of ways known in the art, e.g., expression of cloned genes using conventional recombinant methods, preparation of fragments of a subject deacylase protein using well-known methods, etc.

For preparation of polyclonal antibodies, the first step is immunization of the host animal with the target protein, where the target protein can be in substantially pure form, comprising less than about 1% contaminant. The immunogen may comprise the complete palladin protein, fragments or derivatives thereof. To increase the immune response of the host animal, the palladin protein may be combined with an adjuvant, where suitable adjuvants include alum, dextran, sulfate, large polymeric anions, and oil-and-water emulsions, e.g. Freund's adjuvant, Freund's complete adjuvant, and the like. The palladin protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The palladin protein is administered to the host, e.g., intradermally or intramuscularly, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies include mouse, rat, hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) J.B.C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Anti-palladin antibodies also include "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell. Bio. 3:280), Rous sarcoma virus LTR (Gorman et al. (1982) P.N.A.S. 79:6777), and moloney murine leukemia virus LTR (Grosschedl et al. (1985) Cell 41:885); native Ig promoters, etc.

An anti-palladin antibody will in some embodiments be detectably labeled, e.g., with a radioisotope, an enzyme which generates a detectable product, a fluorescent protein, a chromogenic protein, and the like. An anti-palladin antibody may be further conjugated to other moieties, such as members of specific binding pairs, e.g., biotin (member of biotin-avidin specific binding pair), and the like. An anti-palladin antibody may also be bound to a solid support, including, but not limited to, polystyrene plates or beads, magnetic beads, test strips, membranes, and the like.

In some embodiments, the anti-palladin antibody is detectably labeled, either directly or indirectly. Direct labels include radioisotopes (e.g., $^{125}$I; $^{35}$S, and the like); enzymes whose products are detectable (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include second antibodies specific for palladin-specific antibodies, wherein the second antibody is labeled as described above; and members of specific binding pairs, e.g., biotin-avidin, and the like.

In some embodiments, an anti-palladin antibody comprises, covalently linked to the antibody, a protein that provides for a detectable signal. Suitable proteins include, but are not limited to, fluorescent proteins and enzymes (e.g., β-galactosidase, luciferase, horse radish peroxidase, alkaline phosphatase, etc.). Suitable fluorescent proteins include, but are not limited to, a green fluorescent protein (GFP), including, but not limited to, a GFP derived from *Aequoria victoria* or a derivative thereof, a number of which are commercially available; a GFP from a species such as *Renilla reniformis, Renilla mulleri*, or *Ptilosarcus guernyi*, as described in, e.g., WO 99/49019 and Peelle et al. (2001) *J. Protein Chem.* 20:507-519; any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

In some embodiments, an anti-palladin antibody is specific for a particular isoform of palladin. For example, in some embodiments, an anti-palladin antibody is specific for the 90 kD isoform of palladin. In other embodiments, an anti-palladin antibody is specific for the 140 kD isoform of palladin. In some embodiments, an anti-palladin antibody is specific for wild-type palladin, e.g., where "wild-type" palladin has an amino acid sequence that does not include mutations associated with pancreatic cancer.

In a particular embodiment, an anti-palladin antibody suitable for use in a diagnostic or detection method binds specifically to an epitope comprising amino acid 239 of the amino acid sequence depicted in FIG. 11. A diagnostic method could involve use of a first anti-palladin antibody specific for an epitope comprising amino acid 239 of the amino acid sequence depicted in FIG. 11, where amino acid 239 is Pro; and a second anti-palladin antibody specific for an epitope comprising amino acid 239 of the amino acid sequence depicted in FIG. 11, where amino acid 239 is Ser.

In another embodiment of interest, an anti-palladin antibody suitable for use in a diagnostic or detection method binds specifically to an epitope comprising amino acid 557 of the amino acid sequence depicted in FIG. 11. A diagnostic method could involve use of a first anti-palladin antibody specific for an epitope comprising amino acid 557 of the amino acid sequence depicted in FIG. 11, where amino acid 557 is Trp; and a second anti-palladin antibody specific for an epitope comprising amino acid 557 of the amino acid sequence depicted in FIG. 11, where amino acid 557 is Cys.

In another embodiment of interest, an anti-palladin antibody suitable for use in a diagnostic or detection method binds specifically to an epitope comprising amino acid 617 of the amino acid sequence depicted in FIG. 12. A diagnostic method could involve use of a first anti-palladin antibody specific for an epitope comprising amino acid 617 of the amino acid sequence depicted in FIG. 12, where amino acid 617 is Arg; and a second anti-palladin antibody specific for an epitope comprising amino acid 557 of the amino acid sequence depicted in FIG. 12, where amino acid 617 is Cys.

Diagnostic and Detection Methods

The present invention provides various diagnostic and detection methods relating to cancer (e.g., pancreatic cancer, breast cancer, head and neck squamous cell cancer, etc.). The invention provides methods for detection of the presence or absence of a pre-cancerous cell in a subject; methods for detection of the presence or absence of a cancerous cell in a subject; methods for identification of individuals at risk of developing cancer; methods for staging of cancer cells; and methods for assessing response to a treatment for cancer. The presence or absence of a cancerous or pre-cancerous cell can be detected either directly (e.g., by assessing a cell suspected of being cancerous for a palladin mutation or aberrant palladin expression level) or indirectly, by assessing a palladin expression level in a white blood cell.

For example, the invention provides methods for detection of a pre-cancerous pancreatic cell; methods for detection of a cancerous pancreatic cell; methods for identification of individuals at risk of developing pancreatic cancer; methods for staging of pancreatic cancer cells; and methods for assessing response to a treatment for pancreatic cancer. Nucleic acid probes and/or primers as discussed above can be used in a subject diagnostic or detection method. Similarly, anti-palladin antibodies are discussed above, and can be used in a subject diagnostic or detection method. These methods are described in detail below.

Detection and/or Diagnostic Methods Involving Assessing a Palladin mRNA Expression Level The present invention provides methods of diagnosing a cancerous or precancerous cancer (e.g., pancreatic cancer, breast cancer, head and neck squamous cell cancer, etc.) condition by detecting abnormal levels of palladin mRNA in a biological sample. The present invention provides methods of detecting a cancerous or pre-cancerous cell in a biological sample.

A subject method of diagnosing cancer, or detecting a cancerous or pre-cancerous cell in a biological sample, generally involves detecting the level of palladin mRNA in a cell in a biological sample, where a level of palladin mRNA in the cell that indicates that the palladin mRNA is overexpressed in the cell indicates that the cell is cancerous or pre-cancerous. In some embodiments, detection of a cancerous or precancerous cell indicates that an individual has cancer; and thus provides a diagnosis of cancer. In other embodiments, a subject method of diagnosing cancer involves detecting a level of a palladin mRNA in an indicator cell obtained from an individual, where a level of palladin mRNA in the indicator cell that is abnormally low indicates the presence in the individual of cancer.

For example, a subject method of diagnosing pancreatic cancer, or detecting a cancerous or pre-cancerous pancreatic cell in a biological sample, generally involves detecting the level of palladin mRNA in a pancreatic cell in a biological sample, where a level of palladin mRNA in the cell that indicates that the palladin mRNA is overexpressed in the cell indicates that the cell is cancerous or pre-cancerous. In some embodiments, detection of a cancerous or precancerous pancreatic cell indicates that an individual has pancreatic cancer; and thus provides a diagnosis of pancreatic cancer. In other embodiments, a subject method of diagnosing pancreatic cancer involves detecting a level of a palladin mRNA in an indicator cell obtained from an individual, where a level of palladin mRNA in the indicator cell that is abnormally low indicates the presence in the individual of pancreatic cancer.

In some embodiments, mRNA is isolated from pancreatic tissue or other biological sample obtained from an individual; the mRNA is reverse transcribed to generate a sample comprising a cDNA copy of a palladin mRNA; and a subject method involves detecting the level of palladin cDNA in the sample. In other embodiments, mRNA is isolated from pancreatic tissue obtained from an individual; the mRNA is reverse transcribed to generate a sample comprising a cDNA copy of a palladin mRNA; the palladin cDNA is amplified using a nucleic acid primer pair, generating a palladin amplification product; and a subject method involves detecting the level of palladin amplification product in the sample. In other embodiments, a probe that binds to a palladin nucleic acid that is overexpressed in pancreatic cancer is used, where a level of probe binding is correlated with a level of palladin expression.

Where a subject detection method detects the presence of a cancerous or precancerous pancreatic cell in an individual, in some embodiments the individual will undergo one or more confirmatory tests for pancreatic cancer. Where a subject detection method detects the presence of a cancerous or precancerous pancreatic cell in an individual, in some embodiments the individual will be treated for pancreatic cancer.

Treatments for pancreatic cancer include: surgery (e.g., pancreaticoduodenectomy; Whipple procedure; total pancreatectomy; partial pancreatectomy; distal pancreatectomy; etc.); radiation; chemotherapy; and combinations of two or more of the foregoing. Chemotherapy treatments include, but are not limited to, gemcitabine (Gemzar®) monotherapy; gemcitabine+erlotinib (Tarceva®; an epidermal growth factor receptor tyrosine kinase inhibitor); 5-fluorouracil; gemcitabine+erbitux; gemcitabine+bevacizumab; gemcitabine+ oxaliplatin; gemcitabine+cisplatin; etc. Gemcitabine is 2'-deoxy-2',2'-difluorocytidine; see, e.g., U.S. Pat. Nos. 5,464,826 and 6,555,518.

Where a subject detection method detects the presence of a cancerous or precancerous breast cell in an individual, in some embodiments the individual will undergo one or more confirmatory tests for breast cancer. Similarly, where a subject detection method detects the presence of a cancerous or precancerous cell in the upper aerodigestive tract in an individual, in some embodiments the individual will undergo one or more confirmatory tests for head and neck cancer.

Where a subject detection method detects the presence of a cancerous or precancerous breast cell in an individual, in some embodiments the individual will be treated for breast cancer. Similarly, where a subject detection method detects the presence of a cancerous or precancerous cell in the upper aerodigestive tract in an individual, in some embodiments the individual will be treated for head and neck squamous cell carcinoma.

Detection methods can also be performed to monitor progression of a cancer. For example, a biological sample is taken from the individual and tested at a frequency of once per week, twice weekly, once per month, bi-monthly, once every three months, once every four months, once every 6 months, or once a year, depending on various factors. The biological sample is tested for the level of palladin mRNA. The rate of increase in the level of palladin mRNA is an indication of the rate of progression of the cancer.

As an example, detection methods can also be performed to monitor progression of pancreatic cancer. For example, a biological sample is taken from the individual and tested at a frequency of once per week, twice weekly, once per month, bi-monthly, once every three months, once every four months, once every 6 months, or once a year, depending on various factors. The biological sample is tested for the level of palladin mRNA. The rate of increase in the level of palladin mRNA is an indication of the rate of progression of the disease (e.g., pancreatic cancer).

Detection methods can also be performed to assess response to therapy, e.g., therapy for pancreatic cancer, therapy for breast cancer, therapy for head and neck squamous cell carcinoma, etc. For example, where the pancreatic cancer is associated with an elevated level of palladin expression, the levels of palladin expression during the course of and/or following therapy can be assessed, thus providing an indicator of response to therapy. Measurements of palladin mRNA levels can be used to determine whether a patient is responding to treatment. In some embodiments, palladin mRNA levels are measured before and after a treatment, e.g. surgery or a drug treatment, to determine if the treatment is efficacious. In other embodiments, palladin mRNA levels are determined during the course of the treatment, to determine whether the treatment slows the progression of the disease, and to what extent the treatment slows the progression of the disease. For example, a reduction of at least about 10%, at least about 20%, at least about 25%, at least about 30%, or at least about 40% or more, in the rate of increase in the level of palladin mRNA in response to a given treatment indicates that the treatment is efficacious in treating pancreatic cancer.

Detection and/or Diagnostic Methods Involving Assessing a Palladin Polypeptide Level and/or Detecting Mutant Palladin Polypeptide Methods of diagnosing cancer, and methods of detecting a cancerous or precancerous cell, as described above, can also be carried out by detecting palladin polypeptide levels. Thus, the present invention provides methods of diagnosing cancer, and methods of detecting a cancerous or precancerous cell, where the methods generally involve detecting a level of palladin polypeptide in a biological sample. An abnormal level of palladin polypeptide in an indicator cell of a biological sample from an individual indicates the presence or absence of a cancerous or precancerous cell in the individual. For example, an elevated level of palladin polypeptide above normal levels in a cell suspected of being cancerous or precancerous can indicate that the individual has cancer. In another example, a decreased level of palladin polypeptide in a white blood cell of an individual relative to a normal level of palladin in a white blood cell of an unaffected subject can indicate that the individual has cancer. The source of palladin protein can be the same as the source of palladin nucleic acid. Sources of palladin nucleic acids are discussed above.

For example, methods of diagnosing pancreatic cancer, and methods of detecting a cancerous or precancerous pancreatic cell, as described above, can also be carried out by detecting palladin polypeptide levels. Thus, the present invention provides methods of diagnosing pancreatic cancer, and methods of detecting a cancerous or precancerous pancreatic cell, where the methods generally involve detecting a level of palladin polypeptide in a biological sample. An abnormal level of palladin polypeptide in a biological sample from an individual indicates the presence in the biological sample, and/or in the individual, of a cancerous or precancerous pancreatic cell. For example, an elevated level of palladin polypeptide above normal levels may indicate that the individual has pancreatic cancer.

Methods of diagnosing cancer, and methods of detecting a cancerous or precancerous cell, as described above, can also be carried out by detecting mutant palladin polypeptide. Thus, the present invention provides methods of diagnosing cancer, and methods of detecting a cancerous or precancerous cell, where the methods generally involve detecting mutant palladin polypeptide in a biological sample suspected of containing a cancerous or pre-cancerous cell, where the mutant palladin polypeptide is encoded by a palladin nucleic acid comprising one or more mutations associated with cancer.

Non-limiting examples of mutant palladin polypeptides that provide for diagnosis of cancer and/or detection of a cancerous or precancerous cell include: a) a palladin polypeptide comprising a Pro→Ser mutation at a position corresponding to amino acid 239 of the sequence depicted in FIG. 11 (GenBank BAA76836.1); b) a palladin polypeptide comprising a Trp→Cys mutation at a position corresponding to amino acid 557 of the sequence depicted in FIG. 11 (GenBank BAA76836.1); and c) an Arg→Cys mutation at a position corresponding to amino acid 617 of the sequence depicted in FIG. 12 (GenBank NP_057165.3).

For example, methods of diagnosing pancreatic cancer, and methods of detecting a cancerous or precancerous pancreatic cell, as described above, can also be carried out by detecting mutant palladin polypeptide. Thus, the present invention provides methods of diagnosing pancreatic cancer, and methods of detecting a cancerous or precancerous pancreatic cell, where the methods generally involve detecting mutant palladin polypeptide in a biological sample, where the mutant palladin polypeptide is encoded by a palladin nucleic acid comprising one or more mutations associated with pancreatic cancer. Non-limiting examples of mutant palladin polypeptides that provide for diagnosis of pancreatic cancer and/or detection of a cancerous or precancerous pancreatic cell include: a) a palladin polypeptide comprising a Pro→Ser mutation at a position corresponding to amino acid 239 of the sequence depicted in FIG. 11 (GenBank BAA76836.1); b) a palladin polypeptide comprising a Trp→Cys mutation at a position corresponding to amino acid 557 of the sequence depicted in FIG. 11 (GenBank BAA76836.1); and c) an Arg→Cys mutation at a position corresponding to amino acid 617 of the sequence depicted in FIG. 12 (GenBank NP_057165.3).

The palladin polypeptide that is being detected may be isolated, but need not be. In some embodiments, palladin polypeptide is isolated from a biological sample obtained from an individual. In other embodiments, palladin polypeptide is detected in crude cell lysates, in whole cells, or in partially purified preparations (e.g., total protein isolated from a biological sample). The biological sample is contacted with an anti-palladin antibody (e.g., an antibody that specifically binds palladin); and binding of the anti-palladin antibody to a protein in the sample is detected. Binding of the anti-palladin antibody to protein in the biological sample indicates the presence in the sample of palladin protein.

In some embodiments, the anti-palladin antibody is specific for the 90 kD isoform of palladin. In some of these embodiments, the anti-palladin antibody detects a level of palladin 90 kD isoform in the biological sample. In other embodiments, the anti-palladin antibody is specific for the 140 kD isoform of palladin. In some of these embodiments, the anti-palladin antibody detects a level of palladin 145 kD isoform in the biological sample.

Where a subject method involves detecting palladin polypeptide levels, palladin polypeptide levels can be measured using any standard method, including, but not limited to, immunoprecipitation, Western blotting, enzyme-linked immunosorbent assays (ELISA), radioimmunoassay, etc., where antibody specific for palladin polypeptide is employed. The anti-palladin antibody can include a detectable label, as described above. In some embodiments, a subject method that provides for detection of a palladin polypeptide level detects a level of wild-type palladin. Alternatively, the polypeptide can be detected using proteomic methods, such as mass spectroscopy. In other embodiments, a subject method that provides for detection of a palladin polypeptide level detects a level of palladin polypeptide containing one or more mutations associated with pancreatic cancer. In other embodiments, a subject method that provides for detection of a palladin polypeptide level detects both a level of wild-type and a level of mutated palladin.

Where a subject method involves detecting mutated palladin (e.g., palladin polypeptide comprising one or more mutations associated with cancer), the method will in some embodiments involve contacting a biological sample with one or more of: a) an anti-palladin antibody that binds specifically to an epitope comprising amino acid 239 of the amino acid sequence depicted in FIG. 11; b) an anti-palladin antibody that binds specifically to an epitope comprising amino acid 557 of the amino acid sequence depicted in FIG. 11; and c) an anti-palladin antibody that binds specifically to an epitope comprising amino acid 617 of the amino acid sequence depicted in FIG. 12.

In some embodiments, a subject method will involve detecting both wild-type and mutant palladin polypeptide. For example, a detection or diagnostic method will in some embodiments involve contacting a biological sample with: a) a first anti-palladin antibody specific for an epitope comprising amino acid 239 of the amino acid sequence depicted in FIG. 11, where amino acid 239 is Pro; and a second anti-palladin antibody specific for an epitope comprising amino acid 239 of the amino acid sequence depicted in FIG. 11, where amino acid 239 is Ser; b) a first anti-palladin antibody specific for an epitope comprising amino acid 557 of the amino acid sequence depicted in FIG. 11, where amino acid 557 is Trp; and a second anti-palladin antibody specific for an epitope comprising amino acid 557 of the amino acid sequence depicted in FIG. 11, where amino acid 557 is Cys; or c) a first anti-palladin antibody specific for an epitope comprising amino acid 617 of the amino acid sequence depicted in FIG. 12, where amino acid 617 is Arg; and a second anti-palladin antibody specific for an epitope comprising amino acid 557 of the amino acid sequence depicted in FIG. 12, where amino acid 617 is Cys.

Where a subject detection method detects the presence of a cancerous or precancerous cell in an individual, in some embodiments the individual will undergo one or more confirmatory tests for the cancer. Where a subject detection method detects the presence of a cancerous or precancerous cell in an individual, in some embodiments the individual will be treated for the cancer.

For example, where a subject detection method detects the presence of a cancerous or precancerous pancreatic cell in an individual, in some embodiments the individual will undergo one or more confirmatory tests for pancreatic cancer. Where a subject detection method detects the presence of a cancerous or precancerous pancreatic cell in an individual, in some embodiments the individual will be treated for pancreatic cancer.

Detection methods can also be performed to monitor progression of pancreatic cancer. For example, a biological sample is taken from the individual and tested at a frequency of once per week, twice weekly, once per month, bi-monthly, once every three months, once every four months, once every 6 months, or once a year, depending on various factors. The biological sample is tested for the level of palladin polypeptide, e.g., the level of mutant palladin polypeptide. The rate of increase in the level of palladin polypeptide is an indication of the rate of progression of the disease (e.g., pancreatic cancer).

Detection methods can also be performed to assess response to therapy. For example, where the pancreatic cancer is associated with an elevated level of palladin expression, the levels of palladin expression during the course of and/or following therapy can be assessed, thus providing an indicator of response to therapy. Measurements of palladin polypeptide levels can be used to determine whether a patient is responding to treatment. In some embodiments, palladin polypeptide levels are measured before and after a treatment, e.g. surgery or a drug treatment, to determine if the treatment is efficacious. In other embodiments, palladin polypeptide levels are determined during the course of the treatment, to determine whether the treatment slows the progression of the disease, and to what extent the treatment slows the progression of the disease. For example, a reduction of at least about 10%, at least about 20%, at least about 25%, at least about 30%, or at least about 40% or more, in the rate of increase in the level of palladin polypeptide in response to a given treatment indicates that the treatment is efficacious in treating the cancer (e.g., pancreatic cancer, breast cancer, head and neck squamous cell carcinoma, etc.).

Diagnostic Methods Involving Detection of Palladin Nucleic Acid Having a Cancer-Associated Nucleotide Substitution The present invention provides methods of determining the likelihood that an individual has or will develop cancer, the methods generally involving detecting a nucleotide substitution associated with cancer in a palladin target nucleic acid of the individual, e.g., a C→T nucleotide substitution at position 715 in a palladin nucleic acid, a G→T nucleotide substitution at position 1617 in a palladin nucleic acid, or a C→T nucleotide substitution at position 2060 in a palladin nucleic acid, as described above. The mutations in palladin, however, are not limited to the ones listed herein.

For example, the present invention provides methods of determining the likelihood that an individual has or will develop pancreatic cancer, the methods generally involving detecting a nucleotide substitution associated with pancreatic cancer in a palladin target nucleic acid of a pancreatic cell of the individual, e.g., a C→T nucleotide substitution at position 715 in a palladin nucleic acid, a G→T nucleotide substitution at position 1617 in a palladin nucleic acid, or a C→T nucleotide substitution at position 2060 in a palladin nucleic acid, as described above.

Detecting a nucleotide substitution associated with cancer in a palladin target nucleic acid can involve contacting the palladin target nucleic acid with a subject palladin probe under stringent hybridization conditions, where the subject palladin probe hybridizes only with a target palladin nucleic acid that comprises a nucleotide substitution associated with cancer; and detecting hybridization between the probe and the target. Hybridization between the probe and the target indicates that the individual has a palladin nucleic acid that includes a nucleotide substitution associated with cancer; and that the individual either has cancer, or has an increased risk of developing cancer compared to an individual who does not have a palladin nucleic acid that includes the nucleotide substitution.

Detection of a nucleotide substitution associated with cancer in a palladin target nucleic acid can involve use of a primer pair (which can be used with or without a probe), where the primer pair provides for amplification of a target nucleic acid such that the amplification product is produced at levels above background when a target palladin nucleic acid having the nucleotide substitution is present.

Detection of a nucleotide substitution associated with cancer in a palladin target nucleic acid can also be accomplished using a combination of primers and probes. For example, primer and probes described herein can be adapted for use in a detection system that provides for amplification and detection of the nucleotide substitution, e.g., in a real-time PCR assay. Exemplary systems, discussed in more detail herein, include Taqman™ systems, Amplifluor™ hairpin primer-based systems, Scorpion systems (e.g., bi-functional molecules containing a PCR primer element covalently linked to a probe element), Sunrise™ primer-based systems, Molecular Beacons, and a Light Upon Extension or LUX™-based systems.

Substitution can also be detected using any test that detects a change in the palladin sequence, including, but not limited to, restriction enzyme digestion or lack of digestion at the location of a substitution in palladin DNA or cDNA. For example, a nucleotide substitution can provide a sequence that is cut by a restriction endonuclease such as HindIII or PvuII, while the non-mutated sequence is not cut by the restriction endonuclease.

In some embodiments, the target palladin nucleic acid is palladin genomic DNA. In other embodiments, the target palladin nucleic acid is palladin mRNA, a cDNA copy of palladin mRNA, or an amplification product of palladin genomic DNA, palladin mRNA, or palladin cDNA.

Where the diagnostic method indicates that the individual has an increased risk of developing cancer, the risk that the individual will develop cancer is at least about 25%, at least about 50%, at least about 2-fold, at least about 2.5-fold, at least about 5-fold, at least about 10-fold, or at least about 20-fold, or more, higher than the risk that an individual without the nucleotide substitution associated with cancer.

For example, where the diagnostic method indicates that the individual has an increased risk of developing pancreatic cancer, the risk that the individual will develop pancreatic cancer is at least about 25%, at least about 50%, at least about 2-fold, at least about 2.5-fold, at least about 5-fold, at least about 10-fold, or at least about 20-fold, or more, higher than the risk that an individual without the nucleotide substitution associated with pancreatic cancer.

Where the diagnostic method indicates that the individual has an increased risk of developing cancer, in some embodiments the individual will be tested for the presence of cancer. Where the diagnostic method indicates that the individual has an increased risk of developing cancer, in some embodiments the individual will be monitored on a regular basis (e.g., monthly, bimonthly, twice a year, once a year, etc.) for cancer.

For example, where the diagnostic method indicates that the individual has an increased risk of developing pancreatic cancer, in some embodiments the individual will be tested for the presence of pancreatic cancer. Where the diagnostic method indicates that the individual has an increased risk of developing pancreatic cancer, in some embodiments the individual will be monitored on a regular basis (e.g., monthly, bimonthly, twice a year, once a year, etc.) for pancreatic cancer.

Diagnostic Methods Involving Detection of an Altered Palladin Gene Promoter

The present invention provides methods of detecting a cancerous or precancerous cell (e.g., a cancerous or precancerous pancreatic cell), the methods generally involving detecting an alteration in a palladin gene promoter. In some embodiments, the alteration being detected is in the 90 kDa isoform palladin gene promoter.

Alterations include, but are not limited to, insertions of nucleotide sequences, duplications of nucleotide sequences; deletions of nucleotide sequences; inversions of nucleotide sequences; and alterations in the methylation status of a promoter.

For example, the present invention provides methods of determining the likelihood that an individual has or will develop pancreatic cancer, the methods generally involving detecting a nucleotide sequence insertion associated with pancreatic cancer in a palladin target nucleic acid of a pancreatic cell of the individual, where the nucleotide sequence insertion is in a palladin gene promoter, as described above. In some embodiments, insertion of a 12-bp sequence in the 90 kDa isoform palladin promoter provides for detection of a cancerous or precancerous cell.

Methylation Status

The methylation status of a palladin gene promoter provides for detection of a cancerous or precancerous cell. For example, the methylation status of the 90 kDa isoform palladin promoter provides for detection of a cancerous or precancerous cell. Hypomethylation of the 90 kDa isoform palladin promoter indicates a cancerous or precancerous cell.

Any of a variety of methods can be used to detect DNA methylation status, where suitable methods include, but are not limited to, methylation-specific polymerase chain reaction (MSP; see, e.g., Herman et al. (1996) Proc. Natl. Acad. Sci. USA 93:9821-9826); MethylLight (Eads et al. (2000) Nucl. Acids Res. 28:E32; and U.S. Pat. No. 6,331,393); HeavyMethyl (Cottrell et al. (2004) Nucl. Acids Res. 32:e10); MethylQuant (Thomassin et al. (2004) Nucl. Acids Res. 32:e168; and the like.

A number of methods involve treatment of a target DNA with a bisulfite reagent, which converts unmethylated cytosines to uracils, leaving only methylated cytosines unchanged (see, e.g., WO 05/038051). Following bisulfite treatment, individual cytosine positions can be detected by a primer extension reaction (Gonzalgo and Jones (1997) Nucleic Acids Res. 25:2529-31; and WO 95/00669) or by enzymatic digestion (Xiong and Laird (1997) Nucleic Acids Res. 25: 2535-4). Alternatively, following bisulfite treatment, a methylation-specific polymerase chain reaction (PCR) can be carried out, using primers that bind either to methylated or unmethylated DNA only and that therefore selectively amplify only DNA with a defined methylation. MethylLight is a variation of MSP, and involves use of a methylation-specific real-time detection probe (MethyLight), which makes the assay both homogenous and quantitative. HeavyMethyl is also a variation on MSP. In the HeavyMethyl method, the priming is methylation specific, but non-extendable oligonucleotide blockers provide this specificity instead of the primers themselves. The blockers bind to bisulfite-treated DNA in a methylation-specific manner, and their binding sites overlap the primer binding sites. When the blocker is bound, the primer cannot bind and therefore the amplicon is not generated. When the blocker is not bound, the primer-binding site is accessible and the amplicon is generated. HeavyMethyl in combination with real-time detection with methylation-specific fluorogenic probes provides sensitive and specific detection of DNA methylation.

In some embodiments, a methylation-sensitive restriction endonuclease (e.g., a restriction endonuclease that recognizes and cleaves a nucleic acid having a particular nucleotide sequence only when the sequence is unmethylated), and/or a methylation-insensitive restriction endonuclease (e.g., a restriction endonuclease that recognizes and cleaves a nucleic acid having a particular nucleotide sequence, regardless of the methylation status of the nucleotide sequence); are used. The term "methylation-sensitive enzyme" refers to a restriction enzymes that does not cleave DNA (or cleaves DNA poorly) if one or more nucleotides in its recognition site are methylated. Suitable methylation-sensitive and methylation-insensitive restriction endonucleases that are suitable for use include, but are not limited to, MboI, DpnII, HpaII, BsmBI, Sau3A, and ClaI.

Various methods can be used to determine the methylation status of a target DNA. For example, indirect methods for DNA methylation pattern determinations at specific loci that have been developed rely on techniques that alter the genomic DNA in a methylation-dependent manner before an amplification event. Two exemplary methods that can be used to achieve this methylation-dependent DNA alteration include: 1) digestion by a restriction enzyme that is affected in its activity by 5-methylcytosine in a CpG sequence context. The cleavage, or lack of it, can subsequently be revealed by Southern blotting or by PCR; and 2) the treatment of genomic DNA with sodium bisulfite. Sodium bisulfite treatment converts all unmethylated cytosines in the DNA to uracil by deamination, but leaves the methylated cytosine residues intact. Subsequent PCR amplification replaces the uracil residues with thymines and the 5-methylcytosine residues with cytosines. The resulting sequence difference can be detected using standard DNA sequence detection techniques, e.g., PCR.

An exemplary method involves use of a bisulfite treatment-based method followed by a PCR reaction to analyze a target nucleic acid There are two principally different ways in which the sequence difference generated by the sodium bisulfite treatment can be revealed. The first is to design PCR primers that uniquely anneal with either methylated or unmethylated converted DNA. This technique is referred to as "methylation specific PCR" or "MSP". See, e.g., U.S. Pat. No. 5,786,146. The method used by all other bisulfite-based techniques (such as bisulfite genomic sequencing, COBRA and Ms-SNuPE) is to amplify the bisulfite-converted DNA using primers that anneal at locations that lack CpG dinucleotides in the original genomic sequence. In this way, the PCR primers can amplify the sequence in between the two primers, regardless of the DNA methylation status of that sequence in the original genomic DNA. This results in a pool of different PCR products, all with the same length and differing in their sequence only at the sites of potential DNA methylation at CpGs located in between the two primers. The difference between these methods of processing the bisulfite-converted sequence is that in MSP, the methylation information is derived from the occurrence or lack of occurrence of a PCR product, whereas in the other techniques a mix of products is always generated and the mixture is subsequently analyzed to yield quantitative information on the relative occurrence of the different methylation states. A method such as described in U.S. Pat. No. 7,186,512 is also suitable for use.

In some embodiments, the methods involve contacting a genomic sample of DNA with a modifying agent that modifies unmethylated cytosine (e.g., sodium bisulfite), to produce a converted nucleic acid; (b) amplifying the converted nucleic acid by means of oligonucleotide primers in the presence of one or a plurality of specific oligonucleotide probes, where the one or the plurality of the oligonucleotide primers or the specific probe(s) is/are capable of distinguishing between unmethylated and methylated nucleic acid (e.g., a CpG-specific probe capable of distinguishing between unmethylated and methylated nucleic acid); and (c) detecting, in real-time during the amplification, the methylated nucleic acid based on amplification-mediated probe displacement. See, e.g., U.S. Pat. No. 7,112,404. Amplification and detection can occur simultaneously as measured by fluorescence-based real-time quantitative PCR ("RT-PCR") using specific, dual label TaqMan® oligonucleotide probes. The displaceable probes can be specifically designed to distinguish between methylated and unmethylated CpG sites present in the original, unmodified nucleic acid sample. Sodium-bisulfite readily reacts with the 5,6-double bond of cytosine, but not with methylated cytosine, to produce a sulfonated cytosine intermediate that undergoes deamination under alkaline conditions to produce uracil. Because Taxi polymerase recognizes uracil as thymine and 5-methylcytidine (m5C) as cytidine, the sequential combination of sodium bisulfite treatment and PCR amplification results in the ultimate conversion of unmethylated cytosine residues to thymine (C→U→T) and methylated cytosine residues ("mC") to cytosine (mC→mC→C). Thus, sodium-bisulfite treatment of genomic DNA creates methylation-dependent sequence differences by converting unmethylated cytosines to uracil, and upon PCR the resultant product contains cytosine only at positions where methylated cytosine occurs in the unmodified nucleic acid.

In some embodiments, the specific primers are designed to be substantially complementary to each strand of the genomic locus of interest. Typically, one primer is complementary to the negative, (−) strand of the locus (the "lower" strand of a horizontally situated double-stranded DNA molecule) and the other is complementary to the positive (+) strand ("upper" strand). In some embodiments, the primers are designed to overlap potential sites of DNA methylation (CpG nucleotides) and specifically distinguish modified unmethylated from methylated DNA. This sequence discrimination can be based upon the differential annealing temperatures of perfectly matched, versus mismatched oligonucleotides. In some embodiments, primers are typically designed to overlap from one to several CpG sequences. In other embodiments, e.g., in a quantitative embodiment, the primers do not overlap any CpG sequences.

Staging Methods Involving Analysis of Palladin Expression Levels

The present invention provides methods of staging cancer, the methods generally involving determining a level of palladin mRNA in a cell; and, based on the level of palladin mRNA, assigning the cell to a cancerous stage.

For example, in some embodiments, where the level of palladin mRNA in a cell is from about 2-fold higher to about 5-fold higher than the level of palladin mRNA in a normal, non-cancerous cell of the same cell type, the cell is designated stage I.

In some embodiments, where the level of palladin mRNA in a cell is from about 5-fold higher to about 10-fold higher than the level of palladin mRNA in a normal, non-cancerous cell of the same cell type, the cell is designated stage 11.

In some embodiments, where the level of palladin mRNA in a cell is from about 10-fold higher to about 50-fold higher than the level of palladin mRNA in a normal, non-cancerous cell of the same cell type, the cell is designated stage III.

These stage designations can be applied to any cancer associated with abnormal expression of palladin, e.g., pancreatic cancer, breast cancer, head and neck cancer, etc.

For example, the present invention provides methods of staging pancreatic cancer, the methods generally involving determining a level of palladin mRNA in a pancreatic cell; and, based on the level of palladin mRNA, assigning the pancreatic cell to a cancerous stage.

For example, in some embodiments, where the level of palladin mRNA in a pancreatic cell is from about 2-fold higher to about 5-fold higher than the level of palladin mRNA in a normal, non-cancerous pancreatic cell of the same cell type, the pancreatic cell is designated stage I.

In some embodiments, where the level of palladin mRNA in a pancreatic cell is from about 5-fold higher to about 10-fold higher than the level of palladin mRNA in a normal, non-cancerous pancreatic cell of the same cell type, the pancreatic cell is designated stage 11.

In some embodiments, where the level of palladin mRNA in a pancreatic cell is from about 10-fold higher to about 50-fold higher than the level of palladin mRNA in a normal, non-cancerous pancreatic cell of the same cell type, the pancreatic cell is designated stage III.

Stage I disease could be considered local cancer (within the organ that contains the cancer). Stage 11 disease could be considered regional (cancer extending beyond the organ of origin into the adjacent structures and lymph nodes), Stage III disease could be considered widespread or metastatic disease (spread of the cancer to areas remote from the organ of origin). Thus, the present methods provide for staging cancer metastasis.

Hybridization and Amplification Methods for Use in a Detection or Diagnostic Method The diagnostic, detection, staging methods described above will in many embodiments involve nucleic acid hybridization with a nucleic acid probe, nucleic acid amplification with a nucleic acid primer pair, or both. Nucleic acid hybridization and nucleic acid amplification methods are known to those skilled in the art. Exemplary nucleic acid hybridization and nucleic acid amplification methods are discussed in detail below. The following provides detail of exemplary nucleic acid-based methods for detection, and examples of how such can be adapted for use in the methods of the invention.

Detection and Diagnostic Methods Using Hybridization with a Nucleic Acid Probe

As discussed above, where a subject detection or diagnostic method involves detecting a nucleotide sequence alteration (e.g., a C→T nucleotide substitution at position 715 in a palladin nucleic acid), the method will in some embodiments comprise hybridizing a target palladin nucleic acid with a nucleic acid probe. Also as discussed above, where a subject method involves detecting a level of a palladin nucleic acid in a cell, the method will in some embodiments comprise hybridizing a target palladin nucleic acid with a nucleic acid probe. Nucleic acid hybridization methods that are suitable for use in a subject method are described below.

In some embodiments, a subject method for detecting a nucleotide sequence alteration associated with cancer involves contacting, under stringent hybridization conditions, a subject nucleic acid probe with a target palladin nucleic acid, where the subject probe hybridizes only to a target palladin nucleic acid that comprises a nucleotide sequence alteration associated with cancer (e.g., a nucleotide substitution as described above; a nucleotide insertion as described above); and detecting hybridization between the probe and the target. Hybridization of the palladin nucleic probe to the target palladin nucleic acid indicates that the target palladin nucleic acid comprises a nucleotide sequence alteration that is associated with cancer.

For example, in some embodiments, a subject method for detecting a nucleotide sequence alteration associated with pancreatic cancer involves contacting, under stringent hybridization conditions, a subject nucleic acid probe with a target palladin nucleic acid, where the subject probe hybridizes only to a target palladin nucleic acid that comprises a nucleotide sequence alteration associated with pancreatic cancer (e.g., a nucleotide sequence alteration as described above); and detecting hybridization between the probe and the target. Hybridization of the palladin nucleic probe to the target palladin nucleic acid indicates that the target palladin nucleic acid comprises a nucleotide sequence alteration that is associated with pancreatic cancer.

In some embodiments, a subject method for detecting a cancerous or pre-cancerous cell involves contacting, under stringent hybridization conditions, a subject nucleic acid probe with a target palladin nucleic acid in a sample; and detecting the level of palladin mRNA in the sample. Where the detected level of palladin mRNA indicates that palladin mRNA is overexpressed in the cell, the cell is considered cancerous or precancerous. In some of these embodiments, the palladin target nucleic acid is first amplified using a subject primer pair.

For example, in some embodiments, a subject method for detecting a cancerous or pre-cancerous pancreatic cell involves contacting, under stringent hybridization conditions, a subject nucleic acid probe with a target palladin nucleic acid in a sample; and detecting the level of palladin mRNA in the sample. Where the detected level of palladin mRNA indicates that palladin mRNA is overexpressed in the cell, the cell is considered cancerous or precancerous. In some of these embodiments, the palladin target nucleic acid is first amplified using a subject primer pair.

A number of methods are available for analyzing nucleic acids for the presence and/or level of a specific nucleic acid in a cell. The mRNA may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33.

In some embodiments, the method involves contacting the sample under stringent hybridization conditions with a subject palladin nucleic acid probe and detecting binding, if any, of the probe to a nucleic acid in the sample. A variety of nucleic acid hybridization methods are well known to those skilled in the art, and any known method can be used. In many embodiments, the palladin nucleic acid probe will be detectably labeled.

Detection and Diagnostic Methods Using Amplification with Nucleic Acid Primer Pairs As discussed above, where a subject detection or diagnostic method involves detecting a nucleotide sequence alteration, which is associated with cancer, in a palladin nucleic acid, the method will in some embodiments include amplification of a target palladin nucleic acid, forming a palladin amplification product; and hybridizing the palladin amplification product with a nucleic acid probe that detects the nucleotide sequence alteration. Also as discussed above, where a subject method involves detecting a level of a palladin nucleic acid in a cell, the method will in some embodiments include amplification of a target palladin nucleic acid, forming a palladin amplification product (and may further include a step of hybridizing the palladin amplification product with a nucleic acid probe).

In some embodiments, the method involves contacting a sample (e.g., under stringent hybridization conditions) with a subject nucleic acid primer pair, where the primer pair, under conditions that permit primer-initiated nucleic acid amplification, amplifies any target palladin nucleic acid present in the sample, generating an amplification product (where amplification product is generated when target palladin nucleic acid present in the sample).

Conditions that permit primer-initiated nucleic acid amplification and catalytic nucleic acid activity are well known to those skilled in the art, and include the presence of a DNA polymerase; deoxynucleotide triphosphates; and magnesium ions. Suitable reaction conditions are well known to those skilled in the art of nucleic acid amplification. Exemplary, non-limiting reaction conditions are described in the Examples. The DNA polymerase is generally one that has high affinity for binding at the 3'-end of an oligonucleotide hybridized to a nucleic acid strand. The DNA polymerase is generally one that has little or no 5'→3' exonuclease activity so as to minimize degradation of primer, termination or primer extension polynucleotides. The DNA polymerase is generally one that has little to no proofreading activity. In many embodiments, the DNA polymerase is thermostable, e.g., is catalytically active at temperatures in excess of about 75° C. DNA polymerases that are suitable for use in a subject method include, but are not limited to, DNA polymerases discussed in U.S. Pat. Nos. 5,648,211 and 5,744,312, which include exo⁻ Vent (New England Biolabs), exo⁻ Deep Vent (New England Biolabs), Bst (BioRad), exo⁻ Pfu (Stratagene), Bca (Panvera), sequencing grade Taq (Promega); thermostable DNA polymerases from *Thermoanaerobacter thermohydrosulfuricus*; and the like. In some embodiments, the reaction mixture includes an RNAse H.

Magnesium ions are typically present in the reaction mix in a concentration of from about 1 mM to about 100 mM, e.g., from about 1 mM to about 3 mM, from about 3 mM to about 5 mM, from about 5 mM to about 10 mM, from about 10 mM to about 25 mM, from about 25 mM to about 50 mM, from about 50 mM to about 75 mM, or from about 75 mM to about 100 mM.

Usually the reaction mixture will comprise four different types of dNTPs corresponding to the four naturally occurring bases are present, i.e. dATP, dTTP, dCTP and dGTP. In the subject methods, each dNTP will typically be present at a final concentration in the reaction, ranging from about 10 μM to 5000 μM, e.g., from about 10 μM to about 50 μM, from about 50 μM to about 100 μM, from about 100 μM to about 200 μM, from about 200 μM to about 500 μM, from about 500 μM to about 1000 μM, from about 1000 μM to about 2000 μM, from about 2000 μM to about 3000 μM, from about 3000 μM to about 4000 μM, or from about 4000 μM to about 5000 μM. In some embodiments, each dNTP will be present at a final concentration in the reaction of from about 20 μM to 1000 μM, from about 100 μM to about 200 μM, or from about 50 μM to about 200

The amplification reaction mixture typically includes an aqueous buffer medium that includes a source of monovalent ions, a source of divalent cations and a buffering agent. Any convenient source of monovalent ions, such as KCl, K-acetate, NH₄-acetate, K-glutamate, NH₄Cl, ammonium sulfate, and the like may be employed. The divalent cation may be magnesium, manganese, zinc and the like, where the cation will typically be magnesium. Any convenient source of magnesium cation may be employed, including MgCl₂, Mg-acetate, and the like. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain embodiments the buffering agent will be present in an amount sufficient to provide a pH ranging from about 6.0 to 9.5, e.g., pH 7.3 at 72° C. Other agents which may be present in the buffer medium include chelating agents, such as EDTA, EGTA and the like.

Each primer nucleic acid is present in the reaction mixture at a concentration of from about 50 nM to about 900 nM, e.g., the 3' primer and the 5' primer nucleic acid are each independently present at a concentration of from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 400 nM, from about 400 nM to about 500 nM, from about 500 nM to about 600 nM, from about 600 nM to about 700 nM, from about 700 nM to about 800 nM, or from about 800 nM to about 900 nM.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In one embodiment, a subject method involves amplifying nucleic acids from a sample, which amplifying step follows a reverse transcription step to provide a cDNA template for amplification. If a diagnostic nucleic acid is obtained, the presence or absence of a nucleotide substitution associated with cancer (e.g., pancreatic cancer, breast cancer, head and neck cancer, etc.) can be indicated, where the presence of a nucleotide substitution associated with pancreatic cancer indicates an increased likelihood that the individual from whom the nucleic acid was obtained has or will develop cancer (e.g., pancreatic cancer, breast cancer, head and neck cancer, etc.). In other embodiments, the level of a palladin mRNA can be indicated, where overexpression of a palladin mRNA indicates a cancerous or precancerous cell. In general, amplification-based methods involve reverse transcription of mRNA in a sample and amplifying the resulting cDNA from the sample using a primer and at least one other primer, as described above, and assessing the amplified nucleic acids.

As is known in the art, an amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect palladin target nucleic acid (e.g., to detect a nucleotide substitution associated with pancreatic cancer; to detect a level of palladin mRNA; etc.) in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, e.g. by heat, and hybridized with first and second primers which are present in molar excess. Polymerization is catalyzed in the presence of the four deoxyribonucleotide triphosphates (dNTPs-dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stearothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. PCR is typically carried out with a commercially available thermal cycler, e.g., Perkin Elmer.

RNAs encoding a deacylase of interest can be amplified by reverse transcribing the mRNA into cDNA, and then performing PCR (RT-PCR), as described above. Alternatively, a single enzyme may be used for both steps as described in U.S. Pat. No. 5,322,770. mRNA may also be reverse transcribed into cDNA, followed by asymmetric gap ligase chain reaction (RT-AGLCR) as described by Marshall et al. (1994) PCR Meth. App. 4:80-84.

The fluorogenic 5' nuclease assay, known as the TAQMAN™ assay (Perkin-Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of a palladin nucleic acid as described herein can be used in TAQMAN™ analyses to detect the presence of a nucleotide substitution associated with pancreatic cancer and/or to detect a level of palladin mRNA in a biological sample. Analysis is performed in conjunction with thermal cycling by monitoring the generation of fluorescence signals. The assay system dispenses with the need for gel electrophoretic analysis, and has the capability to generate quantitative data allowing the determination of, for example, the level of palladin mRNA (e.g., to detect the presence of a cancerous pancreatic cell; to detect the presence of a pre-cancerous pancreatic cell; to stage a pancreatic tumor; etc.).

The fluorogenic 5' nuclease assay is conveniently performed using, for example, AMPLITAQ GOLD™ DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, the present invention provides methods for amplifying a target palladin nucleotide sequence using a nucleic acid polymerase having 5' to 3' nuclease activity, one or more primers capable of hybridizing to the target sequence or its extension product, and an oligonucleotide probe capable of hybridizing to the target sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is in some embodiments a fluorescein dye and the quencher molecule is in some embodiments a rhodamine dye.

The palladin target nucleic acids described herein may also be used as a basis for transcription-mediated amplification (TMA) assays. TMA provides a method of identifying target nucleic acids present in very small amounts in a biological sample. Such nucleic acids may be difficult or impossible to detect using direct assay methods. In particular, TMA is an isothemal, autocatalytic nucleic acid target amplification system that can provide more than a billion RNA copies of a target sequence. The assay can be done qualitatively, to accurately detect the presence or absence of the target sequence in a biological sample. The assay can also provide a quantitative measure of the amount of target sequence over a concentration range of several orders of magnitude. TMA provides a method for autocatalytically synthesizing multiple copies of a target nucleic acid sequence without repetitive manipulation of reaction conditions such as temperature, ionic strength and pH.

Generally, TMA includes the following steps: (a) isolating nucleic acid from the biological sample of interest (e.g., pancreatic tissue; pancreatic cell(s); tissue adjacent pancreatic tissue; etc.); and (b) combining into a reaction mixture (i) the isolated nucleic acid, (ii) first and second oligonucleotide primers, the first primer having a complexing sequence sufficiently complementary to the 3' terminal portion of an RNA target sequence, if present (for example the (+) strand), to complex therewith, and the second primer having a complexing sequence sufficiently complementary to the 3' terminal portion of the target sequence of its complement (for example, the (−) strand) to complex therewith, wherein the first oligonucleotide further comprises a sequence 5' to the complexing sequence which includes a promoter, (iii) a reverse transcriptase or RNA and DNA dependent DNA polymerases, (iv) an enzyme activity which selectively degrades the RNA strand of an RNA-DNA complex (such as an RNAse H) and (v) an RNA polymerase which recognizes the promoter.

The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient to provide multiple copies of the target sequence. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. The reaction conveniently does not require a denaturation step to separate the RNA-DNA complex produced by the first DNA extension reaction.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. In some embodiments, an exogenous RNAse H, such as *E. coli* RNAse H, is added, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Another method of detection involves use of target sequence-specific oligonucleotide probes, which contain a region of complementarity to the target sequence described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. In some embodiments, the differential hydrolysis step is conducted at the same temperature as the hybridization step, typically at 50 to 70 degrees celsius. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948, 899; and 5,283,174, the disclosures of which are incorporated by reference herein in their entireties.

TMA is described in detail in, e.g., U.S. Pat. No. 5,399,491, the disclosure of which is incorporated herein by reference in its entirety. In one example of a typical assay, an isolated nucleic acid sample, suspected of containing a deacylase-encoding nucleic acid as described herein, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

Oligonucleotides will in some embodiments be used in nucleic acid sequence-based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's. Using NASBA, large amounts of single-stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The target palladin nucleic acids described herein are also useful in nucleic acid hybridization and amplification techniques that utilize branched DNA molecules. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849, 481, incorporated herein by reference in its entirety.

As is readily apparent, design of the assays described herein is subject to a great deal of variation, and many formats are known in the art. The above descriptions are merely provided as guidance and one of skill in the art can readily modify the described protocols, using techniques well known in the art.

Kits

The invention further provides a kit for use in a subject method. Kits provide components for detection of palladin nucleic acid and/or palladin polypeptide.

Kits for Detecting Palladin Nucleic Acid

A subject kit comprises a pair of nucleic acids (primer pairs), one or more nucleic acid probes, or both, where the primer pairs and probes are suitable for use in a subject method, as described above. The nucleic acids will in some embodiments be present in a suitable storage medium, e.g., buffered solution, typically in a suitable container. The kit includes the primers and/or probes, and may further include a buffer; reagents (e.g., for polymerase chain reaction (e.g., deoxynucleotide triphosphates (dATP, dTTP, dCTP, and dGTP), a thermostable DNA polymerase, a buffer suitable for polymerase chain reaction, a solution containing $Mg^{2+}$ ions (e.g., $MgCl_2$), and other components well known to those skilled in the art for carrying out a polymerase chain reaction)). The kit may further include instructions for use of the kit, which instructions may be provided in a variety of forms, e.g., as printed information, on a compact disc, and the like. The kit may further include reagents necessary for extraction of DNA (or mRNA) from a biological sample (e.g., pancreatic tissue; pancreatic cells; ductal pancreatic epithelial cells; lymphocytes; peripheral white blood cells; etc.) from an individual. The kit may further include reagents necessary for reverse transcription of an mRNA, to make a cDNA copy of the mRNA.

The kit may further include positive and negative controls. An example of a positive control is a palladin nucleic acid that includes a region that will be amplified by primer pairs included in the kit. An example of a negative control is a nucleic acid (e.g., an albumin-encoding nucleic acid) that will not be amplified by nucleic acid primers included in the kit. The kits are useful in diagnostic applications, as described in detail above. For example, in some embodiments, a subject kit is useful to determine whether a given DNA sample (or an mRNA sample) obtained from an individual comprises a nucleotide substitution associated with pancreatic cancer. In other embodiments, a subject kit is useful to determine whether a palladin mRNA is present at higher or lower than normal levels in a pancreatic cell or other cell.

A kit will in some embodiments provide a standard for normalization of a level of a palladin polynucleotide to a standard, e.g., a level of a glucose-6-phosphate dehydrogenase polynucleotide (e.g, a G6PDH mRNA or cDNA copy of a G6PDH mRNA).

Exemplary kits include at least one primer, at least two primers (a 5' and a 3' primer), or at least two primers and a probe, as described above. Also included in the subject kits may be buffers, dNTPs, and controls, (e.g., positive and negative control nucleic acids) for performing the subject methods. Primers in the subject kits may be detectably labeled or unlabeled).

Kits for Detecting Palladin Polypeptide

A subject kit for detecting palladin polypeptide comprises one or more anti-palladin antibody reagents. For example, a subject kit will include one or more of: a) an anti-palladin antibody specific for the 90 kD isoform of palladin; b) an anti-palladin antibody specific for the 140 kD isoform of palladin; c) an anti-palladin antibody that binds specifically to an epitope comprising amino acid 239 of the amino acid sequence depicted in FIG. 11; d) an anti-palladin antibody that binds specifically to an epitope comprising amino acid 557 of the amino acid sequence depicted in FIG. 11; and e) an anti-palladin antibody that binds specifically to an epitope comprising amino acid 617 of the amino acid sequence depicted in FIG. 12. In some embodiments, the anti-palladin antibody will comprise a detectable label. In some embodiments, the anti-palladin antibody will be bound to an insoluble support, e.g., a bead (e.g., a polystyrene bead, a magnetic bead, etc.); a plastic surface (e.g., the well of an ELISA plate); a membrane (e.g., a test strip; a polyvinylpyrrolidone membrane; a nitrocellulose membrane; etc.); and the like.

A subject kit can further include, if desired, one or more of various conventional components, such as, for example, containers with one or more buffers (e.g., wash buffers), detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized.

A kit will in some embodiments provide a standard for normalization of a level of a palladin polypeptide to a standard, e.g., a level of an actin polypeptide, a level of a GAPDH polypeptide, etc. A kit will in some embodiments further include negative controls, e.g., antibodies specific for a non-palladin polypeptide; and the like.

Kits may also include components for conducting western blots (e.g., pre-made gels, membranes, transfer systems, etc.); components for carrying out ELISAs (e.g., 96-well plates; plates containing wells in multiples of 96); components for carrying out immunoprecipitation (e.g. protein A); columns, especially spin columns, for affinity or size separation of palladin polypeptide from other (non-palladin) polypeptides or separation of a first palladin isoform from a second palladin isoform (e.g. gel filtration columns, antibody columns, size exclusion columns, membrane cut-off spin columns etc.).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); U, units; s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Identification and Characterization of a Palladin Gene Mutation

Summary

Figure 2:
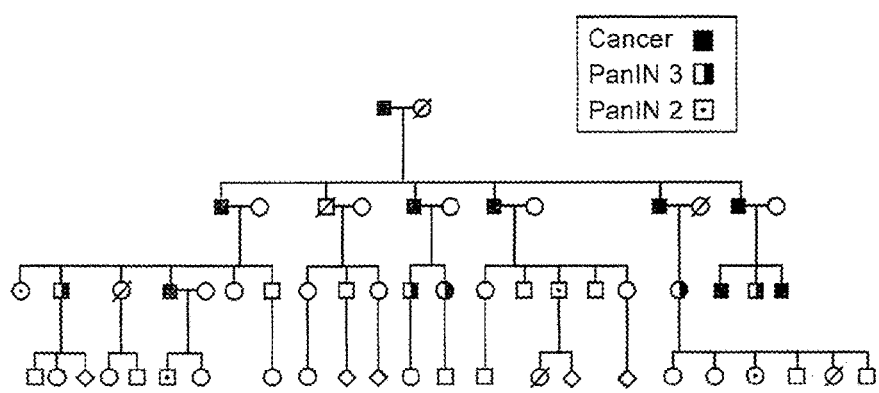
FIG. 2 depicts a pedigree of Family X.

A large kindred (Family X) was identified, which inherits pancreatic cancer in an autosomal dominant fashion with high penetrance. In order to identify living affected familial members prior to the onset of cancer, an endoscopic surveillance program was developed that assists in the detection of pancreatic pre-cancer (also called pancreatic intraepithelial neoplasia or PanIN). Family X includes 18 cases in 4 generations of either cancer (n=9) or histologically proven pre-cancer (n=9) (FIG. 2). In FIG. 2, nine members of this family were diagnosed with pancreatic cancer, and nine with pancreatic precancer (five with carcinoma in situe (PanIN 3); and four with low-grade dysplasia (PanIN 2)).

A pancreatic cancer susceptibility locus was mapped to 4q32-34. Identification of the gene of interest in this region represented a considerable challenge because of the size (16 MB) and the number of genes localized to this region (approximately 250). To narrow the region, a custom microarray of the genes and expressed sequence tags located at 4q32-34 was created. Palladin, one of the candidate genes that showed the highest up-regulation in the array analysis, was assessed further and a C to T base pair substitution was identified in the highly conserved region of palladin in all of the affected family members. The Palladin gene is highly conserved through evolution; it is a cytoskeletal protein and a component of actin-containing microfilaments that control cell shape, adhesion, and motility.

Methods

Tissues and RNAs

Pancreatic adenocarcinoma tissue samples were collected from the University of Washington, Cleveland Clinic, and University of Pittsburgh with authorized IRB approval. Details of tissue collection, RNA preparation and RNA labeling for microarrays were previously described (Pogue-Geile et al. (2004) *Cancer Genomics and Proteomics* 1:371-386). Normal pancreas samples were obtained commercially from Stratagene, Clontech, Biochain, Chemicon, and Ambion and from normal pancreatic surgical specimens obtained through the University of Washington. In case of the surgical specimens, the histologic normalcy of the tissue was ascertained by pathologist Dr. Mary Bronner and for tissues obtained at the University of Pittsburgh by pathologist at the University of Pittsburgh.

Microarray Construction Hybridization and Analysis

Unigenes were identified using the UCSC genome maps (available on the internet at genome.ucsc.edu; Kent et al) and NCBI maps. 243 unigenes clones mapping between markers D4S413-D4S299 were identified. Seventeen clones were included as housekeeping genes and 25 additional clones were included because of their location in a region of the genome that is frequently lost in pancreatic cancer. Clones were acquired from Research Genetics, (now Invitrogen) and from RZPD (German Resource Center for Genome Research) and from University of Pittsburgh Genomics and Proteomics Core Laboratories. Identification of all clones and accurate location on chromosome 4q was confirmed by sequence analysis using Big Dye. Clones were amplified, purified and arrayed onto glass slides as previously described (Pogue-Geile et al. (2004) *Cancer Genomics Proteomics* 1:371).

Slides were scanned with the GMS 418 scanner (Genetic MicroSystems). The Cy-5 was and Cy-3 images were overlaid, and raw data was generated for both channels using the ImaGene program United (Bioinformatics Inc, Calgary AB).

QRT-PCR

QRT-PCR was carried out using the 5' nuclease assay and an Applied Biosystems 7700 Sequence Detection Instrument (TaqMan). Tissues used for expression analysis utilized whole tissues. Palladin expression was measured relative to the endogenous control, GAPDH, using the comparative $C_T$ method described previously (Godfrey et al. 2000). cDNAs were generated at 2 different RNA input concentrations (10 ng/μl and 4 ng/μl) and TaqMan reactions with the endogenous control were run in duplicate from both RT reactions. Palladin TaqMan reactions were carried out in triplicate using RT reactions with 10 ng/μl reactions. A calibrator RNA, composed of 50 ng/μl universal reference RNA (Stratagene, cat no 40000-41) and 50 ng/μl colon RNA (Ambion cat no 7986) was included on every amplification plate to allow comparison of samples run at different times. RT-negative controls were run on each plate to ensure that no amplification occurred in the absence of cDNA.

Statistical Analysis

Microarray analysis was performed using the Gene Expression Differential Analysis tool (caGEDA) a web application specifically developed for cancer microarray data analysis at http://bioinformatics(dot)upmc(dot)edu/GE2/GEDA(dot)html (Patel and Lyons-Weiller). The J5 test was used; and the data were normalized with log 2 and Z transformation.

Sequence Analysis

A restriction enzyme assay can be used to detect the specific family X mutation. First, PCR was performed with Fast Start Taq from Roche using 30 μg genomic DNA, with 200 μM dNTPs, 20% GC-rich solution, 0.04 U/μL Taq polymerase, 1× Buffer, 200 nM forward primer, 200 nM reverse primer. Forward primer: 5'-CCGACGTGTTCCCACTGC (SEQ ID NO:84; corresponding to nucleotides 140200 to 140217 of *Homo sapiens* BAC clone RP11-635L1; see FIG. 16) and reverse primer: 5'-CGCACGGAGAGAAATGTGTG (SEQ ID NO:85; corresponding to the complement of nucleotides 140510 to 140529 of *Homo sapiens* BAC clone RP11-635L1; see FIG. 16 (SEQ ID NO:100)). Conditions were as follows: 5-min denaturation step at 95° C., 40 cycles of 30 s at 95° C., 30 s of annealing at 54° C., and 30 s extension at 72° C., followed by a final extension for 7 min at 72° C. The 330 bp PCR products were separated on 1.5% agarose gels and visualized with syber green and UV light. Ten μL of each PCR product was digested using AatII from NEB in 1× digestion buffer for 1 hour at 37° C. Amplicons containing the C to T mutation cut once giving 102 bp and 228 bp bands, while the amplicons from wild type DNA will not be cut by this restriction enzyme. This 330 bp fragment can also be sequenced using the PCR primers listed above.

Constructs and Transfection

The human wild-type (WT) palladin construct was made by PCR-cloning the entire coding sequence from a human palladin cDNA clone (human cDNA clone hk07554) into the sites of EcoRI and BamHI of phrGFP IIN vector (Stratagene), downstream of, and in frame with, the green fluorescent protein (GFP) tag. To create the Family X mutant construct (FX), Quick-Change Multi Site-Directed Mutagenesis (Stratagene) was used, with primers centered at the Family X mutation (P239S), according to manufacturer's protocol. Briefly, (1) 100 ng of WT construct was added as a template to a PCR cocktail containing 2.5 μl of 10× mutagenesis buffer, 100 ng of mutagenesis primer containing the Family X mutation, 250 μM each dNTP, 1 QuickChange enzyme blend and 1 μl QuickSolution. The PCR cycling parameters were one cycle of: 1 min at 95° C., followed by 30 cycles of 1 min at 95° C., and 15 min at 65° C.; (2) the parental template DNA was treated with DpnI (10 U) at 37° C. for 60 min; (3) 4 μl of this reaction was transformed into XL10 Gold Ultracompetent cells (Stratagene); and (4) several clones were chosen for PCR and/sequencing to confirm the incorporation of the mutation.

HeLa Cell Transfection

Transfection was performed using a Fugene kit (Roche Diagnostics) on human cancer epithelial cell lines (HeLa cells) according to the manufacturer's protocol. Briefly, (1) one day before the transfection, the cells were distributed into a six-well plate so that they would be approximately 70% confluent the next day; (2) 3-6 µl of transfection reagent was mixed with 94-97 µl of DMEM and left for 5 min; (3) then 1 µg of construct (either WT or FX mutant construct) was added to the complex and left for 10 min; (4) the complex was then added to the cells in a dropwise fashion; and (5) the expression of the GFP construct was observed the next day. Fluorescence staining was performed on cells fixed in 3.7% formaldehyde and permeabilized with 0.1% Triton X-100. The cells were then stained with 50 µg/ml of TRITC-phalloidin (Sigma) for 40 min, followed by washing with PBS. Finally, DAPI (Sigma) was added at 10 µg/ml to stain the nucleus, and antifade reagent (Invitrogen) was used to prevent auto-color bleaching. The construct/transfection experiments were run in triplicate and assessed blindly.

Analysis of Protein Levels

Size fractionation (SDS-PAGE) was performed on 20 µg of protein from each pancreatic cell line sample. The samples were individually loaded onto a gel, separated through electrophoresis, and then blotted onto a nitrocellulose membrane according to manufacturer's protocol (Amersham Biosciences, Piscataway, N.J., United States). The polyclonal palladin antibody (ab 621; Otey et al. (2005) *Int Rev Cytol.* 246:31-58) was used. A 1:2,000 dilution was used for Western blotting. The ECL plus kit (Amersham Biosciences) was used to detect protein in the Western blot.

Results

It was hypothesized that a mutated gene is best detected in very early pre-cancerous tissue, where the mutated gene has initiated neoplastic progression but before the genetic chaos of cancer has occurred. Using RNA from the pre-cancerous pancreatic tissue from a Family X member, the gene expression in the 4q32-34 region was profiled on a custom microarray. The custom array was created using 243 sequence-verified Unigene clones located between markers D4S2976 to D4S415, a region slightly larger than the region identified as the pancreatic cancer susceptibility locus (between markers D4S413-D4S2991). Unigenes represent a non-redundant set of gene-oriented clusters of cDNA clones assigned to a unique gene and genomic location. In addition to the Family X pre-cancer RNA, 10 different sporadic pancreatic cancers and 2 normal donor pancreata were also profiled. Samples were spotted in sextuplicates (6×) (FIGS. 3A-C). Comparative expression in Family X and the 10 pancreatic cancer samples were rank ordered by their degree of over or under-expression. Two Palladin clones were shown to be the most highly differentially expressed in sporadic pancreatic cancers and were also over expressed in Family X, using a J5 analysis which was used previously. Patel et al. (2004) *Appl. Bioinf.* 3:49-62. The J5 test compares the difference in mean expression for a given gene to the magnitude (absolute value) of mean difference in all of the genes on an array. Palladin clones were also shown to be among the most differentially expressed genes when Family X gene expression was analyzed by N-fold analysis.

To validate the findings on the custom microarray, commercially available primers directed toward exons 9 and 10 were used to measure gene expression of the Palladin gene (FIGS. 3A-C). Expression analysis via quantitative RT-PCR (qRT-PCR) was performed in a) 16 sporadic pancreatic cancers, b) 4 pre-cancerous tissues (2 from Family X and 2 from other familial pancreatic cancer families) c) 9 histologically normal appearing tissues adjacent to sporadic pancreatic cancers (normal adjacent) and d) 6 normal pancreas samples. Although the sample size was small, a significant difference was detected between all cancer and pre-cancer groups and normal pancreata (One way-4 group ANOVA $F(3.35)=5.86$, $p=0.003$). All possible pair-wise tests using Least Significant Difference test ($p<0.05$) showed significant differences between all cancer and pre-cancer groups (cancer, normal adjacent, PanIN) compared with normal. Palladin was over-expressed in most of the cancerous and precancerous pancreatic tissue, as well as in the histologically normal appearing tissue adjacent to the cancers, when compared to normal. This expression analysis indicates that Palladin is likely over-expressed very early in the development of pancreatic cancer—including both Family X and sporadic forms of the disease.

FIGS. 3A-C.

Identification of 4q32-34 Genes Differentially Expressed in Sporadic Pancreatic Cancer and In Family X Pre-Cancer. A). The Gene Discovery Array, a custom 4q32-34 microarray was interrogated using RNA derived from 10 sporadic pancreatic cancers, 1 pre-cancerous pancreas from an Family X individual and 2 normal donor pancreas samples. cDNAs were spotted six times. B). The top 2 most differentially expressed genes among 10 sporadic pancreatic cancers and the corresponding differential expression in Family X are shown. C). Average expression of Palladin using commercially available probes to Palladin exons 9 and 10. Samples tested included 6 normal pancreas samples, two from Stratagene and one each from Ambion, Biochain, Chemicon and Clontech, 4 PanIN III tissues (2 Family X individuals and 2 non-Family X individuals), 9 histologically normal tissue adjacent to cancer and 16 pancreatic cancer tissues. Error bars indicate 1 standard deviation above and below the average.

A Base Pair Substitution in Palladin Tracks with the Affected Members in Family X and Causes an Amino Acid Change in the Actinin Binding Site.

Palladin is an extremely large gene spanning 432 Kb, with a total of 31 exons, up to 9 probable alternative promoters, and at least 8 alternatively spliced transcripts. The published literature has described at least 3 major different isoforms of Palladin ranging in molecular weight from 140 kD, 120 kD and 90 kD. The smallest isoform (90 kD) is a constituent of the larger isoforms.

Figure 4:
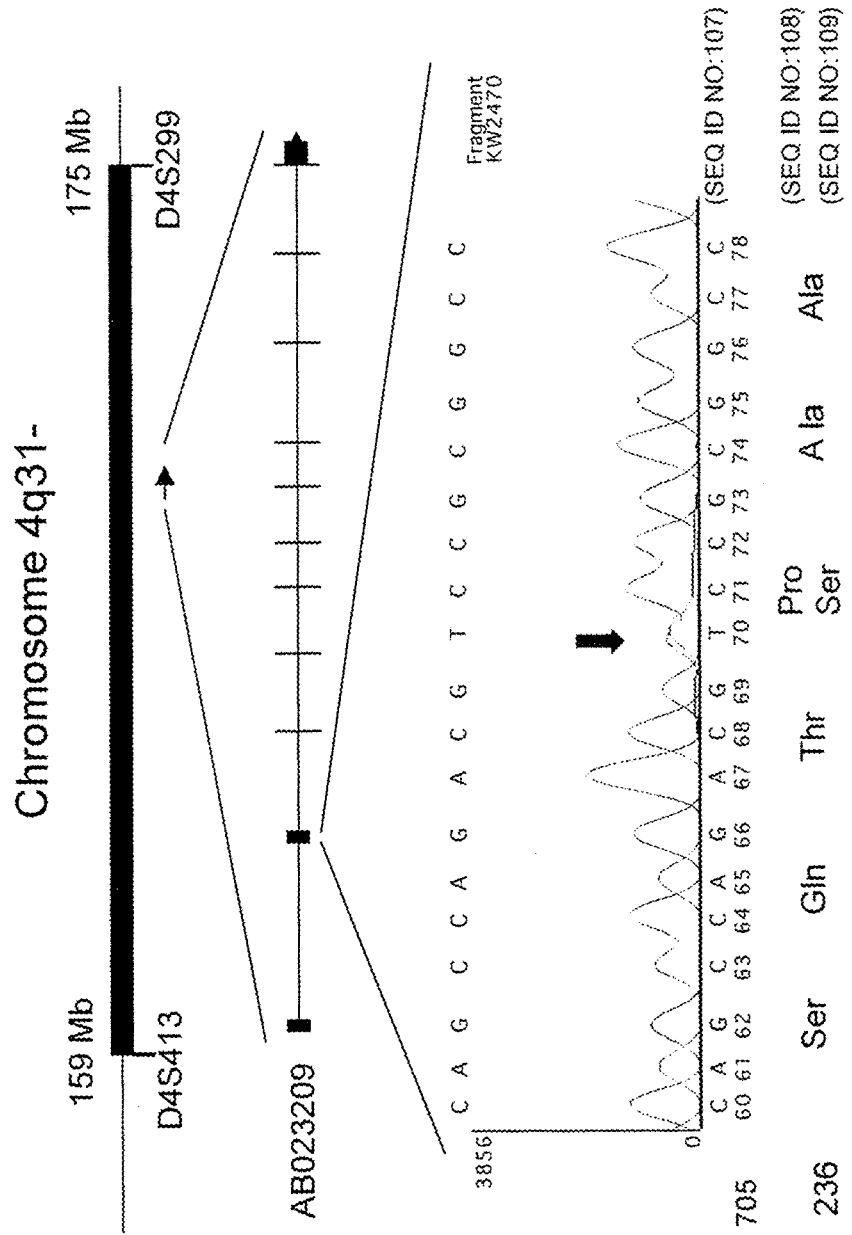
FIG. 4 depicts location and identification of the Family X mutation.

Twenty-nine individuals from Family X were available for mutational testing of Palladin: 9 unaffected, 12 with pancreatic cancer or pre-cancer, 9 known to be unaffected, and 8 with unknown status. Sequence analysis of Palladin identified a C to T base pair substitution in exon 2 of all 12 affected family members and none of the 9 unaffected family members. The C to T transition causes a proline (hydrophobic) to serine (hydrophilic) amino acid change at position 715 in Palladin RNA (FIG. 4).

FIG. 4.

Location and identification of the Family X mutation. Top black bar indicates the genomic location of the Family X mutation between microsatellite markers, D4S413 and D4S299, on chromosome 4 (Eberle et al. 2002) *Am. J. Hum. Genet.* 70:1044). Center line designates the location of the palladin transcript, AB023209, with vertical boxes and lines indicating exons. At the bottom a small portion of the DNA sequence is shown with a C to T transition at position 715 (indicated with an arrow) which causes a proline (hydrophobic) to serine (hydrophilic) amino acid change at amino acid 236.

The mutation discovered in Family X is contained in the cDNA clone AB023209 (FIGS. 1A and B), which encodes a 4,349 nucleotide transcript, containing 12 exons and encoding a 772 amino acid protein (90 kD isoform).

The mutation occurs in exon 2 of this Palladin isoform (peptide beginning MSALA, 126 amino acids downstream 90 kD start site).

This base pair substitution is not a known single nucleotide polymorphism, nor was it detected in the blood of 294 of 295 non-pancreatic cancer controls (589 of 590 alleles). One control blood sample revealed the mutation; unfortunately, the medical history of this individual is unknown. The Family X mutation occurs in a region that is highly conserved across species (FIG. 5).

FIG. 5.

The binding site of Actinin to Palladin is highly conserved across species. The mutation in Family X causes a proline (hydrophobic) to serine (hydrophilic) change in the amino acid sequence.

The 90 Kda Isoform of Palladin is the Major Isoform Expressed in Human Pancreatic Epithelium.

Figure 6:
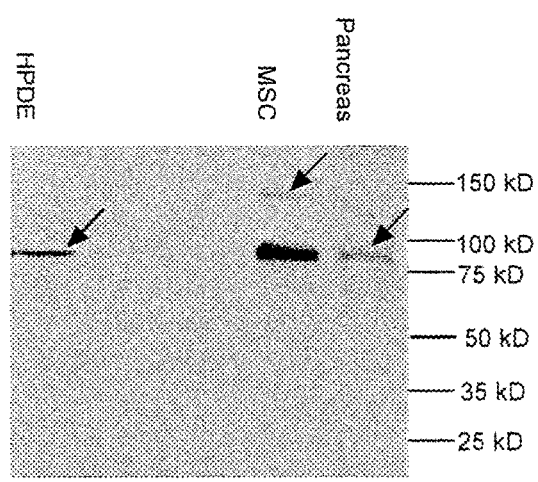
FIG. 6 depicts a blot of proteins extracted from various human cells and detected with polyclonal antibody against palladin raised in rabbit.

As shown in FIG. 6, at least three major isoforms of palladin are known, with molecular weights of 200 kDa, 140 kDa, and 90 kDa. The smallest isoform (90 kDa) is a component of the larger isoforms. Western blot analysis suggests that the 90 kD is the major isoform expressed in human pancreas (FIG. 6).

Western blotting and a polyclonal antibody (ab 621) were used to assess the protein isoform expressed in pancreatic ductal epithelium. The results indicated that the 90 kDa isoform is the predominant form of palladin in pancreatic ductal epithelium and in pancreatic cancer cell lines.

FIG. 6.

The 90 kD palladin is the major isoform expressed in human pancreas. Shown here is the western blot of the proteins extracted from various human cells detected with polyclonal antibody against palladin raised in rabbit (Ab 621). The major isoform expressed in human pancreas tissue and cultured epithelial cells (HPDE: human pancreatic ductal epithelial cell line) is the 90 kD isoform (e.g., arrow in "HPDE" lane). In the control sample (MSC: human mesenchymal stem cells), besides the major 90 kD isoform, the 140 kD isoform is also detectable (arrow in "MSC" lane).

Palladin Does Not Fit the Model of a Classical Tumor Suppressor Gene.

Loss of heterozygosity (LOH) studies have shown that a region in 4q32-35 is lost in many different cancers, including cancers of the pancreas, breast, colon, liver. Comparative genomic hybridization of pancreatic cancers using cDNA microarrays defined 3 different regions of LOH located between 4q32-35, suggesting that tumor suppressor gene might be localized to this region. Tumor suppressor genes lose activity when both alleles are inactivated: in many classical familial syndromes, one allele is inactivated through an inherited mutation and the second allele subsequently becomes lost, initiating neoplastic progression. To determine whether Palladin has genetic characteristics consistent with a classical tumor suppressor gene, a search for loss of a Palladin allele was conducted. A custom-made copy number chip (Nimblegen) was used to measure the number of alleles in pre-cancerous (PanIN II and III) pancreatic tissues from Family X members. The entire Palladin gene was interrogated and the copy number was 2 in every instance. In addition, two Palladin SNP probes with a minor allele frequency greater than or equal to 0.47 were used in TaqMan SNP analysis to test 21 sporadic pancreatic cancers for evidence of LOH. Ten sporadic pancreatic cancer tissue samples were heterozygous and thus, informative. None of these 10 samples showed loss of either allele in the tumor. These findings suggest that mutated Palladin is probably not a tumor suppressor gene, but rather may act as an oncogene.

Palladin is Increasingly Over-Expressed In Ductal Epithelial Cells with Neoplastic Progression.

Figure 7:
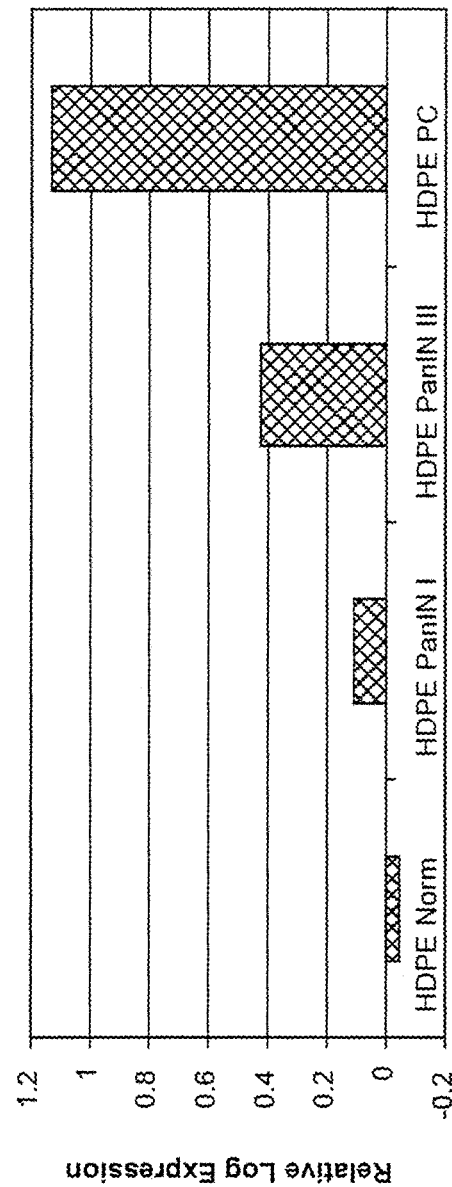
FIG. 7 is a graph depicting palladin expression in human ductal pancreatic epithelial (HDPE) primary cultures with neoplastic progression from normal ("HDPE Norm") to pancreatic intraepithelial neoplasia stage I ("HDPE PanIN I") to HDPE PanIN stage III ("HDPE PanIN III") to cancer ("HDPE PC").

Pancreatic cancer tumors are a mixture of tumor cells and a variety of other cell types due to the strong desmoplastic change common to pancreatic cancers. To determine whether the Palladin gene is expressed in the epithelial cells, the expression in primary human ductal pancreatic epithelial (HDPE) cells was examined with qRT-PCR. Epithelial cells were isolated from pancreatic tissue and grown in primary culture. Little to no expression could be detected in cells from a normal pancreatic ductal epithelium; in contrast, increasing expression was seen in epithelial cells derived from 2 different affected Family X individuals who had pre-cancer, but not cancer. The greatest expression was seen in ductal epithelial cells taken from an individual with a case of sporadic pancreatic cancer. The overexpression of Palladin increased as the epithelial cells became increasingly neoplastic (Pan I<PanIN III<Cancer) (FIG. 7).

FIG. 7.

Palladin expression in human ductal pancreatic epithelial (HPDE) primary cultures increases with neoplastic progression from normal (HPDE Norm) to PanIN I to PanIN III to cancer (HPDE PC). Each bar represents HPDE epithelial cultures from one person. The PanIN I and PanIN III lesions are from affected members of Family X. The pancreatic cancer epithelial cells are from a sporadic cancer.

Figure 8A:
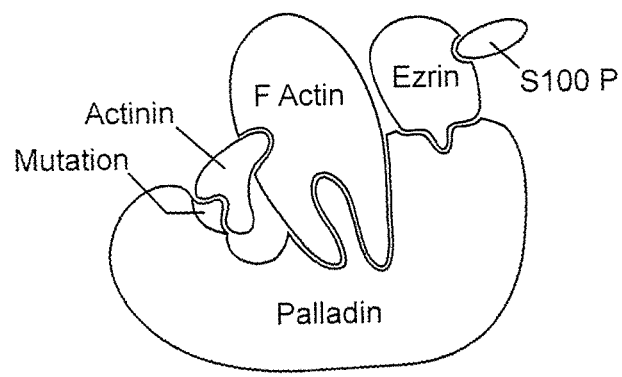
FIG. 8A schematically depicts a model of interaction of palladin with actinin and ezrin.
Figure 8B:
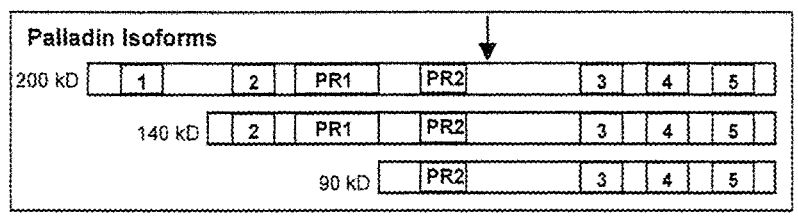
FIG. 8B schematically depicts various palladin isoforms.

Palladin is an actin-binding binding protein that controls cytoskeletal formation and cell movement. As depicted schematically in FIG. 8A, palladin binds other key proteins including actinin (the site of the Family X mutation), and ezrin. The pro→ser mutation identified in Family X occurs directly in the binding site for actinin (codons 243-258). FIG. 8B presents a schematic depiction of various palladin isoforms (90 kDa, 140 kDa, and 200 kDa). Proline-rich domains are designated PR1 and PR2, and the immunoglobulin-like (Ig-like) domains are numbered 1-5. The arrow marks the location of the Family X mutation.

Palladin and Alpha-Actinin Proteins are Abnormally Expressed in Sporadic Pancreatic Cancer Cell Lines.

Protein expression analysis of sporadic pancreatic cancer cell lines was performed, using protein ("western") blotting. The sporadic pancreatic cancer cell lines analyzed were PaTu1, PaTu2, Panc-1 (American Type Culture Collection (ATCC) accession number CRL-1469), FA6 (Morgan et al. ((2006) *Mol. Cancer.* 5:1), MiaPaca2, and HPAF-II (ATCC CRL-1997). PaTu1 and PaTu2 are described in, e.g., Missiaglia et al. ((2004) *Cancer* 112:100-112); FA6 is described in, e.g., Morgan et al. ((2006) *Mol. Cancer* 5:1). Abnormal palladin protein levels were detected in five of the six cell lines.

Figure 9:
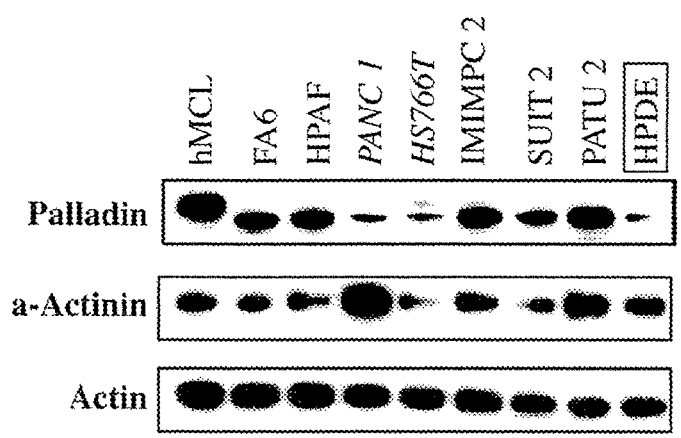
FIG. 9 depicts abnormal protein expression of palladin and α-actinin proteins in sporadic pancreatic cancer cell lines.

The 90 kDa palladin isoform co-localizes in stress fibers with several cytoskeletal components, such as actin and alpha-actinin. Protein expression of these cytoskeletal components in pancreatic cancer cell lines was examined using Western blotting and a polyclonal antibody (ab 621) to palladin. As shown in FIG. 9, of seven sporadic pancreatic cancer cell lines (FA6, HPAF, IMIMPC2, SUIT2, HS766T, PANC-1, and PATU2), five showed clear protein overexpression of palladin. Cell lines FA6, HPAF, IMIMPC2, SUIT2, and PATU2 overexpress palladin protein compared to the minimal expression in normal HPDE; alpha-actinin was also abnormally expressed in some of the pancreatic cancer cell lines, especially in PANC-1, a line that did not show overexpression changes in palladin protein.

These data suggest that abnormal expression of palladin or its binding partner, alpha-actinin, is present in six of the seven pancreatic cancer cell lines tested.

FIG. 9.

Abnormal protein expression of palladin and α-actinin proteins in sporadic pancreatic cancer cell lines. Human mesenchymal cell lysate (hMCL) was used as a positive control for palladin overexpression. FA6, HPAF, IMIMPC2, SUIT2, and PATU2 are sporadic pancreatic cancer cell lines that overexpress palladin protein compared to the minimal expression evident in normal HPDE. Alpha-actinin is also abnormally expressed in some of the pancreatic cancer cell lines compared to normal pancreas—especially PANC-1, one of the few pancreatic cell lines that does not show expression changes in palladin protein.

Overexpression of Mutant Palladin Results in Different Cellular Cytoskeletal Phenotypes It has been previously shown that palladin (90 kD isoform) colocalizes in the stress fiber with several cytoskeletal components, such as actin, actinin, ezrin, and Ena/VASP[5,7,8]. To investigate if the mutant form of palladin exhibits abnormality in this function, the human 90 kD isoform sequence was cloned into vector with GFP downstream, designated as wildtype construct. Site-directed mutagenesis was used to create a mutation of C to T at position 715 bp, resembling the Family X mutation, designated as FX construct. These constructs were transfected into Hela cells to study the overexpression phenotypes. Cells transfected with wildtype construct display well organized actin bundle, while GFP-palladin (wildtype) completely co-localize in the stress fiber with actin. When cells were transfected with FX construct, cells often exhibit almost normal actin bundle, however, GFP-mutant palladin frequently forms aggregates in these cells. Perhaps the most distinct phenotype for FX construct transfection is the presence of cells with multiple small blobs that do not colocalize with actin. In contrast, cells transfected with GFP empty vector exhibited green in the whole cells. These results suggest that mutant palladin may lose its ability to participate in regulating the actin networks, thus may impair the organization of normal cytoskeleton given the important role of palladin in the cytoskeleton.

Example 2

Additional Palladin Gene Mutations

Additional palladin gene mutations were identified: one in a pancreatic cancer cell line, a second in a family, designated Family U (or Utah Family 1); and a third in two other kindreds (Utah Family 2 and Seattle Family 2).

Materials and Methods

Mutant Palladin Construct

The human wild-type (WT) palladin construct was made by PCR-cloning the entire coding sequence from a human palladin cDNA clone (human cDNA clone hk07554) into the sites of EcoRI and BamHI of phrGFP IIN vector (Stratagene), downstream of, and in frame with, the green fluorescent protein (GFP) tag. To create a construct with the G→T mutation at position 1671, Quick-Change Multi Site-Directed Mutagenesis (Stratagene) was used with primers centered at the G→T mutation at position 1671, according to manufacturer's protocol. Briefly, (1) 100 ng of WT construct was added as a template to a PCR cocktail containing 2.5 μL1 of 10× mutagenesis buffer, 100 ng of mutagenesis primer containing the G→T mutation at position 1671, 250 μM each dNTP, 1 μl QuickChange enzyme blend and 1 μl QuickSolution. The PCR cycling parameters were one cycle of: 1 min at 95° C., followed by 30 cycles of 1 min at 95° C., and 15 min at 65° C.; (2) the parental template DNA was treated with DpnI (10 U) at 37° C. for 60 min; (3) 4 μl of this reaction was transformed into XL10 Gold Ultracompetent cells (Stratagene); and (4) several clones were chosen for PCR and/sequencing to confirm the incorporation of the mutation.

Transfection of HeLa cells was performed as described in Example 1. The transwell migration assay was performed essentially as described in Example 1.

Analysis of Protein Levels

Size fractionation (SDS-PAGE) was performed on 20 μg of protein from each pancreatic cell line sample. The samples were individually loaded onto a gel, separated through electrophoresis, and then blotted onto a nitrocellulose membrane according to manufacturer's protocol (Amersham Biosciences, Piscataway, N.J., United States). The polyclonal palladin antibody (ab 621; Otey et al. (2005) *Int Rev Cytol.* 246:31-58) was used. A 1:2,000 dilution was used for Western blotting. The ECL plus kit (Amersham Biosciences) was used to detect protein in the Western blot.

Results

1) Pancreatic Cancer Cell Line

The palladin gene in cell line PaTu2 was analyzed.

The Palladin Gene in PaTu2 Contains a Mutation.

It was found that a mutation occurs in the following sequence:

```
                                          (SEQ ID NO: 86)
GTCAGTGGGTTACCAACCCCAGATCTAAGCTGNCAACTAGATGGAAAG

CCCGTACGCCCTGACAGTGCTCACAAGATGCTGGTGCGTGAGAACGGG

GTGCACTCTCTGATCATAGAGCCAGTCACGTCACGTGATGCCGGCATC

TACACATGTATAGCTACCAACCGAGCAGGACAGAACTCATTCAGCCTG

GAGCTTGTGGTTGCTG,
``` where N=G/T at position 1671 of AB023209 in the ninth exon (see, e.g., GenBank AB023209; and FIGS. 1A and 1B). The wild-type sequence at position 1671 of AB023209 is G; the mutant has a T at position 1671. The G→T substitution results in a change in codon sequence of TGG→TGT, leading to a Trp→Cys mutation at amino acid 557 of palladin (see GenBank Accession No. BAA76836.1; and FIG. 12; SEQ ID NO:87):

VSGLPTPDLSXQLDGKPVRPDSAHKM-LVRENGVHSLIIEP (SEQ ID NO:88).

The Trp→Cys mutation occurs in a conserved region, the Ig2 domain of palladin:

```
Human
                                          (SEQ ID NO: 89)
VSGLPTPDLSWQLDGKPVRPDSAHKMLVRENGVHSLIIEP Mouse
                                          (SEQ ID NO: 90)
VSGLPTPDLSWQLDGKPIRPDSAHKMLVRENGVHSLIIEP
```

Primers suitable for use in amplifying a sequence containing the G→T substitution at 1671 of AB023209 include the following:

```
Forward primer:
5' TCTTGTACTACTGAAGGAGGAATTTATGC;      (SEQ ID NO: 91)
and

Reverse primer:
5' TTTTCCGTATTGGTTAGTAATGTAGAATTAG.    (SEQ ID NO: 92)
```

The position of the forward and reverse primers in genomic DNA is shown in FIG. 14, where the nucleotides corresponding to the primer sequences are underlined, exon 9 is shown in bold text, and the G→T substitution is underlined and in bold. The sequence amplified by these primers corresponds to nucleotides 183428 to 183828 of the *Homo sapiens* BAC clone RP11-635L1 as set forth in GenBank Accession No. AC080188.

The above forward and reverse primers result in an amplification product that contains either wild-type G at position 1671 of AB023209 or mutation T at position 1671 of AB023209. An amplification product containing the G→T mutation can be cut with HindIII; an amplification product containing the wild-type G at position 1671 of AB023209 is not cut with HindIII.

The W557C Mutation Alters Palladin Function.

An expression construct was made that includes a nucleotide sequence encoding the 90 kD isoform of palladin, and including the G→T mutation at position 1671, resulting in a Trp→Cys substitution at amino acid 557 (W557C). The expression construct included a green fluorescent protein (GFP)-coding sequence in-frame with the palladin-encoding nucleotide sequence. The construct was transfected into HeLa cells. HeLa cells expressing the mutant palladin/GFP protein exhibited cytoskeletal abnormalities. HeLa cells expressing the W557C mutant palladin/GFP protein exhibited a 200% increase in mobility in a transwell assay, compared to HeLa cells containing a control expression construct that included a nucleotide sequence encoding wild-type palladin 90 kD isoform.

2) Utah Family 1 Mutation

A family, referred to as "Utah Family 1," was analyzed for the presence of mutations in the palladin gene. A mutation occurs in the following palladin sequence:

```
                                           (SEQ ID NO: 93)
CCAACACTGAAAACTGTAGTTACGAGTCAATGGGAGAATCCAACAATG

ACCACTTCCAACACTTTCCACCTCCCCCTCCAATCTTGGAGACAAGTT

CCTTGGAGTTGGCTTCAAAGAAACCATCTGAGATCCAGCAGGTGAACA

ACCCTGAGTTAGGCCTGAGCAGGGCAGCCCTTCAAATGCAATTCAATG

CTGCTGAGAGGGAAACGAACGGAGTCCATCCCAGCNGTGGAGTAAATG

GACTGATTAACGGCAAAGCTAACAGTAATAAATCTCTTCCAACACCAG

CTGTCCTGCTTTCACCCACTAAGGAGCCACCACCTCTGCTTGCCAAAC

CAAAACT,
``` where N+C/T at position 2060 of NM_016081 in the tenth exon (see GenBank NM_016081; and FIGS. 13A and 13B). The wild-type sequence has a C at position 2060 of NM_016081; and the mutant has a T at position 2060 of NM_016081. The C→T substitution results in a change in codon sequence of CGT→TGT, leading to an Arg→Cys substitution at amino acid 617 of palladin (see GenBank Accession No. NP_057165.3; FIG. 12 (SEQ ID NO:871; and FIGS. 13A and 13B (SEQ ID NO:20)):

```
                                           (SEQ ID NO: 94)
NTENCSYESMGESNNDHFQHFPPPPPILETSSLELASKKPSEIQQVNN

PELGLSRAALQMQFNAAERETNGVHPSXGVNGLINGKANSNKSLPTPA

VLLSPTKEPPPLLAKPK.
```

The Arg→Cys mutation occurs in a conserved region of palladin, the poly-Pro region:

```
Human: AERETNGVHPSRGVNGLINGKA    (SEQ ID NO: 95)
Mouse: AERETNGVHPSHGVNGLINGKA.   (SEQ ID NO: 96)
```

Primers suitable for use in amplifying a sequence containing the C→T substitution at position 2060 of NM_016081 include the following:

```
Forward primer:
5' CACAACACAGGGATTCTCAGAAGA;    (SEQ ID NO: 97)
and

Reverse primer:
5' AGCTGGTGTTGGAAGAGATT.        (SEQ ID NO: 98)
```

The position of the forward and reverse primers in genomic DNA is shown in FIG. 15, where the nucleotides corresponding to the primer sequences are underlined, and the C→T substitution is underlined and in bold. The sequence amplified by these primers corresponds to nucleotides 26927 to 27313 of the *Homo sapiens* BAC clone RP11-592K15 as set forth in GenBank Accession No. AC084353.

The above forward and reverse primers result in an amplification product that contains either wild-type c at position 2060 of NM_016081 or mutation T at position 2060 of NM_016081. An amplification product containing the C→T mutation can be cut with PvuII; an amplification product containing the wild-type C at position 2060 of NM_016081 is not cut with PvuII.

3) Utah Family 2 and Seattle Family 2 Mutation

A family, referred to as "Utah Family 2," was analyzed for the presence of mutations in the palladin gene. A 12-bp insertion was found in the putative promoter region of the 90 kD isoform of palladin. Utah Family 2 had three members with pancreatic cancer, all cousins, as well as a family member with esophageal cancer and a member with breast cancer.

The same 12-bp insertion was detected in one of nine Seattle FPC kindreds tested, but was absent from 198 palladin alleles from normal control DNA. FIG. 19 presents a nucleotide sequence showing the promoter of the palladin gene encoding the 90 kDa isoform of palladin (boxed sequence), with a 12-bp insertion (bold sequence).

Table 1, below, presents a summary of mutations associated with pancreatic cancer.

TABLE 1

| Nt substitution (Codon) | Position | GenBank nt (GenBank protein) | Amino acid substitution | Position (Figure; SEQ ID) | Protein |
|---|---|---|---|---|---|
| C→T CCC→ TCC | cDNA nt 715 (Figure 1; SEQ ID NO: 1) Exon 2 Boundaries: nt 132-803 Genomic AC080188 Nt 140301 Figure 16 (SEQ ID NO: 100) | cDNA AB023209 (BAA76836.1) genomic AC080188 Nt 139718-140388 Figure 16 | Pro→Ser | aa 239; Figure 11 (SEQ ID NO: 99) | 90 kD isoform |

TABLE 1-continued

| Nt substitution (Codon) | Position | GenBank nt (GenBank protein) | Amino acid substitution | Position (Figure; SEQ ID) | Protein |
|---|---|---|---|---|---|
| G→T | cDNA nt 1671 (Figure 1; SEQ ID NO: 1) exon 9 boundaries: 1639-1846 genomic nt 183561 Figure 14 (SEQ ID NO: 101) | cDNA AB023209 (BAA76836.1) genomic Ac080188 Nucleotides 183529-183736 Figure 14 (SEQ ID NO: 101) | Trp→Cys | aa 557 Figure 11 (SEQ ID NO: 99) | 90 kD isoform |
| C→T | cDNA nt 2060 (Figure 13; SEQ ID NO: 20) exon 10 boundaries: 1833-2175 genomic nt 27251 Figure 15 (SEQ ID NO: 102) | cDNA NM_016081 (NP_057165.3) genomic AC084353 Figure 15 (SEQ ID NO: 102) | Arg→Cys | aa 617 Figure 12 (SEQ ID NO: 87) | 140 kD isoform |

Example 3

Palladin Gene Expression in White Blood Cells

Palladin mRNA levels were assessed in white blood cells (WBC) from normal individuals (e.g., individuals without pancreatic cancer), and from individuals with pancreatic cancer. The levels were normalized to the level of glyceraldehydes-3-phosphate dehydrogenase (GAPDH) mRNA present in the cells and to a standard sample following the ddCt method described previously (Pogue-Geile et al. (2004) *Cancer Genomics and Proteomics* 1:371-386). The data shown in FIG. 17, show the level of palladin mRNA in WBC from normal individuals (Nor-M1, —F1, F2, F4, RS28, RS45, RS48, RS72, and RS98) were higher than that in WBC from individuals with pancreatic cancer. The level of normalized palladin mRNA in WBC from individuals with pancreatic cancer was from about 0.4 to about 1.2 log lower than that in individuals without cancer. Thus, the level of palladin mRNA in WBC from individuals with pancreatic cancer (PG6, PG8, PG9, PG10, PG14, PG18, PG19, PG21, PA17, and PA25) was abnormally low.

Example 4

Palladin Expression in Various Cancers

Various cancer tissues were tested for reactivity with 1E6, a monoclonal antibody specific for the 90 kDa isoform of palladin. Rachlin and Otey (2006) *J. Cell Sci.* 119:995-1004. The data, shown in Table 2, below, indicate that palladin is over-expressed in at least breast cancer and in head and neck squamous cell cancer. The "1E6 grade" indicates, on a scale of 1+-3+, the level of antibody binding and thus the level of palladin protein over-expression.

TABLE 2

| Cases positive | 1E6 grade | Cancer type |
|---|---|---|
| 0/31 | — | Lung cancer, both small cell and non-small cell types |
| 0/15 | — | Renal cell |
| 2/15 | 1+ | Lobular breast cancer stroma |
| 3/7 | 1+ | Ductal breast cancer stroma |
| 1/18 | — | Colorectal cancer |
| 0/18 | — | Ovarian cancer |
| 13/15 | 1+ to 2+ | Head and neck squamous cell cancer stroma |
| 8/12 | 1+ to 3+ | Pancreatic ductal cancer stroma |
| 0/15 | — | Melanoma |
| 0/15 | — | Gastric cancer |
| 1/15 | — | Urothelial cancer (note: epithelial cells stained) |

Example 5

Effect of Palladin Mutation on Mobility

Cell Migration Assay

HeLa cells were first transfected with constructs of WT, FX, and empty vector respectively for 24 h, and then sorted for GFP-positive cells. The sorted cells continued to grow for 2 d before they were seeded onto a transwell plate for the migration assay. Migration assays were performed on 24-well Transwell cell culture chambers (Corning Costar Corporation, Cambridge, Mass., United States) fitted with multiporous (8-μm pore size) polycarbonate membranes. The upper chambers of the membrane were coated with fibronectin (10 μg/ml in PBS) 24-48 h before the assay. The upper chamber was then filled with 40,000 cells in suspension with 400 μl of medium (DMEM with 10% FCS), and the lower chamber was filled with 500 μl of the same medium. Plates were placed in a humidified $CO_2$ incubator at 37° C. for 17 h. Membrane inserts were then removed, fixed by immersing in ethanol five times with 1 s durations, and stained with 0.5% crystal violet dye (Sigma; #C3886) in 20% methanol for 30 min. After gentle rinsing with water, the nonmigratory cells on the upper surface of the membrane were removed with cotton swabs, leaving only the migratory cells within the membrane. The membrane insert was left to dry overnight and then placed in a 96-well plate. The dye was extracted with 30% acetic acid and the plate was placed on a shaker for 10 min to allow the dye to dissolve completely. The colorimetric absorbance was assessed at 590 nm. A transwell without cells was used as a background control. To correct for the cell numbers seeded in each transwell experiment, the optical density of all the original cells in the transwell (migrated and nonmigrated) was measured for each transfected cell type sample. By comparing the optical density from each sample type, a correction factor was provided for any variation in starting cell number between samples. Each sample was done in triplicate.

Mobility is Increased in Cells that Express Mutant Palladin.

It was hypothesized that the cytoskeletal changes in the cells containing the mutated Family X construct might provide a cancer phenotype, specifically increased cell motility. The cytoskeleton is essential for cell movement, and cell mobility is important for the invasive nature of cancer cells. HeLa cells transfected with one of three constructs of palladin (FX, WT construct, or an empty vector) were individually plated onto a fibronectin-coated membrane in a transwell chamber, and a migration assay was performed in a standard fashion. Hu et al. (2006) *FASEB J.* 20:1892-1894.

The cells transfected with the FX construct encoding P239S mutant palladin outpaced the other cells at every time point. As shown in FIG. 18, on average, 33% more cells with the FX construct migrated through the transwell than the cells with WT construct and 40% more than the cells with the empty vector. Therefore, P239S palladin expression induces increased cell motility, consistent with a proposed oncogenic function.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting pancreatic cancer in a biological sample, the method comprising:
   (a) contacting a detectably labeled nucleic acid probe with white blood cells in the sample, wherein the sample is blood, and wherein the probe specifically hybridizes with a palladin target nucleic acid; and
   (b) detecting the palladin target nucleic acid that is abnormally expressed in a white blood cell in the sample, wherein a detected level of palladin target nucleic acid that is at least about 0.4 log lower than a control level from normal white blood cells of the palladin target nucleic acid indicates that the sample is from an individual with pancreatic cancer, wherein the palladin target nucleic acid is a palladin mRNA that encodes the 90 kD isoform of palladin encoded by SEQ ID NO: 1, and wherein the probe is selected from SEQ ID NOs: 49-62 and complements thereof.

2. The method of claim 1, further comprising treating the individual from whom the sample was obtained with surgery, radiation, chemotherapy, or combinations thereof.

3. The method of claim 1, wherein the probe is selected from SEQ ID NOs: 49-54 and complements thereof.

4. The method of claim 1, wherein the probe is selected from SEQ ID NOs: 55-58 and complements thereof.

5. The method of claim 1, wherein the probe is selected from SEQ ID NOs: 59-62 and complements thereof.

6. A method of detecting pancreatic cancer in an individual, the method comprising:
   detecting a level of a palladin target nucleic acid in an indicator cell from the individual, wherein the indicator cell is a white blood cell, wherein the palladin target nucleic acid is a palladin mRNA that encodes the 90 kD isoform of palladin encoded by SEQ ID NO: 1,
   wherein the detecting comprises contacting a detectably labeled nucleic acid probe selected from SEQ ID NO: 49-62 and complements thereof with the indicator cell, and
   wherein detection of a level of a palladin target nucleic acid that is at least about 0.4 log lower than normal levels in the indicator cell indicates the presence in the individual of pancreatic cancer.

7. The method of claim 6, wherein the probe is selected from SEQ ID NOs: 49-54 and complements thereof.

8. The method of claim 6, wherein the probe is selected from SEQ ID NOs: 55-58 and complements thereof.

9. The method of claim 6, wherein the probe is selected from SEQ ID NOs: 59-62 and complements thereof.

10. A method of treating cancer comprising:
   a) detecting pancreatic cancer in a biological sample, wherein the biological sample comprises blood, wherein detecting the pancreatic cancer in the biological sample comprises detecting a palladin target nucleic acid that is abnormally expressed in a white blood cell in the sample, wherein the detecting comprises contacting white blood cells in the sample with a detectably labeled nucleic acid probe that specifically hybridizes with a palladin target nucleic acid, wherein a detected level of palladin target nucleic acid that is at least about 0.4 log lower than a control level from normal white blood cells of the palladin target nucleic acid indicates that the sample is from an individual with pancreatic cancer, wherein the palladin target nucleic acid is a palladin mRNA that encodes the 90 kD isoform of palladin encoded by SEQ ID NO: 1, and wherein the probe is selected from SEQ ID NOs: 49-62 and complements thereof; and
   b) treating the individual from whom the sample was obtained with surgery, radiation, chemotherapy, or combinations thereof.

11. The method of claim 10, wherein the probe is selected from SEQ ID NOs: 49-54 and complements thereof.

12. The method of claim 10, wherein the probe is selected from SEQ ID NOs: 55-58 and complements thereof.

13. The method of claim 10, wherein the probe is selected from SEQ ID NOs: 59-62 and complements thereof.

\* \* \* \* \*